(12) United States Patent
Kaufman et al.

(10) Patent No.: US 6,586,425 B2
(45) Date of Patent: *Jul. 1, 2003

(54) CYTOSKELETAL ACTIVE AGENTS FOR GLAUCOMA THERAPY

(75) Inventors: Paul L. Kaufman, Madison, WI (US); Benjamin Geiger, Rehovot (IL)

(73) Assignees: Wisconsin Alumni Research Foundation, Madison, WI (US); Yeda Research and Development Co., Ltd., Rehovot (IL)

( * ) Notice: Subject to any disclaimer, the term of this patent is extended or adjusted under 35 U.S.C. 154(b) by 0 days.

This patent is subject to a terminal disclaimer.

(21) Appl. No.: 09/772,412

(22) Filed: Jan. 29, 2001

(65) Prior Publication Data

US 2002/0045585 A1 Apr. 18, 2002

Related U.S. Application Data

(63) Continuation-in-part of application No. 09/621,124, filed on Jul. 21, 2000, now abandoned, which is a continuation of application No. 09/022,228, filed on Feb. 11, 1998, now Pat. No. 6,110,912, which is a continuation-in-part of application No. 08/604,568, filed on Feb. 21, 1996, now Pat. No. 5,798,380.

(51) Int. Cl.$^7$ .............................................. A61K 31/55

(52) U.S. Cl. ....................... 514/218; 514/456; 514/912; 514/913

(58) Field of Search ................................ 514/218, 456, 514/912, 913

(56) References Cited

U.S. PATENT DOCUMENTS

| | | | | |
|---|---|---|---|---|
| 4,170,398 | A | 10/1979 | Koester | 359/219 |
| 4,343,794 | A | 8/1982 | Podos | 424/646 |
| 4,757,089 | A | 7/1988 | Epstein | 514/571 |
| 4,863,912 | A | 9/1989 | Southren | 514/177 |
| 4,997,826 | A | 3/1991 | Southren | 514/177 |
| 5,306,731 | A | 4/1994 | Epstein | 514/562 |

OTHER PUBLICATIONS

Alberts et al., *Molecular Biology of The Cell*, pp. 787–860, Garland Publishing Inc. (1994).
Asseff et al., "Ocular penetration of pilocarpine in primates," *Amer. J. Ophthalmol.*, 75:212–215 (1973).
Bárány, "Simultaneous measurements of changing intraocular pressure and outflow facility in the vervet monkey by constant pressure infusion," *Invest. Ophthalmol.* 3(2):135–143 (1964).
Berkow et al. (eds.), *The Merck Manual of Diagnosis and Therapy* Sixteenth Edition, pp. 2386–2392, Merck & Co. Inc., Rahway, New Jersey (1992).
Bershadsky et al., "The state of actin assembly regulates actin and vinculin expression by a feedback loop," *J. Cell. Sci.*, 108:1183–1193 (1995).

Bill et al., "Effects of intracameral Na$_2$EDTA and EGTA on aqueous outflow routes in the monkey eye," *Invest. Ophthalmol. Vis. Sci.* 19:492–504 (1980).
Bill, "Basic physiology of the drainage of aqueous humor," *Exp. Eye Res.* 25:291–304 (1977).
Brubaker, "Clinical evaluation of the circulation of aqueous humor," in *Clinical Ophthalmology*, Duane (ed.), pp. 3:1–11, Harper & Row, New York (1986) not supplied.
Bubb et al., "Jasplakinolide, a cytotoxic natural product, induces actin polymerization and competitively inhibits the binding of phalloidin to F–actin," *J. Biol. Chem.*, 269:14869–14871 (1994).
Bubb et al., "Swineholide A is a Microfilament Disrupting Marine Toxin that Stabilizes Actin Dimers and Severs Actin Filaments," *J. Biol. Chem.* 270:3463–3466 (1995).
Bubb et al., "Effects of jasplakinolide on the kinetics of actin polymerization. An explanation for certain in vivo observations," *J. Biol. Chem.*, 275:5163–5170 (2000).
Cai et al., "Lactrunculin (LAT)–A effects on human trabecular meshwork (HTM) cells," Invest. Ophthamol. Vis. Sci., 40:S505. Abstract No. 2668 (1999).
Carmely and Kashman, "Structure of swinholide–A, a new macrolide from the marine sponge *Theonella swinhoei*," *Tetrahedron Lett.* 26:511–514 (1985).
Cooper, "Effects of cytochalasin and phalloidin on actin," *J. Cell. Biol.*, 105:1473–1478 (1987).
Coué et al., "Inhibition of actin polymerization by latrunculin A," *FEBS Lett.*, 213:316–318 (1987).
Crews et al., "Novel sponge derived amino acids. 1. Jasplakinolide, a cyclodepsipeptide from the marine sponge Jaspis sp." Tetrahed. Lett., 27:2797–2800 (1986).
Croft and Kaufman, "Effect of Daily topical ethacrynic acid on aqueous humor dynamics in monkeys," *Curr. Eye Res.* 14:777–781 (1995).
Croft et al., "Comparison of Goldmann tonometry measurements using creamer vs. fluorescein in cynomolgus monkeys," in *Basic and Clinical Applications of Vision Science*, Lakshminarayanan (ed.), pp. 231–216, Dordtecht, Kluwer, (1997).
Darnell et al., *Molecular Cell Biology*, pp. 815–858, Scientific American Books Inc. (1986).
Duncan et al., "Actin disruption inhibits bombesin stimulation of focal adhesion kinase (pp125$^{FAK}$) in prostate carcinoma,"0 *J. Surg. Res.*, pp. 359–363 (1996).

(List continued on next page.)

Primary Examiner—Zohreh Fay
(74) Attorney, Agent, or Firm—Quarles & Brady LLP

(57) ABSTRACT

Methods for the treatment of glaucoma are provided by the present invention. The compounds described cause a perturbation of the actin cytoskeleton in the trabecular meshwork or the modulation of its interactions with the underlying membrane. Perturbation of the cytoskeleton and the associated adhesions reduces the resistance of the trabecular meshwork to fluid flow and thereby reduces intraocular pressure.

19 Claims, 26 Drawing Sheets

OTHER PUBLICATIONS

Ehlers et al., "Applanation tonometry and central corneal thickness," *Acta Ophthalmol. (Copenh)* 53:34–43 (1975).

Epstein et al., "Acto–myosin drug effects and aqueous outflow function," *Invest. Ophthalmol. Vis. Sci.,* 40:74–81 (1999).

Erickson et al., "The cynomolgus monkey as a model for orbital research. III. effects on ocular physiology of lateral orbitotomy and isolation of the ciliary ganglion," *Curr. Eye Res.,* 3:557–564 (1984).

Fischbarg, "Active and passive properties of the rabbit corneal endothelium," *Exp. Eye Res.,* 15:615–638 (1973).

Gabelt and Kaufman, "Prostaglandin $F_{2\alpha}$ increases uveoscleral outflow in the cynomolgus monkey," *Exp. Eye Res.* 49:389–402 (1989).

Ganong, in *Review of Medical Physiology* Thirteenth Ed., pp. 117–136, Appleton and Lange (1987).

Geiger et al., "The molecular basis for the assembly and modulation of adherens type junctions," *Cell Diff. Dev.* 32: 343–354 (1990).

Gipson and Anderson, "Actin filaments in cells of human trabecular meshwork and Schlemm's canal," *Invest. Ophthalmol. Vis. Sci.,* 18:547–561 (1979).

Gupta et al., "Muscarinic receptor M1 and M2 subtypes in the human eye: QNB, pirenzipine, oxotremorine, and AFDX–116 in vitro autoradiography," *Br. J. Ophthalmol.* 78:555–559 (1994).

Guyton, *Textbook of Medical Physiology* Sixth Edition, pp. 386–389, W. B. Saunders Co. (1981).

Hadari et al., "Hepatic tyrosine–phosphorylated proteins identified and localized following in vivo inhibition of protein tyrosine phosphatases: effects of $H_2O_2$ and vandate administration into rat livers," *Mol. Cellular Endocrinol.* 97:9–17 (1993).

Harris, "Problems in drug penetration," in *Symposium on On Ocular Therapy,* Leopold (ed.), pp. 96–105, Mosby, St. Louis, MO, (1968) not supplied.

Hirsch et al., "Formation of intercellular spaces and junctions in regenerating rabbit corneal endothelium," *Exp. Eye Res.,* 23:385–397 (1976).

Isemura et al., "Mysoin light chain kinase inhibitors ML–7 and ML–9 inhibit mouse lung carcinoma cell attachment to the fibronectin substratum," *Cell Bio. Int. Rep.* 15(10):965–972 (1991).

Janes and Stiles, "The penetration of $C^{14}$–labeled atropine into the eye," *Arch. Ophthalmol.,* 62:69–74 (1959).

Jones and Maurice, "New methods of measuring the rate of aqueous flow in man with fluorescein," *Exp. Eye Res.,* 5:208–220 (1966).

Kam et al., "Mapping of adherens junction components using microscopic resonance energy transfer imaging," *J. Cell Sci.* 108:1051–1062 (1995).

Kase et al., "K–252a, a potent inhibitor of protein kinase C from microbial origin," *J. Antibiotic.* 39:1059–1065 (1986).

Kashman et al., "Latrunculin, a new 2–thiazolidinone macrolide isolated from the marine sponge *Latrunculia magnifica,*"*Tetrahedron Lett.* 21:3629–3632 (1980).

Kaufman and Bárány, "Loss of acute pilocarpine effect on outflow facility following surgical disinsertion and retrodisplacement of the ciliary muscle from the sclera spur in the cynomolgus monkey," *Invest. Ophthalmol.* 15:793–807 (1976).

Kaufman and Bárány, "Cytochalasin B Reversibly Increases Outflow Facility in the Eye of the Cynomolgus Monkey," *Invest. Ophthalmol. Vis. Sci.* 16(1):47–53 (1977).

Kaufman and Davis, "'Minified' Goldmann applanting prism for tonometry in monkeys and humans," *Arch. Ophthalmol.,* 98:542–546 (1980).

Kaufman and Lütjen–Drecoll, "Total Iridectomy In The Primate in vivo: Surgical Technique And Postoperative Anatomy," *Invest. Ophthalmol.* 14:766–771 (1975).

Kaufman and Mittag, "Medical Therapy Of Glaucoma," Ch. 9, Sec. II, pp. 9.7–9.30, in *Textbook of Ophthalmology Series, vol. 7: Glaucoma,* Podos and Yanoff (eds.), London, Mosby–Year Book Europe Ltd. (1994).

Kaufman and Wallow, "Minified diagnostic contact lenses for biomicroscopic examination and photocoagulation of the anterior and posterior segment in small primates,"0 *Exp. Eye Res.* 40:883–885 (1985).

Kaufman et al., "Cytochalasin B and D dose–outflow facility response relationships in the cynomolgus monkey," *Invest. Ophthalmol. Vis. Sci.,* 23:646–650 (1982).

Kaufman et al., "An actin drug for glaucoma," *Exp. Eye Res.,* 67(Suppl. XIII ICER Abstracts):S53 (1998).

Kaye et al., "Studies on the cornea. IX. Physiologic and morphologic effects of cytochalasin B on endothelium of rabbit corneas perfused in vitro," *J. Cell Biol.,* 61:537–543 (1974).

Kim et al., "Corneal endothelial cytoskeletal changes in F–actin with aging, diabetes, and after cytochalasin exposure," *Am. J. Ophthalmol.,* 114:329–335 (1992).

Kornberg et al., "Cell adhesion or integrin clustering increases phosphorylation of a focal adhesion–associated tyrosine kinase," *J. Biol. Chem.,* 267:23439–42 (1992).

Krupin and Civan, "Physiologic basis of aqueous humor formation," in *The Glaucomas, Basic Sciences,* 2nd ed., Ritch et al., (eds.), pp. 251–280, Mosby, St. Louis, MO., (1996).

Lowry et al., "Protein measurement with the folin phenol reagent," *J. Biol. Chem.,* 193:265–275 (1951).

Lyubimova et al., "Autoregulation of actin synthesis responds to monomeric actin levels," *J. Cell Biol.,* 65:469–478 (1997).

Matsumoto and Sasaki, "Staurosporine, A Protein Kinase C Inhibitor Interferes With Proliferation of Arterial Smooth Muscle Cells," *Biochem. Biophys. Res. Commun.* 158(1):105–109 (1989).

Maurice, "The movement of fluorescein and water in the cornea," *Am. J. Ophthalmol.,* 49:1011–1016 (1960).

Maus and Brubaker, "Measurement of aqueous humor flow by fluorophotometry in the presence of a dilated pupil," *Invest. Ophthalmol. Vis. Sci.,* 40:542–546 (1999).

McDermott et al., "Ophthalmic irrigants: a current review and update," *Ophthalmic Surg.,* 19:724–733 (1988).

McEvoy (ed.), *AHFS Drug Information* 93, pp. 1729–1753 and 1767–1779 (1993).

Ménage et al., "ε–Aminocaproic Acid Does Not Inhibit Outflow Resistance Washout in Monkeys," *Invest. Ophthalmol Vis. Sci.* 36(9):1745–1749 (1995).

Nakanishi et al., "KT5926, a potent and selective inhibitor of myosin light chain kinase," *Mol. Pharmacol.* 37:482–488 (1990).

Ota et al., "Endothelial permeability of the living cornea to fluorescein," *Invest. Ophthalmol.,* 13:945–949 (1974).

Ottersen and Vegge, "Ultrastructure and distribution of intercellular junctions in corneal endothelium," *Acta Ophthalmol. (Copenh)*, 55:69–78 (1977).

Peterson, "Review of the folin phenol protein quantitation method of Lowry, Rosebrough, Farr and Randall," *Anal. Biochem.*, 100:201–220 (1979).

Peterson et al., "Actin disrupting agents and their effects on anterior segment permeability in monkeys," *Exp. Eye Res.*, 67(Suppl. XIII ICER Abstracts):S176 (1998).

Peterson et al., "Latrunculin–A increases outflow facility in the monkey," *Invest. Ophthalmol. Vis. Sci.*, 40:931–941 (1999).

Peterson et al., "Effect of latrunculin–B on outflow facility in mokeys," *Exp. Eye Res.*, 70:307–313 (2000).

Peterson et al., "Latrunculins' effects on intraocular pressure, aqueous humor flow, and corneal endothelium," *Invest. Ophthalmol. Vis. Sci.*, 41:1749–1758 (2000).

Phelps et al., "Vision Research—A National Plan: 1983–87. 1987 Evaluation and Update," Report of the National Advisory Eye Council, NIH Publication No. 87–2755:231–278 (1987).

Posey and Bierer, "Actin stabilization by jasplakinolide enhances apoptosis induced by cytokine deprivation," *J. Biol. Chem.*, 274:4259–4265 (1999).

Poyer et al., "Age does not affect contractile responses of the isolated rhesus monkey ciliary muscle to muscarinic agonists," *Curr. Eye Res.* 12(5):413–422 (1993).

Poyer et al., "Prostaglandin $F_{2\alpha}$ effects on isolated rhesus monkey ciliary muscle," *Invest. Ophthalmol. Vis. Sci.* 36:2461–2465 (1995).

Reuner et al., "Autoregulatory control of actin synthesis in cultured rat hepatocytes," *FEBS Lett.*, 286:100–104 (1991).

Reuner et al., "Autoregulation of actin synthesis in hepatocytes by transcriptional and posttranscriptional mechanisms," *Eur. J. Clin. Chem. Clin. Biochem.*, 33:569–574 (1995).

Robinson and Kaufman, "Phalloidin inhibits epinephrines's and cytochalasin B'facilitation of aqueous outflow," *Arch. Ophthalmol.*, 112:1610–1613 (1994).

Sampath and Pollard, "Effects of cytochalasin, phalloidin, and pH on the elongation of actin filaments," *Biochem.*, 30:1973–1980 (1991).

Schwartz, "Argon Laser Trabecular Surgery in Uncontrolled Phakic Open Angle Glaucoma," *Ophthalmology* 88:203–212 (1981).

Senderowicz et al., "Jasplakinolide's inhibition of the growth of prostate carcinoma cells in vitro with disruption of the actin cytoskeleton," *J. Natl. Cancer Inst.*, 87:46–51 (1995).

Serpinskaya et al., "Stimulation of actin synthesis in phalloidin–treated cells. Evidence for autoregulatory control," *FEBS Lett.*, 277:11–14 (1990).

Simon et al., "Effect of corneal hydration of Goldmann applanation tonometry and corneal topography," *Refract. Corneal Surg.*, 9:110–117 (1993).

Spector et al., "Latrunculins: novel marine toxins that disrupt microfilament organization in cultured cells," *Science* 219:493–495 (1983).

Spector et al., "A structure activity study of latrunculin effects on microfilament organization," *J. Cell Biol.*, 103:393a (1986).

Spector et al., "Latrunculins–Novel Marine Macrolides That Disrupt Microfilament Organization and Affect Cell Growth: I. Comparison With Cytochalasin D," *Cell Motil. Cytoskel.* 13:127–144 (1989).

Spector et al., "New anti–actin drugs in the study of the organization and function of the actin cytoskeleton," *Microsc. Res. Techn.*, 47:18–37 (1999).

Tamaoki et al., "Staurosporine, A Potent Inhibitor of Phospholipid/$Ca^{++}$–Dependent Protein Kinase,"*Biochem. Biophys. Res. Commun.* 135(2):397–402 (1986).

Tian et al., "Combined effects of H–7 and cytochalasin B on outflow facility in monkeys," *Exp. Eye Res.*, 68:649–655 (1999).

Volberg et al., "Modulation of intercellular adherens–type junctions and tyrosine phosphorylation of their components in RSV–transformed cultured chick lens cells," *Cell Regulation* 2:105–120 (1991).

Volberg et al., "The effect of tyrosin protein phosphorylation on the assembly of adherens–type junctions," *EMBO J.* 11:1733–1742 (1992).

Volberg et al., "Effect of protein kinase inhibitor H–7 on the contracility, integrity, and membrane anchorage of the microfilament system," *Cell Motil. Cytoskel.* 29:321–338 (1994).

Way, *Current Surgical Diagnosis & Treatment* Eighth Edition, pp. 819–820, Appleton and Lange (1988).

Whitacre et al., "The effect of corneal thickness on applanation tonometry," *Amer. J. Ophthalmol.*, 115:592–596 (1993).

Wilensky and Jampol, "Laser Therapy for Open Angle Glaucoma," *Ophthalmology* 88:213–217 (1981).

Zabriskie et al., "Jaspamide, a modified peptide from Jaspis sponge, with insecticidal and antifungal activity," *J. Amer. Chem. Soc.*, 108:3123–3124 (1986).

Zhang et al., "Expression of muscarinic receptor subtype mRNA in the human ciliary muscle," *Invest. Ophthalmol. Vis. Sci.* 36:1645–1657 (1995).

Cai et al., "Effect of latrunculin–A on morphology and actin–associated adhesions of cultured human trabecular meshwork cells," *Mol. Vis.*, 6:132–43 (2000).

Citi et al., "Cytoskeletal involvement in the modulation of cell–cell junctions by the protein kinase inhibitor H–7," *J. Cell Sci.* 107:683–692 (1994).

Erickson–Lamy et al., "Ethacrynic Acid Induces Reversible Shape and Cytoskeletal Changes in Cultured Cells," *Invest. Ophthalmol. Vis. Sci.* 33:2631–2640 (1992).

Goodman and Gilman, *The Pharmacological Basis of Therapeutics* Seventh Edition, pp. 107–109, Macmillan Publishing Company (1985).

Honjo et al., "Effects of rho–associated protein kinase inhibitor Y–27632 on intraocular pressure and outflow facility," *Invest. Ophthalmol. Vis. Sci.*, 42:137–144 (2001).

Kaufman et al., "Advances in glaucoma diagnosis and therapy for the next millennium: new drugs for trabecular and uveoscleral outflow," *Semin. Ophthalmol,.* 14:130–43 (1999).

Kaufman et al., "Cytoskeletal and cell–junctional modulation of aqueous outflow," in Glaucoma Update VI, Krieglstein (ed.), pp. 191–195 Springer (2000).

Kiland et al., "Effects of latrunculin (LAT)–B on agueous humor dynamics, aqueous [protein], and corneal thickness in cynonolgus monkeys," *Invest. Ophthalmol. Vis. Sci.*, 39:S488 (1988).

Nagata, "Possible mechanisms of inositol phosphate–diacylglycerol signaling pathway in the regulation of intraocular pressure" *Nippon Ganka Gakkai Zasshi* 96: 865–871 (1992) [Japanese; abstract only (English)].

Paterson et al., "Total Synthesis of (–)-Preswinholide A," *J. Am. Chem. Soc.* 116:2615–2616 (1994).

Peterson et al., "In cynomolgus monkeys latrunculin (LAT)A, LAT–B increase outflow facility, LAT–A decreases intraocular pressure and initially increases aqueous humor formation," *Invest. Ophthalmol. Vis. Sci.*,38:S243 (1997).

Quick et al., "The Structure and Biological Activities of the Widely Used Protein Kinase Inhibitor, H7 Differ Depending on the Commercial Source," *Biochem. Biophys. Res. Comm* 187(2):657–663 (1992).

Robinson and Kaufman, "Cytochalasin B Potentiates Epinephrine's Outflow Facility–Increasing Effect," *Invest. Ophthalmol. Vis Sci* 32(4):1614–1616 (1991).

Tian et al., "The Protein Kinase Inhibitor H–7 Increases Outflow Facility and Inhibits Miotic But Not Accomodative Responses to Pilocarpine in Monkeys," *Invest. Ophthalmol. Vis. Sci.* 37:S202 (1996).

Tian et al., "Effects of Protein Kinase Inhibitors on Trabecular and Total Outflow Facility in Monkeys," *Invest. Ophthalmol., Vis. Sci.* 38:S812 (1997).

Tian et al., "H–7 disrupts the actin cytoskeleton and increases the outflow facility," *Arch Ophthalmol.* 116:633–643 (1988).

Tian et al., "Effects of H–7 on the iris and ciliary muscle in monkeys," *Arch Ophthalmol* 116:1070–1077 (1998).

Tian et al., "H–7 increases trabecular facility and facility after ciliary muscle disinsertion in monkeys," *Invest Ophthalmol Vis Sci* 40:239–242 (1999).

Tian et al., "Cytoskeletal involvement in the regulation of aqueous humor outflow," *Invest. Ophthalmol. Vis. Sci.,* 41:619–623 (2000).

Tian et al., "Acute effects of H–7 on ciliary epithelium and corneal endothelium in monkey eyes," *Curr Eye Res* (in press).

Tian et al., "Effects of the marine macrolides swinholide A and jasplakinolide on outflow facility in monkeys," (submitted).

Yoshimura et al., "Analysis of Protein Kinase Activities in Rabbit Ciliary Processes: Identification and Characterization Using Exogenous Substrates," *Exp. Eye Res.* 45:45–56 (1987).

LATRUNCULIN A

CYTOCHALASIN D

STAUROSPORINE

KT5926

H-7

SWINHOLIDE-A

CYTOSKELETAL ACTIVE AGENTS FOR GLAUCOMA THERAPY

The present application is a Continuation-in-Part of U.S. patent application Ser. No. 09/621,124, filed Jul. 21, 2000 now abandoned, which is a Continuation of U.S. patent application Ser. No.: 09/022,228, filed on Feb. 11, 1998 now U.S. Pat. No. 6,110,912, which is a Continuation-In-Part of U.S. patent application Ser. No. 08/604,568, filed Feb. 21, 1996, which is now U.S. Pat. No. 5,798,380, which issued on Aug. 25, 1998.

The present invention was made with government support from the National Institutes of Health (Grant EY 02698). The United States Government has certain rights in the invention.

FIELD OF THE INVENTION

The present invention relates to the treatment of ocular disorders of the eye and more particularly to the treatment of glaucoma.

BACKGROUND OF THE INVENTION

I. Description And Characterization Of Glaucoma

Glaucoma is an ophthalmologic disorder responsible for visual impairment. It is the fourth most common cause of blindness and the second most common cause of visual loss in the United States, and the most common cause of irreversible visual loss among African-Americans. Generally speaking, the disease is characterized by a progressive neuropathy caused at least in part by deleterious effects resulting from increased intraocular pressure on the optic nerve. In normal individuals, intraocular pressures range from 12 to 20 mm Hg., averaging approximately 16 mm Hg. However, in individuals suffering from glaucoma, intraocular pressures generally rise above 25 to 30 mm Hg. and can sometimes reach 70 mm Hg. Importantly, the loss of vision can result from intraocular pressures only slightly above or even within the statistically normal range, in eyes which are unusually pressure-sensitive, over a period of years. Moreover, extremely high pressures (e.g., 70 mm Hg.) may cause blindness within only a few days (See e.g., Kaufman and Mittag, "Medical Therapy Of Glaucoma," in Kaufman and Mittag (eds.), *Glaucoma* (Vol. 7 of Podos and Yanoff (eds), *Textbook of Ophthalmology* Series). London, Mosby-Year Book Europe Ltd. [1994], pp. 9.7–9.30; and Guyton, *Textbook of Medical Physiology,* 6th ed. (W. B. Saunders Co.), pp. 386–89[1981]).

Several different types of glaucomas exist, each having different pathophysiologies and risk factors. In terms of classification, glaucomas may first be deemed to be either "primary" or "secondary." Primary glaucomas, discussed further below, result directly from anatomical and/or physiological disturbances in the flow of aqueous humor (i.e., intraocular fluid). Secondary glaucomas occur as a sequel to ocular injury (e.g., trauma inflicted to the eye) or preexisting disease (e.g., an intraocular tumor or an enlarged cataract). Though the various secondary glaucomas have different etiologies, they are similar to the primary glaucomas in that they all produce visual loss through optic neuropathy.

The major types of primary glaucomas include (i) open-angle glaucoma (also known as chronic or simple glaucoma), (ii) angle-closure glaucoma (also known as closed-angle or narrow-angle glaucoma), and (iii) congenital glaucoma (also known as infantile glaucoma).

Open-angle glaucoma constitutes approximately 90% of all primary glaucomas. Open angle glaucoma is characterized by abnormally high resistance to fluid drainage from the eye. Intraocular pressure rises to the level required to drive the fluid normally produced by the eye, whose rate of formation is not altered in glaucoma, across the elevated resistance, according to the normal laws of physics governing passive bulk fluid flow across a resistance and down a pressure gradient. Normal resistance is required to maintain an intraocular pressure sufficient to: (i) maintain the shape of the eye (i.e., to keep it inflated) for optical integrity, and (ii) provide a pressure gradient to allow for the flow of aqueous humor, a fluid produced by the eye which provides for the metabolic needs of the avascular cornea and lens. This resistance is provided by the trabecular meshwork (TM), a complex tissue consisting of specialized endothelial cells, connective tissue beams, and extracellular matrix.

Angle-closure glaucoma entails closure or blockage of the anterior chamber angle by another ocular structure (usually the iris), thereby restricting outflow of aqueous humor. Though angle-closure glaucoma only constitutes approximately 5% of primary glaucomas, it requires immediate medical attention (See e.g., Kaufman and Mittag, "Medical Therapy Of Glaucoma," supra).

II. Etiology of Glaucoma

Glaucoma has been associated with both pharmacological and non-pharmacological factors. Non-pharmacological factors include age, race, family history, diabetes, and blood pressure. For example, African Americans are four-to-five times as likely to develop open-angle glaucoma as are Caucasians. Similarly, open-angle glaucoma is much more prevalent in individuals over the age of 40, and especially in those over 60 years of age.

In addition, particular drugs have been associated with glaucoma. The corticosteroids (e.g., prednisone, dexamethasone, and hydrocortisone) are known to induce glaucoma following both ophthalmic and systemic administration by increasing resistance to aqueous humor outflow through the trabecular meshwork via a mechanism somehow genetically linked to primary open angle glaucoma. Dexamethasone has been associated with the most pronounced increase in intraocular pressure, and ophthalmic administration generally leads to greater increases than systemic administration.

Topically applied ophthalmic drugs which dilate the pupil (adrenergic agonists such as phenylephrine and epinephrine; anticholinergics such as atropine, scopolamine, homatropine, cyclopentolate and tropicamide) may induce angle-closure glaucoma, while the anticholinergics can increase resistance to aqueous humor outflow in susceptible individuals even without causing angle-closure, apparently related to their cycloplegic (ciliary muscle/accommodation-paralyzing) action. Adrenergic (e.g., central nervous system stimulants, appetite suppressants) and anticholinergic (e.g., bowel relaxants and tricyclic antidepressants) agents administered systemically may also induce angle closure glaucoma, via secondarily dilating the pupil.

III. Therapeutic Modalities

Current glaucoma therapies are restricted to reducing intraocular pressure. Presently, both surgical and pharmacological treatments are used.

A. Surgical Treatment

Both laser and incisional surgical procedures are employed. Although open-angle glaucoma is generally controlled by pharmacological agents, laser trabeculoplasty or filtering surgery to improve aqueous drainage can be considered in severe cases (See e.g., *The Merck Manual of Diagnosis and Therapy* (16th Edition, 1992); Sec. 17: Ophthalmologic Disorders; Subsec. 227: Glaucoma; and Wilensky and Jampol, "Laser therapy for open angle glaucoma," Ophthalmol., 88:203–212[1981]).

Because it constitutes a medical emergency, angle-closure glaucoma is the type of glaucoma that most frequently requires surgical intervention. As noted above, angle-closure glaucoma entails closure or blockage of the anterior chamber angle, thereby restricting outflow of aqueous humor. Angle-closure glaucoma can often be permanently cured by laser peripheral iridectomy performed within 12–48 hours after the onset of symptoms (Current Surgical Diagnosis & Treatment, 8th ed., Appleton & Lange, pp. 819–820[1988]). Though often necessary and quite effective for both open- and closed-angle glaucoma, surgical intervention is an invasive form of treatment, even if local anesthesia can be used.

B. Pharmacological Treatment

Chronic open-angle glaucoma is generally treated by ocular administration of one of several agents. For a particular patient, the concentration of the agent and the frequency of administration is generally determined by trial and error, beginning with one of the weaker available preparations (e.g., pilocarpine 1%). The miotic agents (i.e., agents that causes the pupil to contract) represent one frequently used class of glaucoma drugs. Though the precise mechanism of action has not yet been fully elucidated, the miotic drugs lower intraocular pressure in patients suffering from open angle glaucoma by facilitating aqueous humor outflow, in turn consequent to mechanical deformation of the trabecular meshwork by drug-induced contraction of the ciliary muscle. The miotics, appropriately referred to as cyclotonics in this context, may be either direct-acting (e.g., pilocarpine and carbachol, which act on the muscarinic receptors of the ciliary muscle to produce contraction) or indirect-acting (e.g., anti-cholinesterases, such as echothiophate and isoflurophate, which prevent the degradation of the endogenous cholinergic neurotransmitter acetylcholine, thereby permitting strong and continuous contraction of the ciliary muscle). The adverse effects associated with the miotic agents include painful ciliary or accommodative spasm and consequent induced fluctuating myopia and blurred vision (in patients under the age of approximately 45 years), ciliary or conjunctival congestion, ocular pain, headache, and the miosis itself, which can cause a disabling reduction of vision in elderly patients with early cataract formation (the combination of the small pupil and the cloudy lens critically reduce the amount of light reaching the retina). The long-acting anticholinesterases are associated with the most severe and prolonged adverse effects, which may include development of cataracts or retinal detachment.

Several mydriatic agents are also useful in the initial treatment of open-angle glaucoma. For example, the sympathomimetic amines epinephrine and dipivefrin (a synthetic prodrug of epinephrine) lower intraocular pressure, at least in part through stimulation of $\beta_2$-adrenergic receptors in the trabecular meshwork (the mydriatic effect being irrelevant to the reduction in intraocular pressure). The adverse ocular effects of both agents include ocular congestion or hyperemia, ocular pain and headache, and blurred vision. In addition, epinephrine occasionally causes untoward systemic effects, such as palpitation, tachycardia, and hypertension.

In addition, the relatively new $\alpha_2$-adrenergic agonist apraclonidine has been shown to be effective in the treatment of glaucoma by inhibition of aqueous humor formation. As with many of the other topical anti-glaucoma preparations, apraclonidine is associated with both ocular (e.g., mydriasis and eyelid retraction) and systemic (e.g., dry mouth and nose) adverse effects.

Both non-selective $\beta_1$- and $\beta_2$-adrenergic blocking agents (e.g., timolol and levobunolol) and $\beta_1$-selective (e.g., betaxolol) adrenergic blocking agents are also used in the treatment of open-angle glaucoma. The mechanism of action likely entails reduction of aqueous humor formation. Adverse ocular effects include ocular stinging and discomfort, tearing, itching and/or foreign body sensation, and ocular dryness. Systemic cardiovascular and pulmonary adverse effects are of greater concern, are not uncommon especially in predisposed individuals (e.g., the elderly, patients with underlying cardiovascular or respiratory system disease, or those taking $\beta$-adrenergic blocking agents systemically for other conditions), and may occasionally be life-threatening.

In general, the above-mentioned agents can be used in combination therapy. For example, pilocarpine can be added to a timolol regimen to achieve further reduction in intraocular pressure. Similarly, an orally administered carbonic anhydrase inhibitor (e.g., acetazolamide) can be added to an ocular regimen to enhance treatment. Many adverse effects have been associated with the oral carbonic anhydrase inhibitors, including gastrointestinal, central nervous system, hematologic, renal, electrolyte (especially dangerous in patients with heart disease taking digitalis and other salt-wasting diuretics concurrently), and metabolic disturbances. Of course, the potential incidence of adverse effects increases when more than one agent is being used in a treatment regimen (See generally, McEvoy (ed.), AHFS Drug Information 93:1729–53 and 1767–79[1993]; and *The Merck Manual of Diagnosis and Therapy, supra*).

As set forth above, untreated glaucoma can result in severe consequences, including blindness. Clearly, new treatment methods and agents are needed and would be welcomed by those plagued by glaucoma who either cannot tolerate available treatment regimens or who are unwilling to undergo invasive surgical procedures.

SUMMARY OF THE INVENTION

The present invention describes chemical agents that can be used to treat glaucoma.

The compounds of the present invention cause a pharmacological perturbation of cellular contractility and perhaps secondarily, cell adhesions, mainly via disruption of the associated cytoskeletal structures or the modulation of their interactions with the membrane. Reduction in contractility and/or perturbation of these adhesions reduces the resistance of the trabecular meshwork to fluid flow and thereby reduces intraocular pressure in a therapeutically useful manner. However, an understanding of the mechanisms (e.g., the specific molecular mechanisms) is not necessary in order to utilize the present invention. Indeed, it is not intended that the present invention be limited to any particular mechanism (s).

The present invention contemplates methods of enhancing aqueous humor outflow in the eye of a subject to treat glaucoma, comprising: a) providing a subject with glaucoma; and b) administering to the subject an ophthalmic preparation comprising an effective amount of a non-comeotoxic serine-threonine kinase inhibitor, thereby enhancing aqueous humor outflow in the eye and treating the glaucoma. In one embodiment of the present invention, the serine-threonine kinase inhibitor is selected from the group consisting of H-7, ML-7, staurosporine, and KT-5926. In particular embodiments, the method of administration is topical. In other embodiments, the method of administration is intracameral. In still further embodiments, the method of administration is intracanalicular. In addition, the present invention provides compositions and methods suitable for the relaxation of actomysin (e.g., the potent contractile machinery consisting of actin and myosin filaments).

Moreover, the present invention contemplates a method of enhancing aqueous humor outflow in the eye of a subject to treat glaucoma, comprising: a) providing a subject with glaucoma; and b) administering to the subject an ophthalmic preparation comprising an effective amount of either H-7, staurosporine, or latrunculin-A, or a pharmaceutically acceptable salt thereof, thereby enhancing aqueous humor outflow in the eye and treating the glaucoma. In some embodiments, the method of administration is topical, whereas it is intracameral in other embodiments. In still further embodiments, the method of administration is intracanalicular.

In further embodiments, the present invention provides methods of enhancing aqueous humor outflow in the eye, comprising providing a subject and administering to said subject an ophthalmic preparation comprising an effective amount of a latrunculin B or a pharmaceutically acceptable salt thereof, thereby enhancing aqueous humor outflow in the eye and treating the glaucoma. In some preferred embodiments, the subject has glaucoma or is at risk for development of glaucoma. In alternative embodiments, the administration is topical, while in other embodiments the administration is intracameral, and still further embodiments the administration is intracanalicular. In some embodiments, the administration of latrunculin(s) (including but not limited to latrunculin-A) results in the binding of monomeric (G-) actin, which inhibits polymerization and leads to disruption of the actin networks.

The present invention provides effective and non-invasive methods of treating glaucoma without causing untoward and unacceptable adverse effects, such as corneal edema.

The present invention also provides methods of enhancing aqueous humor outflow in the eye of a subject, comprising: providing a subject, and administering an ophthalmic preparation comprising an effective amount of a non-corneotoxic cytoskeletal active agent that affects actin filaments to the subject, thereby enhancing aqueous humor outflow in the eye of the subject. In some preferred embodiments, the non-corneotoxic compound is a latrunculin. In some particularly preferred embodiments, the non-corneotoxic compound is selected from the group consisting of latrunculin-A and latrunculin-B. In other preferred embodiments, the non-corneotoxic compound is swinholide-A.

The present invention further provides methods of enhancing aqueous humor outflow in the eye of a subject, comprising: providing a subject and an effective amount of at least one non-corneotoxic ophthalmic preparation; and administering the non-corneotoxic ophthalmic preparation to the subject, wherein the preparation affects the actin filaments of the eye of the subject, and under conditions such that the aqueous humor outflow of the subject is enhanced. In preferred embodiments, the non-corneotoxic ophthalmic preparation comprises at least one macrolide. In particularly preferred embodiments, the macrolide is selected from the group consisting of latrunculin-A, latrunculin-B, swinholide-A, and jasplakinolide. In alternative embodiments, the subject has glaucoma. In still further embodiments, the administration is topical, while in other embodiments, the administration is intracameral, and in still further embodiments, the administration is intracanalicular.

The present invention also provides methods of enhancing aqueous humor outflow in the eye, comprising: providing a subject having glaucoma, and an ophthalmic preparation comprising an effective amount of at least one macrolide or a pharmaceutically acceptable salt thereof; and administering the ophthalmic preparation comprising an effective amount of a macrolide or a pharmaceutically acceptable salt thereof, to the subject thereby enhancing aqueous humor outflow in the eye of the subject, wherein the non-corneotoxic ophthalmic preparation affects the actin filaments of the eye of the subject. In particularly preferred embodiments, the macrolide is selected from the group consisting of latrunculin-A, latrunculin-B, swinholide-A, and jasplakinolide. In still further embodiments, the administration is topical, while in other embodiments, the administration is intracameral, and in still further embodiments, the administration is intracanalicular.

The present invention further provides methods for preventing the progression of glaucoma, comprising the steps of: providing a subject having glaucoma and a non-corneotoxic ophthalmic preparation that is capable of affecting actin filaments of an eye; and administering the non-corneotoxic ophthalmic preparation to the subject under conditions such that the progression of glaucoma is alleviated and/or prevented. In preferred embodiments, the non-corneotoxic ophthalmic preparation comprises at least one macrolide. In still further embodiments, the macrolide is selected from the group consisting of latrunculin-A, latrunculin-B, swinholide-A, and jasplakinolide. In still further embodiments, the administration is topical, while in other embodiments, the administration is intracameral, and in still further embodiments, the administration is intracanalicular.

Definitions

To facilitate understanding of the invention and the chemical schemes set forth in the disclosure that follows, a number of terms are defined below.

The term "ophthalmic preparation" refers to a composition containing a compound active so as to forestall the progression of glaucoma as well as other pharmaceutically acceptable ingredients. The characteristics of the composition will depend on a number of factors, including the mode of administration. For example, the composition may be a solution, suspension or the like that can be administered topically as an eyedrop. In addition, the composition may be in a form suitable for intracameral administration; for example, microinjection through the cornea into the anterior chamber so that the compound can reach the trabecular meshwork. Alternatively, the drug could be administered intracanalicularly (e.g., by retrograde microinjection into the venous collector channels draining Schlemm's canal or into Schlemm's canal itself). This eliminates the risk of corneotoxicity. The ophthalmic preparation may contain diluents, adjuvants and excipients, among other things.

The term "effective amount" refers to that amount of a preparation that is sufficient to produce the desired results. In particularly preferred embodiments, the term refers to that amount of an ophthalmic preparation that is required to successfully treat glaucoma. The effective amount of an ophthalmic preparation may depend on a number of factors, including the age, race, and sex of the subject and the severity of the glaucoma and other factors responsible for biologic variability. Though the term effective amount is not limited to a particular mechanism of action for a specific compound, an effective amount may be that amount of a compound able to disrupt cell junctions in the trabecular meshwork of the eye to increase aqueous humor outflow.

The term "subject" includes humans as well as other animals, including but not limited to primates, rodents, canines, felines, etc. Indeed, it is not intended that the term be limited to any particular animal or type of animal.

The term "glaucoma" refers to an ophthalmologic disorder responsible for visual impairment. The disease is characterized by a progressive neuropathy caused at least in part by deleterious effects resulting from intraocular pressure on the optic nerve. The term glaucoma refers broadly to both primary glaucomas, which include open-angle, angle-closure, and congenital glaucomas, and secondary glaucomas, which occur as a sequel to ocular injury or preexisting disease. Though not limited to any particular type of glaucoma, it is anticipated that the pharmacological agents and compounds of the present invention will be most efficacious in the treatment of open-angle glaucoma. In addition, the term encompasses subclinical or pre-clinical stages of glaucoma, in which the patient does not or has not yet begun to experience visual impairment. Thus, it is intended that the term encompass any stage and/or form of glaucoma.

The term "manifestations of glaucoma" refers to signs associated with glaucoma, including but not limited to loss of vision.

The term "aqueous humor outflow" refers to the drainage of aqueous humor from the eye. As described in further detail below, aqueous humor leaves the eye by passive bulk flow via two pathways at the anterior chamber angle, the trabecular or conventional route and the uveoscleral, posterior, or unconventional route. The term aqueous humor outflow refers to drainage via both pathways.

As used herein, the term "serine-threonine kinases" (or "ser-thr kinases") refers to enzymes that phosphorylate serine and/or threonine residues of proteins. In particularly preferred embodiments, the term encompasses kinases that affect actinomysin contractility.

The terms "serine-threonine kinase inhibitors" and "ser-thr inhibitors" refer to compounds known to be myosin light-chain kinase inhibitors. However, it is not intended that the term be limited to compounds that inhibit myosin light-chain kinase, as other targets are contemplated. These compounds primarily inhibit myosin light-chain kinase, thus inhibiting actomyosin-driven contractility; upon long exposure ($\geq 30$ minutes), they cause deterioration of the entire microfilament system. These changes affect predominantly cell-extracellular matrix (C-ECM) adhesions. The ser-thr inhibitors include, but are not limited to, H-7, KT-5926, ML-7, and staurosporine.

As used herein, the term "kinase inhibitor" refers to compounds that block kinases. Thus, it is not intended that the present invention be limited to myosin light-chain kinase inhibitors, as it is contemplated that other kinase inhibitors will find use in the present invention, including but not limited to rho kinase inhibitors. In addition, this term encompasses compounds that block contractility and/or affect adhesions and other cytoskeletal functions.

The term "non-corneotoxic" refers generally to the absence of medically-unacceptable side effects on the cornea. One of the primary side effects to be avoided is corneal edema, which is manifested by abnormal fluid accumulation within the intercellular spaces of the cornea. A main etiology of corneal edema is impairment of the corneal endothelium due to the introduction of drugs and other chemical compounds. Specular microscopy can be used to evaluate drug effects on the corneal endothelium, and the absence of a statistical change in corneal endothelial cell counts is indicative of a non-corneotoxic compound. In addition, the presence of corneal toxicity can be evaluated through ocular examination, which may include slit lamp biomicroscopy, gonioscopy, and corneal thickness measures.

The term "cytoskeletal active agent" refers broadly to compounds that affect the complex network of cytoplasmic filaments known collectively as the cytoskeleton. The three major classes of cytoskeletal filaments are actin microfilaments, intermediate filaments and microtubules. Generally speaking, cytoskeletal active agents work by perturbing the cytoskeletal filaments, through promotion of disruption of the filaments, interference with their stability, or disturbance of their interaction with other cytoskeletal components, and, indirectly, with the extracellular matrix.

The term "cell junctions" refers to cell-to-cell (C—C) interactions/adhesions and to cell-to-extracellular matrix (C-ECM) interactions/adhesions (i.e., C—C adhesions and cell-extracellular matrix [C-ECM] adhesions), both of which are necessary for integrated cellular activity and tissue architecture. Cell adhesion is closely associated with the actin microfilaments, which interact with both C-ECM and C—C junctions through a complex submembrane interlinking "plaque." Compounds which disrupt cell junctions may do so by affecting the junction directly or by disrupting the actin network or promoting its dissociation from the membrane-bound plaque. More specifically, compounds which interfere with the formation of the actin microfilaments, promote disruption of the filaments, interfere with actin assembly into bundles, or disturb the relationship between actin and myosin or the plaque will disrupt cell junctions and cause cells to pull apart from each other or from the extracellular matrix.

The compounds of the present invention encompass pharmacological agents that directly affect the trabecular meshwork of the eye and/or Schlemm's canal. The trabecular meshwork, a complex tissue consisting of specialized endothelial cells, connective tissue beams, and extracellular matrix, is responsible for the resistance to aqueous humor outflow. The compounds of the present invention affect, among other things, C—C and C-ECM adhesions in the trabecular meshwork.

DESCRIPTION OF THE FIGURES

FIG. 9B: 0.5 $\mu$M; FIG. 9C: 2.0 $\mu$M; and FIG. 9D: 5.0 $\mu$M).

FIG. 12B: 0.06 $\mu$M; FIG. 12C: 0.2 $\mu$M; and FIG. 12D: 2 $\mu$M). Anterior chamber (AC) exchange begins at time 0 (BL=baseline, Ex=2 ml exchange of AC with LAT-B or vehicle).

FIG. 13B: 4.0 $\mu$g). Each data point is the mean±s.e.m. of the facility readings at that time (some error bars are smaller than the symbols) for "n" monkeys, each contributing one LAT-B-treated and one vehicle-treated eye to the data set. Drug administration begins at time 0 (BL=baseline, AC=anterior chamber).

FIG. 15A and FIG. 15B show the results for 21 $\mu$g, while FIG. 15C and FIG. 15D show the results for 42 $\mu$g LAT-A. In these Figures, the solid line represents baseline (BL), while the dashed line is the initial difference between eyes at time 0. Data are shown as the mean±s.e.m. for number of monkeys indicated below the abscissa (i.e., each animal contributing one LAT-A-treated and one vehicle-treated eye to the data set). Differences between eyes after correcting for baselines ((LAT-A-BL)−(Veh-BL)) were significantly different from 0.0 (2-tailed paired t-test: $^\dagger p<b\ 0.1$, $^\pounds p<0.05$, $^\S p<0.025$, $^f p<0.02$, $^\# p<0.01, -p<0.005$).

DESCRIPTION OF THE INVENTION

The present invention relates to the treatment of glaucoma. While the present invention does not depend on an understanding of the mechanism by which successful treatment is accomplished, it is believed that the compounds of the present invention cause transient, drug-induced relaxation of cells and/or disssociation of C—C junctions and C-ECM junctions, which facilitates fluid flow around the cells, through the trabecular meshwork, and across the Schlemm's canal inner wall monolayer, leading to reduction in intraocular pressure.

Nonetheless, an understanding of the mechanisms is not necessary in order to use the present invention. Indeed, as indicated above, the present invention encompasses various methods and compositions that are suitable for increasing aqueous humor outflow by a number of mechanisms and it is not intended that the present invention be limited to any particular mechanism(s). In some embodiments, the present invention provides compositions and methods that sequester actin monomers and/or dimers, while in other embodiments, the compositions disrupt actin filaments or bundles of actin filaments. Thus, in some embodiments, actin is the primary target of the compositions. In alternative embodiments, the compositions and methods inhibit myosin light chain kinase, while in additional embodiments, the compositions inhibit the rho cascade. Thus, in other embodiments, actomysin interactions are the primary targets of the compositions of the present invention. However, it is not intended that the present be limited to these particular pathways. Indeed, it is contemplated that additional pathways will find use with the present invention. The only requirement of the present invention is that increased fluid conductance is produced through treated tissue. In particularly preferred embodiments, the trabecular meshwork is relaxed, resulting in an increase in fluid conductance through the tissue. In alternative preferred embodiments, the present invention provides means to alter the trabecular outflow pathway by affecting the actin cytoskeleton and actomyosin interactions, as well as by affecting cell adhesions.

The description of the invention is divided into the following parts: I) Anatomical Considerations And Aqueous Humor Dynamics; II) Structural Considerations of the Eye; III) Cell Culture, Animal Model, and Experimental Apparatus; IV) Evaluation of Compounds for Use in the Present Invention; V) Potential Therapeutic Chemical Compounds; and VI) Composition and Administration of Compounds. Each of these parts will be discussed in turn.

I. Anatomical Considerations and Aqueous Humor Dynamics

A. Anatomical Considerations

Figure 1A:
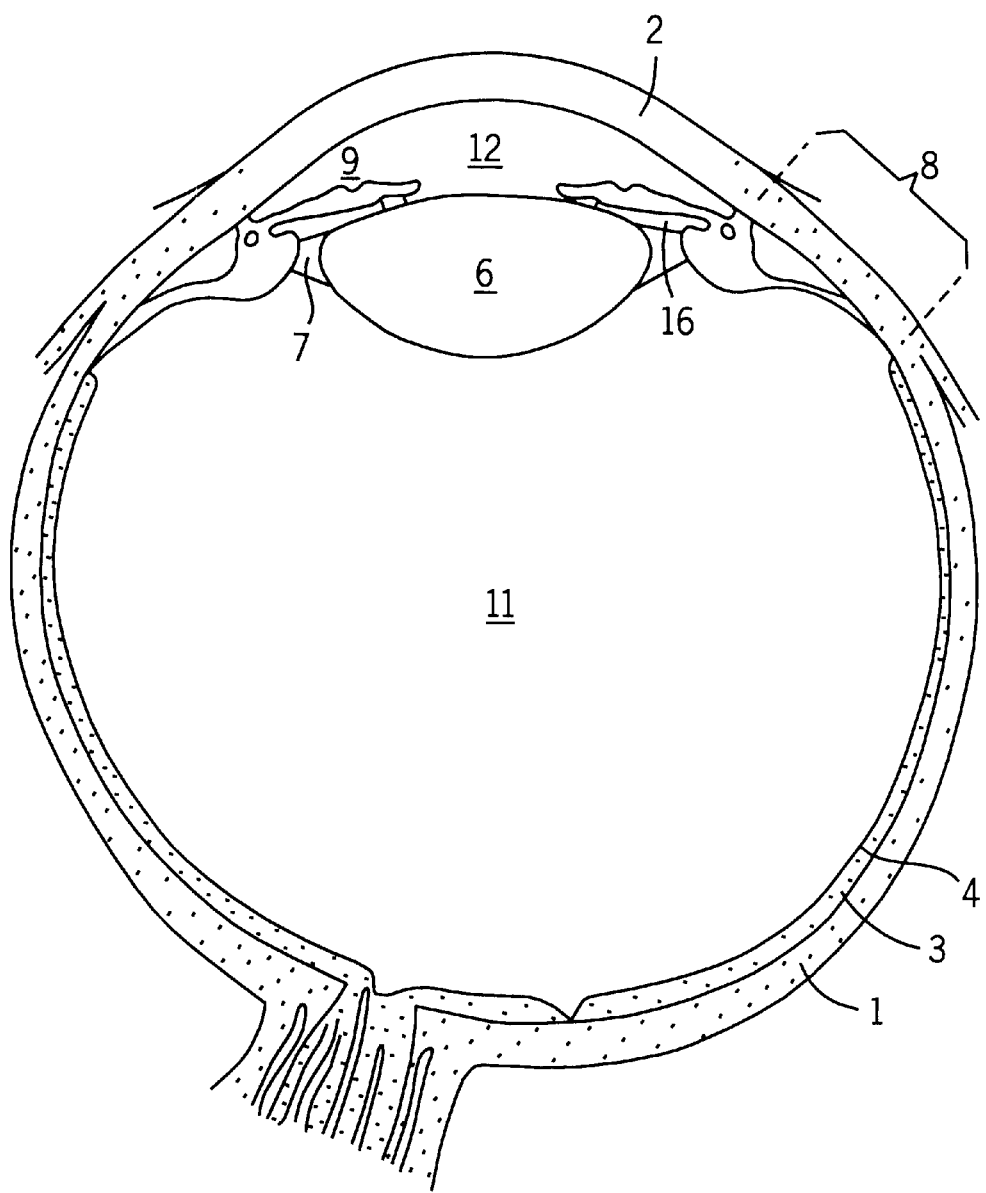
FIG. 1A schematically depicts the major anatomical structures of the eye.

The major anatomical structures of the eye are shown in FIG. 1A (See e.g., Ganong, *Review of Medical Physiology*, 13th ed., Appleton & Lange [1987], pp. 117–136). Referring to FIG. 1A, the eye is surrounded by an outer protective layer, the sclera (1). The anterior portion of the sclera (1), the cornea (2), is modified to allow light rays to enter the eye. The choroid (3) resides within the sclera (1) and comprises vasculature which nourishes most of the structures of the eyeball. The posterior portion of the choroid (3) (i.e., that portion opposite the cornea (2)) is lined by the retina (4). Generally speaking, the retina (4) is composed of the neural tissue containing the receptor cells that receive and process the incoming light rays.

FIG. 1A also depicts several other structures important for an understanding of the present invention. The transparent, biconvex lens (6), one of the refractive media of the eye, is secured by the lens ligament (zonule) (7) to the ciliary body (8). The ciliary body (8) is the thickened anterior portion of the choroid (3). The iris (9), the "colored" portion of the eye, lies in front of the lens (6) (i.e., the region between the lens (6) and the cornea (2)). The iris (9) is composed of circular muscle fibers (not shown) that constrict the pupil and radial muscle fibers (not shown) that dilate the pupil (See, Ganong, supra).

The relatively large region behind the lens (6) contains the vitreous humor (11), a clear gelatinous material. In contrast, the anterior chamber (12) of the eye contains a clear liquid material called the aqueous humor; the aqueous humor is also referred to as intraocular fluid. As described in more detail below, aqueous humor is produced in the ciliary body/ciliary processes (8). A region exists between the lens (6) and the iris (9), called the posterior chamber (16), that is also filled with aqueous humor.

B. Aqueous Humor Dynamics

One of the requirements of normal visual function is an optically clear pathway from the anterior corneal surface to the outer retina. This requirement precludes direct vascular perfusion of the transparent cornea (2) and lens (6) to satisfy their metabolic needs. The normal circulation of aqueous humor through the anterior chamber (12) and posterior chamber (16) against resistance not only satisfies corneal and lenticular metabolism, it also maintains optical clarity and the shape of the eye.

Figure 1B:
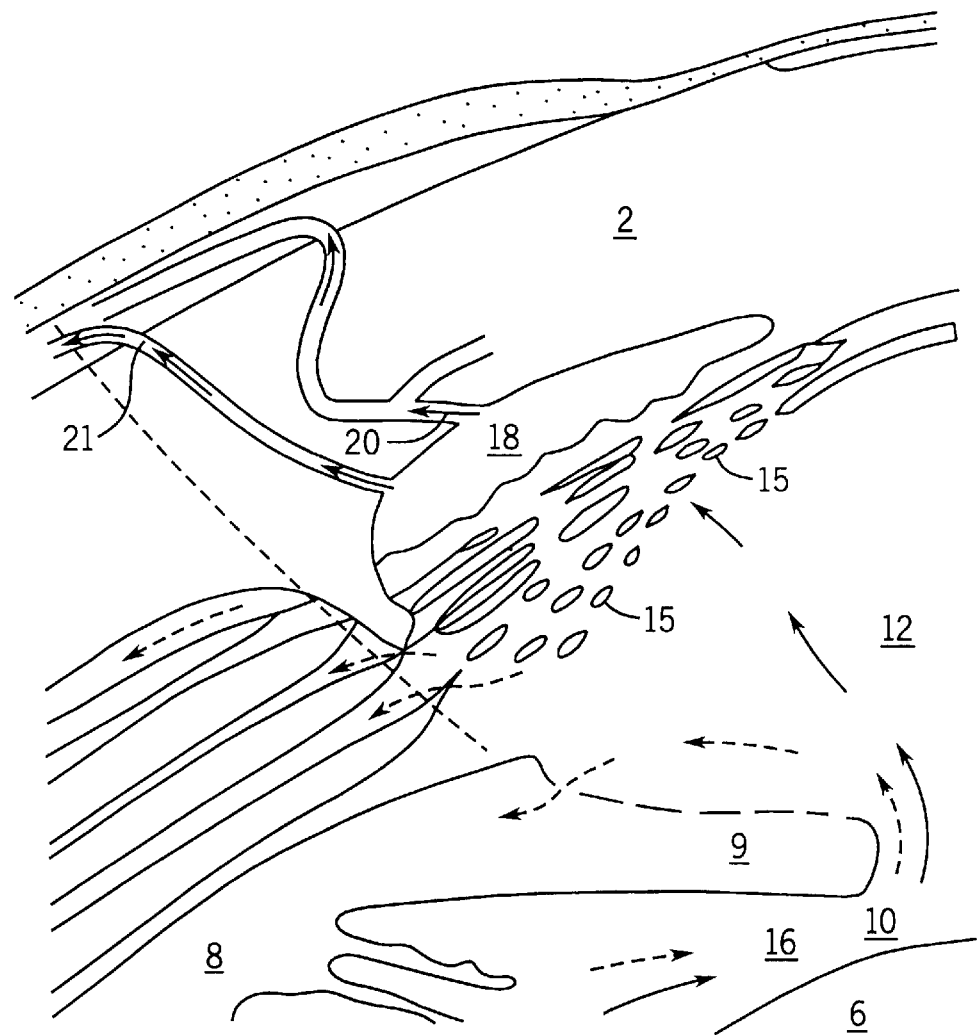
FIG. 1B schematically illustrates the basic anatomy of the primate anterior chamber angle. The trabecular (conventional) route of aqueous humor flow is indicated by the uninterrupted lines, while the uveoscleral (unconventional) route of aqueous humor flow is indicated by the dashed lines.

FIG. 1B schematically illustrates the basic anatomy of the primate anterior ocular segment and the normal pathways of aqueous humor flow. Aqueous humor enters the posterior chamber (16) from the ciliary body/ciliary processes (8) as a consequence of hydrostatic and osmotic gradients between the posterior chamber and the ciliary process vasculature and stroma and active ionic transport across the ciliary epithelium. The aqueous humor then flows around the lens (6) and through the pupil into the anterior chamber (12). The aqueous humor then leaves the eye by passive bulk flow via two pathways at the anterior chamber angle: (i) the trabecular or conventional route (hereafter "the trabecular route"), or (ii) the uveoscleral, posterior, or unconventional route (hereafter "the uveoscleral route"). With the trabecular route, aqueous humor travels through the trabecular meshwork (15), across the inner wall of Schlemm's canal (18) into its lumen, and then into collector channels (20), aqueous veins (21), and the general venous circulation (not labelled) (the trabecular route is indicated by the uninterrupted lines in FIG. 1B). In contrast, with the uveoscleral route, aqueous humor travels across the iris root, uveal meshwork, and the anterior face of the ciliary muscle, through the connective tissue between the muscle bundles, and then out through the sclera (the uveoscleral route is indicated by the dashed lines in FIG. 1B).

Aqueous humor is continually being produced and drained, and it is the balance between these two processes that regulates the pressure of the intraocular fluid. As previously indicated, glaucoma is characterized by elevated intraocular pressure. Briefly, open-angle glaucoma results from decreased permeability of the aqueous humor through the trabecular meshwork (15), whereas angle-closure glaucoma results from shifting of the iris (9) forward so that the anterior chamber angle (10) is obstructed.

II. Structural Considerations of the Eye

A. The Cytoskeleton

The shape, dynamics and adhesiveness of eukaryotic cells depends, to a large extent on a complex network of cytoplasmic filaments, known, collectively, as the cytoskeleton. There are three major classes of cytoskeletal filaments, including actin microfilaments, intermediate filaments and microtubules. Among these, most relevant for cell adhesion are the microfilaments which interact with both C-ECM and C—C junctions through a complex submembrane interlinking "plaque." Microfilaments are abundantly present in the cells of the corneoscleral and the juxtacanicular portions of meshwork and the inner wall of Schlemm's canal in cynomolgus and rhesus monkeys and humans (See, Gipson and Anderson, Invest. Ophthalmol. Vis. Sci., 18:547–561 [1979]).

Recent studies have established that this interaction with the cytoskeleton is essential for the formation of stable junctions. Indeed, epithelial and endothelial C—C and C-ECM junctions are dynamic structures which vary in number, location, and "adhesiveness," with the ambient physical and chemical milieu. Both types of adhesions are complex molecular entities comprising structural and signal transduction proteins, with the latter providing regulatory control over the former in response to intra- and extracellular conditions. In the trabecular meshwork (TM), both types of adhesions contribute to overall TM geometry and thereby, to flow resistance. Compounds that affect these adhesions and the contractile proteins that interact with them can alter the shape of these cells in the juxtacanicular meshwork and inner wall of Schlemm's canal, and thereby change the overall geometry and stability of the TM, so as to facilitate aqueous outflow and promote washout of resistance-producing ECM.

In forming this firm anchorage of actin filaments to the sub-membrane junctional plaque, several additional proteins participate, the perturbation of which might alter cell adhesion and which should thus be considered. These include both "anchor proteins" which are involved in the physical linkage of actin to the membrane, and myosin, an actin motor driven by ATP hydrolysis, which is responsible for muscle and non-muscle contractility. Myosin contains two identical heavy chains (M.W.~200,000) and two pairs of light chains of two different types (M.W.~20,000). In its active form, myosin light chain kinase (MLCK) catalyzes the phosphorylation of a myosin light chain, permitting myosin to interact with actin; this interaction results in the movement of myosin along the actin microfilament leading to cell contraction. Indeed, such movement is responsible for non-muscle and smooth muscle contraction. Moreover, it has been recently demonstrated that inhibition of this actomyosin contraction may lead to a generalized disruption of the microfilament system.

Another important domain of cell junctions, the perturbation of which may adversely affect junction integrity and permeability, is the submembrane plaque, a dense meshwork of proteins which links actin to the membrane. This plaque consists of a complex array of proteins including vinculin, and alpha actinin. In C—C adhesions, catenins are also present. It has been recently demonstrated that the submembrane plaque is a major sub-cellular target to tyrosyl-kinases and that augmentation or inhibition of this phosphorylation has dramatic effects on cell junctions (For general information, see, Alberts et al., *Molecular Biology Of The Cell*, Garland Publishing, Inc. [1994], pp. 787–861; Darnell et al., *Molecular Cell Biology* (Scientific American Books, Inc.) [1986], pp. 815–58; and Geiger, et al., Cell Different and Develop., 32:343–354[1990]).

Interference with the formation of the actin microfilaments, promotion of disruption of the filaments, interference with actin assembly into bundles, or disturbance of the relationship between actin and myosin or the plaque can cause cells to pull apart from each other or from the extracellular matrix. It should also be pointed out that compounds that affect junctions but that do not act through interactions with actin, are also candidates for therapeutic compounds. Ideally, perturbation of C—C adhesion might be selective, and achieved without completely breaking adhesions to the underlying extracellular matrix, avoiding a massive loss of cells. If such interference occurs in the fluid drainage pathways of the eye, it would enhance aqueous humor egress from the eye, with a concomitant lowering of intraocular pressure. This concept forms the basis for the use of the therapeutic compounds of the present invention.

B. The Ocular Trabecular Meshwork

The trabecular meshwork (TM) consists of interlacing connective tissue beams, each surrounded or "coated" by a single layer of endothelial-like cells. The beams form a latticework, comprising several layers. The spaces between the beams are filled with extracellular matrix, consisting of glycosaminoglycans, proteoglycans, and other macromolecules. The outer-most portion of the meshwork contains no beams, but rather several layers of endothelial cells imbedded in the "sea" of extracellular matrix. Just beyond this region is a small venous channel, the canal of Schlemm, which is connected to the general venous circulation. The pressure in Schlemm's canal is ~9 mm Hg. The resistance of the trabecular meshwork normally is such that intraocular pressure is ~16 mm Hg, at which aqueous humor leaves the eye at the same rate at which it is produced (2.5 $\mu$l/minute). The exact pathways by which aqueous humor flows through the meshwork and across the wall and thus into the lumen of Schlemm's canal, and the exact sites of resistance within the meshwork, are still unclear. However, it is clear that the barriers constituted by the cells, the extracellular matrix, and the adhesions between them are major determinants of both the flow pathways and the resistance to flow.

C. Pharmacological Effects on the Trabecular Meshwork

Several classes of drugs theoretically could act directly on the trabecular meshwork and Schlemm's canal to alter outflow facility. However, these classes of drugs may also affect smooth muscle, such as the ciliary muscle; ciliary muscle relaxation may cause an undesired decrease in facility. Because ciliary muscle contraction and relaxation cause an acute increase or decrease in facility, respectively, one must be able to determine whether a drug-induced facility change is due to a direct action on the conventional outflow channels or an indirect action exerted via altered ciliary muscle tone.

In primates, the ciliary muscle inserts at the scleral spur and trabecular meshwork (See, FIG. 1B). Surgically disinserting and retrodisplacing the entire circumference of the muscle from the scleral spur to a more posterior location in monkeys yields a physiologically and morphologically viable in vivo preparation in which ciliary muscle tone no longer influences outflow facility. This preparation allows distinction between trabecularanalicular/downstream drug effects on the one hand and ciliary muscle-mediated effects on the other. Indeed, this preparation was used to prove that pilocarpine's effect on outflow facility was mediated essentially completely by ciliary muscle contraction (See e.g., Kaufman and Bárány, Invest. Ophthalmol., 15:793–807 [1976]).

The disruption of overall trabecular meshwork architecture and the consequent increase in outflow facility by cytochalasins, calcium chelators, and sulfhydryl reactive agents has been studied in primates. However, these classes of agents collectively attack only a few of the potential cellular and junctional proteins whose alteration might rearrange meshwork geometry to therapeutic advantage. More importantly, these agents exert unwanted effects on other anterior segment structures whose integrity depends on those particular proteins. In addition, chelators and sulfhydryl reactive agents are not specific. Thus, the use of these compounds is problematic.

Regarding the cytochalasins, researchers have found that they interfere with actin filaments and enhance fluid outflow from the living monkey eye; this finding was first published in the mid-1970s (See e.g., Kaufman and Bárány, Invest. Ophthalmol. Visual Sci., 16(1):47–53[1977]). The cytochalasins are fungal metabolites. Though the precise mechanism by which the cytochalasins affect microfilament organization in living cells has not been fully elucidated, the mechanism is believed to entail interference with the dynamic equilibrium that exists in nonmuscle cells between actin filaments (F-actin) and monomeric actin (G-actin) and competition with endogenous filament capping agents; the action of cytochalasins is thought to involve prevention of G-actin polymerization by "capping" the filaments and preventing their growth (Spector et al., Cell Motil. Cytoskel. 13:127–44[1989]). However, the cytochalasins are not presently being used in therapy for several reasons, most notably corneal intolerance upon acute administration.

Ethacrynic acid is most commonly known as a loop diuretic for the treatment of edema associated with congestive heart failure and hypertension. In addition, ethacrynic acid has been tested in regards to increasing aqueous humor outflow in the eye. For example, U.S. Pat. No. 4,757,089 to Epstein, hereby incorporated by reference, describes a method of increasing aqueous humor outflow by administering ethacrynic acid, or an analog thereof, containing a chemical group capable of reacting with sulfhydryl groups in the trabecular meshwork. Though the mechanism of action was not definitively set forth, it was proposed that chemical modification of cellular membrane-protein sulfhydryl groups results in cellular or intercellular permeability to fluid flow in the aqueous humor outflow channels.

U.S. Pat. No. 5,306,731 to Epstein, hereby incorporated by reference, entails an improvement to the subject matter presented in U.S. Pat. No. 4,757,089. The improvement involves the co-administration of a "masking agent" along with the sulfhydryl-reactive moiety to improve tolerability. While both topical and intracameral formulations of an ethacrynic acid analog were involved in clinical trials, they failed due to lack of efficacy. In addition, the topical agent was corneo-toxic in monkeys. Similarly, recent studies have also shown that topically administered ethacrynic acid resulted in progressive corneal toxicity that was clinically unacceptable (Croft and Kaufman, Curr. Eye Res., 14:777–781[1995]).

Finally, research has been conducted with the calcium chelators EDTA and EGTA demonstrating breaking of C—C junctions in the trabecular meshwork and concomitant increases in outflow facility (See e.g., Bill et al., Invest. Ophthalmol. Vis. Sci., 19:492–504[1980]; and Bill, "Basic physiology of the drainage of aqueous humor," in Bito et al. eds., The Ocular and Cerebrospinal Fluids, Fogarty International Center Symposium. London: Academic Press, Exp. Eye Res. 25:291–304 (1977)]. These compounds remove calcium ions that are necessary for $Ca^{2+}$-dependent junctions, and thus function by a mechanism of action distinct from the compounds of the present invention.

Thus, the classes of agents studied thus far collectively attack only a few of the potential cellular and junctional proteins whose alteration might rearrange meshwork geometry to therapeutic advantage. Moreover, these agents are associated with adverse effects that have contributed to their presently not being commercially available.

III. Animal Model and Experimental Apparatus

A. The Animal Model

Generally speaking, the use of in vitro techniques, such as cell culture and post-mortem organ culture perfusion, has the advantage of isolating a single cell type or tissue and characterizing properties and responses free of the confounding effects of innervation, blood supply, circulating hormones, and the like. This is ideal for testing hypotheses based on specific cellular and molecular actions of compounds, and for screening candidate compounds. However, these confounding influences are an integral part of the living human system.

Thus, in order to discover unique anti-glaucoma therapies, an experimental model must be used that provides an understanding of the complex neuromuscular, vascular and biophysical systems at the whole organ level similar to the situation in the living human. Although there are some similarities, the anatomy, physiology, and pharmacological responses of the human aqueous humor formation and drainage apparatus (especially the latter) generally differ markedly from those of lower mammals. Furthermore, some of the necessary techniques are not readily adaptable to lower mammals. For example, it is virtually impossible to perform total iridectomy and ciliary muscle disinsertion via small limbal incisions in the cat or the rabbit without damaging other ocular tissues; more specifically, the iris is the cat is too thick and tough and the ciliary processes in the rabbit are located on the posterior surface of the iris. Moreover, anterior chamber perfusion in the living cat and rabbit eye gives more uncertain outflow facility values because of the tendency of the aqueous humor to clot (blood aqueous barrier breakdown) and the difficulty in the rabbit of maintaining stable anesthesia throughout a long experiment.

In contrast, the monkey is a suitable experimental animal because the biological apparati associated with aqueous humor formation and drainage closely resemble those of the human. Also, the monkey has a large accommodative amplitude, allowing technically simple, non-invasive, repeatable and reproducible assessment of ciliary muscle contractility under perturbed and non-perturbed conditions. Indeed, a previous report of the Glaucoma Panel of the National Advisory Eye Council noted the preferability of primates as opposed to sub-primate mammals for studies such as those described in this application (U.S. DHHS. Vision Research—A National Plan: 1983–87. 1987 Evaluation and Update. Report of the National Advisory Eye Council 1987; NIH Publication No. 87-2755:231–278.)

A number of different genera and species of monkeys have provided useful information regarding ocular structure and function, including the owl monkey (Aotus trivirgatus), the vervet monkey (African green; Cercopithecus ethiops), and several species of macaques (cynomolgus—M. fasicularis [formerly M. irus]; rhesus—M. mulatta; pigtail—M. nemestrina; and stumptail—M. arctoides). The cynomolgus has been used most frequently, and a large body of information has been accumulated on the functional and structural characteristics and responses of its accommodation and aqueous humor formation and drainage apparati.

B. The Apparatus

Anterior Chamber Perfusion/Outflow Facility: The apparatus for determining aqueous humor outflow facility in the living monkey eye employs the two-level constant pressure perfusion technique. The technique, infusion solution (Bárány's solution), and apparatus were originally described by Bárány and subsequently modified by others, including one of the inventors of the present invention (See, Bárány, Invest. Ophthalmol., 3(2):135–143[1964]; and Kaufman and Bárány, Invest. Ophthalmol., 15:793–807[1976]). Indeed, the basic methodology is well-described in the literature and is standard in the field (See e.g., Ménage et al., Invest. Ophthalmol Vis. Sci., 36(9):1745–1749[1995]). The experimental apparatus and the methodology of the experiments performed by the inventors is described in detail in the Experimental section, below.

Ciliary Muscle Contractility: In addition to performing experiments on live monkeys, tissue culture experiments on monkey ciliary muscle have also been performed. The inventors of the present invention developed a custom apparatus (See, Experimental section, below) in which the contractile properties of isolated monkey ciliary muscle strips, freed from their posterior attachments to the choroid/sclera and anterior attachments to the scleral spur/trabecular meshwork/cornea, can be studied in both the longitudinal contractile vector (putatively more outflow specific) and the circular contractile vector (putatively more accommodation specific) simultaneously. The apparatus represents an advance over other systems which permit measurement in only one, often undefined, vector at a time.

Although the apparatus may be utilized to identify compounds which will selectively stimulate contraction in the longitudinal vector only, and perhaps, therefore, replace the current miotic drugs (such as pilocarpine) used in the treatment for glaucoma, in the present context it serves primarily to determine whether the compounds of interest, especially those affecting actin or acto-myosin interactions or perturb C—C junctions (including those not affecting actin), inhibit ciliary muscle contractility. It is believed that physiologically, histochemically and morphologically, monkey ciliary muscle more closely resembles human ciliary muscle than does any other species.

IV. Evaluation of Compounds for Use in the Present Invention

The screening (evaluation) procedures described hereafter can be used to test compounds that might exhibit beneficial effects by altering the cytoskeleton or the C—C or C-ECM adherens junctions. Specifically, it can be used to examine compounds that might affect cell junctions through perturbation of actin filament integrity or membrane anchorage or inhibition of contractility.

Screening is first performed in cell culture. To that end, endothelial cells, cultured on glass coverslips, are exposed to different concentrations of each compound for different periods of time. Thereafter, they are fixed and either examined under the microscope directly, or immunofluorescently-labeled for actin (since actin is a central element in both C—C and C-ECM adhesions), vinculin (a central element in both types of junctions), and cadherins and catenins (critical components of C—C contact whose presence and ability to interact are essential for junction integrity), as well as other junctional molecules. Those compounds which affect junction integrity or the integrity of the microfilament system are selected for further analysis. The effective concentrations in culture also serve as guidelines for the live animal experiments.

Some of the potential classes of compounds that may be screened using this procedure are set forth in Table 1.

TABLE 1

Compound Classes

| Class of Compound | Examples | Effect |
| --- | --- | --- |
| Ser-Thr kinase inhibitors | H-7 KT-5926 ML-7 Staurosporine | Cause relaxation of acto-myosin-induced tension. Upon long exposure (≧30 minutes), the entire microfilament system deteriorates. These changes affect predominantly C-ECM adhesions. |
| Actin-disrupting drugs (macrolide compounds) | Latrunculin-A Swinholide-A | Specific and well-defined effects on actin filaments; might also affect junction integrity and consequently increase outflow facility. |
| Actin-modulating and/or stabilizing drugs (macrolide compounds) | Jasplakinolide | Effects on actin filaments; might also affect junction integrity and consequently increase outflow facility. |
| Tyrosine kinase inhibitors | Tyrphostins | These compounds, families of synthetic tyrosine kinase inhibitors with a highly diversified specificity, effect growth factor stimulation. Recent work demonstrated their capacity to selectively inhibit tyrosine phosphorylation of C-C and C-ECM adhesions. Tyrphostins may either stabilize or de-stabilize cell adhesions. |
| Protein tyrosine phosphatase inhibitors* | Sodium orthovanadate, Pervanadate, Various Vanadyl Salts | Treatment of cells with compounds enhances protein tyrosine phosphorylation by preventing dephosphorylation of tyrosyl residues. Recent studies established that the phosphorylation of tyrosyl residues on adherens junctional proteins such as catenins, paxillin, tensin, and others, may exert dramatic effects on junction integrity. |

*Hadari et al., Mol. Cell. Endocrinol., 97:9–17 (1993); and Volberg et al., EMBO J., 11:1733–1742 (1992).

Of course, it is to be understood that the present invention is not limited to the potential classes of compounds set forth in Table 1. Rather, the present invention broadly contemplates screening for compounds that may beneficially alter C—C or C-ECM adherens junctions. For example, other agents that may be screened include angiotensin II, Al-adenosine agonists, acepromazine, promazine, aceclidine, lysophosphatidic acid, genistein; endothelin-, transforming growth factor, interleukin-1, platelet activating factor, and 3α,5β-tetrahydrocortisol.

The screening procedure set forth in Table 2A can be used initially to evaluate compounds such as those presented in Table 1 that may be effective in the treatment of glaucoma. Members of the serine-threonine kinase inhibitor class of compounds are particularly effective at enhancing aqueous humor outflow in the eye, and this screen is especially appropriate for compounds in that class.

TABLE 2A

Screening Procedure

| Step | Determination | Conclusion |
| --- | --- | --- |
| I | Examine in vitro the effect of compounds on trabecular meshwork and/or aortic endothelial cells and morphology in culture. | Proceed To Step II |

TABLE 2A-continued

Screening Procedure

| Step | Determination | Conclusion |
| --- | --- | --- |
| II | Determine the effect of compounds on overall ocular tolerability/toxicity | Proceed To Step III |
| III | Determine the effect of compounds administered topically on the intraocular pressure by non-invasive measurement techniques (e.g., applanation tonometry) | Consider proceeding to Screen in Table 2B |

Compounds that have shown promise based on the screen in Table 2A can then be examined in the more comprehensive screening procedure set forth below in Table 2B.

TABLE 2B

Comprehensive Screening Procedure

| Step | Determination | Conclusion |
| --- | --- | --- |
| I | Determine compounds effectiveness on outflow facility in living monkeys | Proceed To Step II |
| II | Document whether compound is acting directly on the trabecular meshwork in living monkeys with disinserted ciliary muscle | Proceed to Step III |
| III | Perform electron microscopy to analyze the effect of the compounds on the structure of the trabecular meshwork and other tissues. | Proceed to Step IV |
| IV | Determine compounds effect on other properties, including refraction, accommodative and pupillary responses to pilocarpine; and corneal endothelial cell counts and morphology. | Consider Proceeding to Step V |
| V | Consider clinical trials on human subjects | Consider therapeutic use if compound found to be safe and effective |

As illustrated by this outline of the sequence of experimental procedures and the description of the procedures themselves (described in the Experimental section below), thoughtful consideration allows any compound to be evaluated for use with the present invention. Indeed, as described in detail in the Experimental section, these screening procedures have been employed in the experiments performed on compound H-7.

V. Potential Therapeutic Chemical Compounds

Based on work in in vitro cell culture systems, three distinct classes of compounds have been identified which have potential for facilitating aqueous humor outflow. Specifically, these classes are: A) serine-threonine (ser-thr) kinase inhibitors; B) actin-disrupting drugs; and C) tyrosine kinase inhibitors or stimulators. Representative compounds from A) and B) have been administered in vivo to the eyes of living monkeys with and without disinserted ciliary muscles, and have, indeed, increased facility at dosages comparable to their effective concentrations for altering cell shape and C—C and cell-substrate adhesion in vitro. Thus, these two classes of compounds apparently affect the trabecular meshwork such that they increase aqueous humor outflow facility.

In addition, the dose-time-response and dose-time-recovery relationships for prototype compounds in the ser-thr kinase inhibitor and actin-disrupting drug classes (i.e., categories A and B) have been established in cell culture in vitro. Moreover, the dose-facility-response relationship for compounds in those two classes has been established through testing in live animals. It has also been found that facility-effective doses of the ser-thr kinase inhibitor class interfere with pupillary but not accommodative responses to pilocarpine. This phenomenon could have important therapeutic implications. Preventing miosis allows concurrent use of pilocarpine, because pilocarpine-induced miosis in elderly patients with early cataracts is visually disabling (too little light reaches retina). Preservation of the ciliary muscle response to pilocarpine maintains the therapeutic efficacy of that compound, and also maintains the near-focusing ability of younger patients.

The work with the ser-thr kinase inhibitors and the actin-disrupting compounds in the in vitro system using bovine aortic endothelial cells in culture was predictive of the compounds' ability to affect facility in the living primate both qualitatively and quantitatively. Both of these classes of compounds, as well as representatives from each class, will be described in detail below. It should be emphasized here that the compounds discussed in this section mainly disrupt cell junctions through an effect on microfilaments and/or membrane-microfilament binding.

A. Ser-Thr Kinase Inhibitors (Affecting Myosin Light-Chain Kinase)

Several compounds known to be myosin light-chain kinase inhibitors were studied in the cynomolgus monkey eye in vivo. Data from one compound (H-7, described below) indicates that while these compounds primarily inhibit myosin light-chain kinase, thus inhibiting actomyosin-driven contractility, other mechanisms of action may also be involved. However, it is not intended that the term be limited to compounds that inhibit myosin light-chain kinase, as other targets (e.g., rho kinase) are contemplated. These compounds primarily inhibit myosin light-chain kinase, thus inhibiting actomyosin-driven contractility; upon long exposure ($\geq 30$ minutes), they cause deterioration of the entire microfilament system. In some embodiments, these changes affect predominantly C-ECM adhesions. In other embodiments, the changes include but are not limited to contractility and other cytoskeletal functions. The ser-thr inhibitors include, but are not limited to, H-7, KT-5926, ML-7, and staurosporine.

The effect of these compounds may involve loosening C—C or C-ECM junctions of trabecular meshwork cells, or altered cellular contractility via a direct or indirect effect on actin filaments, actin-myosin interactions, or actin-membrane interactions. It should be noted that there are indirect indications that the ser-thr kinase inhibitors act due to their effect on myosin light chain kinase. Such inhibition can lead to inhibition of contractility of non-muscle cells or smooth muscle, but will not affect skeletal muscle, which uses a different contractile mechanism. However, an understanding of the mechanism(s) is not necessary in order to use the present invention. In addition, it is contemplated that other compounds that find use with the present invention do not loosen C—C nor C-ECM junctions. Also, the present invention further encompasses other kinase inhibitors.

As described in the Experimental section, compounds in this class were tested to determine their effect on the isolated pilocarpine- or carbachol-precontracted rhesus monkey ciliary muscle. The muscle chamber apparatus is used to measure contractile force simultaneously in the longitudinal and circular vectors. The experimental findings regarding these agents further underscore previous structural and functional data indicating that different regions of the ciliary muscle have distinctly different properties from each other and from the iridial sphincter muscle which might be exploited to therapeutic advantage, as described above Gupta et al., Br. J. Ophthalmol., 78:555–559[1994]; and Zhang et al., Invest. Ophthalmol. Vis. Sci., 36:1645–1657 [1995]).

H-7: One specific compound tested, the myosin light-chain kinase and cyclic nucleotide-dependent protein kinase inhibitor 1-(5-isoquinolinyl-sulfonyl)-2-methylpiperazine [H-7] induced an ipsilateral increase in total outflow facility in normal and ciliary muscle-disinserted monkey eyes when perfused through the anterior chamber. In addition, H-7 inhibits ipsilateral pilocarpine-induced miosis at intracameral and intravitreal doses far lower than required for inhibition of accommodation. The methodology and results of these experiments are set forth in the Experimental section.

H-7's mechanism of action may involve modifying C-ECM adhesions of trabecular meshwork cells, and altered cellular contractility, via an effect on actin filaments or acto-myosin interactions. Indeed, H-7 has been reported to markedly increase thrombin-induced intercellular gap formation in confluent cultured bovine retinal pigment epithelial cells and induce deterioration of stress fibers in different cultured cells (Volberg et al., Cell Motil. Cytoskel., 29:321–338[1994]). Further evidence strongly suggests that H-7 acts primarily to inhibit myosin light-chain kinase and thus inhibits actomyosin-driven contractility, eventually leading to perturbation of microfilaments. Thus, it is not intended that the present invention be limited to any particular mechanism, as H-7 has various effects, including but not limited to blocking contractility. In addition, it is not intended that the present invention be limited to inhibition of myosin light-chain kinase. Indeed, the present invention encompasses additional targets. The chemical structure of H-7 is set forth in FIG. 2.

Figure 2:
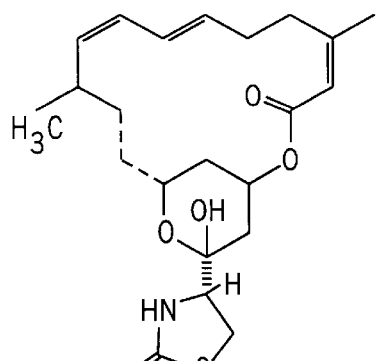
FIG. 2 depicts the chemical structures of some of the compounds of the present invention.
Figure 2:
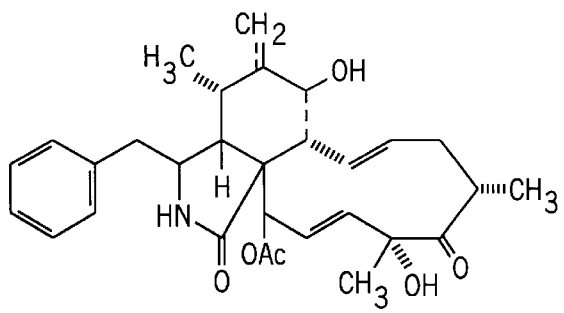
Figure 2:
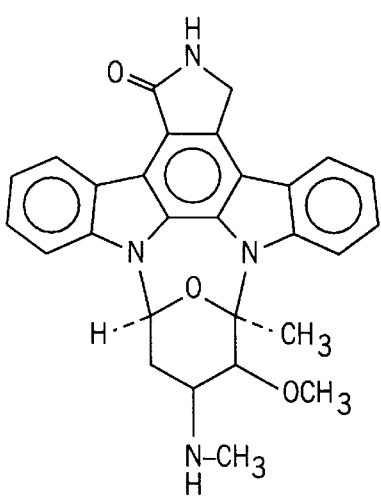
Figure 2:
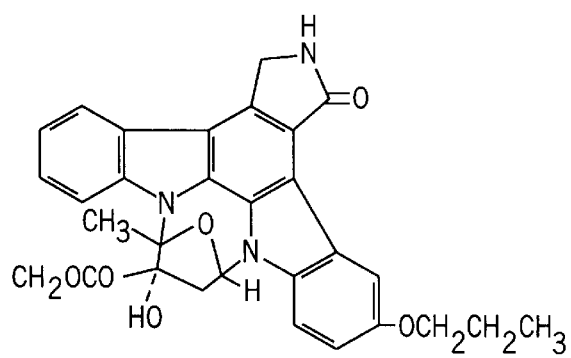
Figure 2:
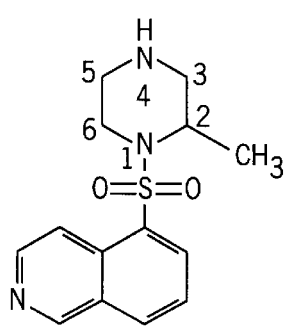
Figure 2:
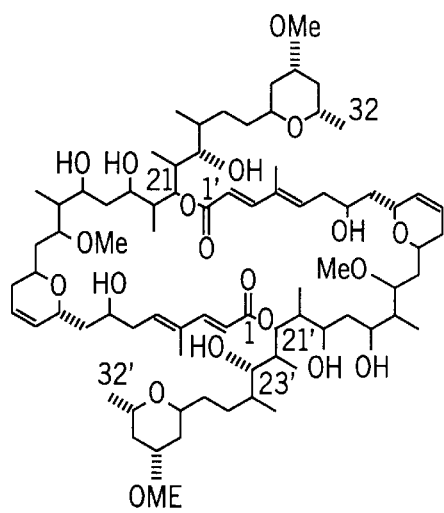

Staurosporine: Staurosporine is a microbial alkaloid produced by a Streptomyces species. The compound is known to possess several biological activities, including antifungal and hypotensive effects, inhibition of platelet aggregation, and promotion of cell differentiation (Tamaoki et al., Biochem, Biophys. Res. Commun. 135(2):397–402 (1986); Matsumoto and Sasaki, Biochem, Biophys. Res. Commun., 158(1):105–09[1989]). As described in the Experimental section, staurosporine was found to increase outflow facility when perfused through the anterior chamber. FIG. 2 depicts the chemical structure of staurosporine.

Staurosporine is a modulator of ser-thr kinases that probably, like H-7, acts through inhibition of myosin light-chain kinase. Its effect on the trabecular meshwork has not been definitively elucidated, though staurosporine might decrease contractility, leading to a total disruption of the microfilament system.

Other Candidate Compounds: Based on the positive results of the experiments with H-7 and staurosporine, other ser-thr protein kinase inhibitors are contemplated by the present invention for treatment of glaucoma, including, but not limited to, ML-7 (1-(5-iodonaphthalene-1-sulfonyl)-1H-Hexahydro-1,4-diazepine) and KT5926 [(8R*,9S*,11S*)-(−)9-hydroxy-9-methoxycarbonyl-8-methyl-14-n-propoxy-2,3,9,10-tetrahydro-8, 11-epoxy, 1H,8H, 11H-2,7b,11a-triazadibenzo[a,g]cycloocta[cde] trinden-1-one; Sigma]. It is believed that these compounds will have characteristics similar to H-7 due to their mechanisms of action (See e.g., Volberg et al., Cell Motil. Cytoskel., 29:321–338[1994]; and Nakanishi et al., Mol. Pharmacol., 37:482–488 (1990)].

ML-7: ML-7 is a myosin light chain kinase (MLCK) inhibitor commercially available from Sigma. Though not as extensively studied as some of the other protein kinase inhibitors, ML-7 has been found to effectively inhibit mouse lung carcinoma 3LL cell attachment to the fibronectin substratum (Isemura et al., Cell Bio. Int. Rep., 15(10):965–972 [1991]). In additional experiments conducted during the development of the present invention, it was shown that ML-7 increases outflow facility in living monkeys. It is contemplated that ML-7 increases outflow facility by a mechanism that is convergent with that of H-7. However, an understanding of the mechanism(s) is not necessary in order to utilize the present invention and it is not intended that the present invention be limited to any particular mechanism(s).

KT5926: KT5926 is a potent and selective inhibitor of myosin light-chain kinase. The compound has been shown to inhibit both $Ca^{2+}$/calmodulin-dependent and -independent smooth muscle myosin light chain kinases as well. Though KT5926 is deemed to be a selective inhibitor of myosin light-chain kinase, it, too inhibits other protein kinases, e.g., cAMP-dependent protein kinase, but with relatively high $K_i$ values. The chemical structure of KT5926 is depicted in FIG. 2 (Nakanishi et al., Mol. Pharmacol., 37:482–488 [1990]).

B. Actin-Disrupting Compounds Affecting Actin Integrity

Actin assembly proceeds in all cells within the eye. For example, actin assembly occurs at the ciliary muscle, where it entails formation of α-smooth muscle actin which interacts with myosin during muscle fiber contraction. In addition, actin assembly most likely occurs in all cells at the trabecular meshwork, where it entails polymerization of G-actin monomers into F-actin filaments.

Actin is an ubiquitous component of all eukaryotic cells, including the cells within the eye. It is present in both monomeric (G-) and polymerized (F-) forms. Both F-actin and G-actin may further interacts with different associated proteins, forming soluble comlexes or various superstructures such as meshworks and bundles, as well as interacting with the motor protein myosin. Interaction of actin and myosin can lead to "actomysin contraction." The well-controlled balance of G-actin and F-actin regulates the various functions of the actin cytoskeleton. The perturbation of this balance by drugs can thus affect numerous physiologicl cellular processes, such as cell motility, cell adhesion, tissue morphogenesis and adhesion-mediated signaling.

1. Latrunculins:

Latrunculins, macrolides isolated from the marine sponge *Latrunculia magnifica*, are specific and potent actin-disrupting agents that bind to monomeric G-actin, and block its polymerization, leading to the disassembly of actin filaments (Couf et al., FEBS Lett., 213:316–318[1987]; Lyubimova et al., J. Cell Biol., 65:469–478 [1997]; and Spector et al., Science 219:493–495[1983]). The two most common latrunculins, latrunculin A (LAT-A) and latrunculin B (LAT-B), cause reversible dose- and incubation time-dependent destruction of actin bundles in several types of cultured cells including HTM cells (Couf et al., supra; Lyubimova et al., supra; Spector et al., Science 219:493–495 [1983]; Spector et al., Cell Motil. Cytoskeleton 13:127–144 [1989]; Epstein et al., Invest. Ophthalmol. Vis. Sci., 40:74–81[1999]; Peterson et al., Invest. Opthamol. Vis. Sci., 40:931–941[1999]; and Cai et al., Invest. Ophthamol. Vis. Sci., 40:S505. Abstract No. 2668[1999]). As discussed in greater detail herein, LAT-B's effect on the morphology and actin organization in cultured hamster fibroblasts requires higher concentrations than LAT-A (Spector et al., Cell Motil. Cytoskeleton 13:127–144[1989]). However, the concentration required varies depending upon the assay system used. In cell culture, the high protein content of the culture medium inactivates LAT-B, leading to the requirement for higher concentrations of LAT-B. In living eyes, there is very little protein in the aqueous humor. Due to the lack of protein which inactivates LAT-B, lower concentrations of LAT-B may be used in vivo.

In living monkeys, both LAT-A and LAT-B increase outflow facility by up to 4-fold, probably by disrupting the actin cytoskeleton in TM cells, in turn relaxing the TM and separating C—C and C-ECM adherens junctions within it (Peterson et al., supra; and Peterson et al., Exp. Eye Res., 70:307–313[2000]). In addition, it is contemplated that these compounds also affect the Schlemm's canal. However, LAT-B is as effective and 10 times more potent than LAT-A (Peterson et al., [1999], supra; and Peterson et al., [2000], supra). Although an understanding of the mechanism is not necessary in order to use the present invention, it is not clear why the relative potency of the two drugs in vivo and in vitro are so different. The only structural difference between the two compounds is in the macrolide (Spector et al., Cell Motil. Cytoskeleton 13:127–144[1989]), a large apolar part of the molecule that is probably important for permeation into the cell (Spector et al., Cell Motil. Cytoskeleton 13:127–144 [1989]; and Spector et al., J. Cell Biol., 103:393a [1986]). Therefore, a pharmacokinetic mechanism may be involved (Peterson et al., [2000], supra). In addition, LAT-B is slowly inactivated by an as yet unknown serum component in cell culture medium (Spector et al., Cell Motil. Cytoskeleton 13:127–144[1989]), which is not present in the protein-poor aqueous humor or the protein-free anterior chamber (AC) perfusion medium (Peterson et al., [1999], supra).

As latrunculins increase outflow facility, it is contemplated that they will find wide use in anti-glaucoma treatment regimens. In addition, given the contrasting potency profiles of LAT-A and LAT-B in cultured cells vs the live monkey eye, it is contemplated that the present invention will also find use in the identification and/or characterization of related agents having a potent effect on IOP but less effect on the ciliary body or cornea.

Latrunculin-A is a marine macrolide that contains 16-membered rings; its structure is set forth in FIG. 2. Latrunculin-A binds monomeric G-actin in a 1:1 molar ratio, thereby shifting the equilibrium between G- and F-actin, and preventing the nucleation and elongation of actin filaments, leading to destabilization of the actin filaments. (See e.g., Spector et al., Cell Motil. & Cytoskel., 13:127–44[1989]).

Researchers have compared the short- and long-term effects of latrunculin-A on cell shape and actin organization to those of cytochalasin D. The experimental results indicated that latrunculin-A (and latrunculin B) were more potent and had significant differences on cell shape and actin organization compared to cytochalasin D. Moreover, the researchers determined that the concentration-effect relationship for latrunculin-A in vivo reflects the dissociation constant for the interaction of latrunculin-A with actin in vitro, in contrast to the situation with cytochalasin D (Spector et al., Cell Motil. & Cytoskel., 13:127–44[1989]). However, although an understanding of the mechanisms are not necessary in order to use the present invention, the mechanisms of these two drugs is very different, as cytochalasin D acts as a capping protein while latrunculins bind and sequester G-actin monomers.

In terms of latrunculin-A's efficacy as a therapeutic agent for the treatment of glaucoma, the inventors of the present invention found that, when perfused through the anterior chamber of the living cynomolgus monkey eye, latrunculin-A increases ipsilateral outflow facility (data presented in the Experimental section). The mechanism by which latrunculin-A affects outflow facility may involve inhibition of actin assembly in the trabecular meshwork cells, thus causing the cells to loosen their attachments to one another and/or to their extracellular matrix, and to change their shape, thereby enhancing outflow facility. In addition, because the ciliary muscle is a major site of α-smooth muscle actin assembly, there may also be an effect at this site, perhaps resulting in muscle relaxation and an increase in uveoscleral outflow. It is noteworthy that latrunculin-A primarily affects C—C junctions, in contrast to H-7 which mainly causes deterioration of C-ECM adhesions.

Latrunculin B (LAT-B) has similar structure and actin-disrupting activity in cultured cells to LAT-A (Coue et al., FEBS Lett., 213:316–318[1987]; Lyubimova et al., J. Cell. Biol., 65:469–478[1997]; and Spector et al., Science 219:493–495[1983]), but LAT-B's effect on the morphology and actin organization in hamster fibroblasts requires higher concentrations than LAT-A (Spector et al., Cell Motil. Cytoskeleton 13:127–144[1989]). Moreover, LAT-B, but not LAT-A, is slowly inactivated by an as yet unknown serum component, so that after 48 hours of exposure to a maximal LAT-B dose, cells completely recover, exhibiting a well-developed system of stress fibers (Spector et al., [1989], supra). In living monkeys, LAT-B has a milder effect on corneal endothelial permeability than LAT-A, and has essentially no effect on AHF (Peterson et al., Exp. Eye Res., 67(Suppl.) XIII ICER Abstracts: S.176[1998]). Thus, it is contemplated that LAT-B is "gentler" to the ocular tissues. Although LAT-B was later shown to increase outflow facility in enucleated porcine eyes (Epstein et al., Invest. Ophthalmol. Vis. Sci., 40:74–81[1999]), until the development of the present invention, it was not known if it would have the same effect in the live monkey eye.

As shown herein, LAT-B also has the ability to increase outflow facility in living monkeys, further supporting a relationship between alteration of the actin cytoskeleton in TM cells and decreased flow resistance in the conventional drainage pathway. Since the 0.2 $\mu$M intracameral dose and the 4.0 $\mu$g topical dose of LAT-B produce similar facility elevations to the 2 $\mu$M intracameral dose and the 42 $\mu$g topical dose of LAT-A, LAT-B appears to be at least 10-fold more potent than LAT-A in the live monkey TM. Additionally, the initial facility value upon restarting the perfusion immediately after AC exchange or 2 hours after topical application of maximal doses of LAT-B is substantially elevated when compared to the final baseline measurement (See, Example 10). In contrast, even maximally effective doses of LAT-A produce less initial facility increase under the same experimental conditions; only upon continued perfusion is there such a significant decrease in flow resistance.

Topical LAT-A and B significantly reduce IOP in normal monkeys, indicating that both drugs reduce resistance in the drainage pathway at normal flow rates (Kaufman et al., Exp. Eye Res., 67(Suppl. XIII ICER Abstracts):S53[1998]). However, the pressure- and flow-dependence of their facility-increasing effect indicates that the higher pressure and flow rate induced by external perfusion, as opposed to lower endogenous AHF, further destabilizes TM cell junctions and overall TM architecture to reduce flow resistance more substantially. Under this scenario, it is contemplated that such actin-disrupting agents are more effective in glaucoma patients with elevated IOP and a greater trans-trabecular pressure gradient, especially, if they are not receiving secretory suppressants. In addition, the current data suggest that the higher doses of LAT-B may render the TM architecture more unstable even at normal flow rates, so that LAT-B also might be more effective than LAT-A in normal-pressure glaucoma or in glaucoma with pressure already reduced by other agents. Moreover, the fact that the baseline facility several weeks after LAT-B is similar to that before the drug administration indicates that LAT-B, similar to LAT-A (Peterson et al., Invest. Ophthalmol. Vis. Sci., 40:931–941[1999]), induces transient alterations in cytoskeletal organization and cell adhesions rather than irreversible toxicity in the TM cells.

The results in vivo contrast to the situation in vitro, where lower doses of LAT-A produce the same maximal changes in cell morphology as higher doses of LAT-B (Spector et al., Cell Motil. Cytoskeleton 13:127–144[1989]). The only structural difference between LAT-A and LAT-B is in the macrolide (Spector et al., [1989], supra), a large apolar part of the molecule that is likely important for permeation into the cell; LAT-A has a diene moiety vs the monoene moiety of LAT-B (Spector et al., J. Cell. Biol., 103:393a (Abstract) [1986]; and Spector et al., [1989], supra). Additionally, some factor may be present in the TM cells or the AC of the living monkey that is not present in the in vitro cell types and experimental conditions previously reported, favoring LAT-B's penetration into the meshwork cells. In vitro, an unknown component in serum-containing growth medium slowly inactivates the effect of LAT-B but not LAT-A on the cytoskeleton (Spector et al., [1989], supra). However, the tight-junctioned ciliary epithelium and iridovascular endothelium largely exclude serum proteins from the aqueous humor (Krupin and Civan, in Ritch et al., (eds.), *The Glaucomas, Basic Sciences,* 2nd ed., Mosby, St. Louis, Mo., [1996], pp. 251–280). LAT-B has at most a minimal and transient effect on AC protein concentration (Peterson et al., [1998], supra), and the perfusand used in the experiments used to develop the present invention is serum-free (Bárány, supra). Therefore, LAT-B avoids inactivation in the in vivo experiments described herein. Better cellular penetration and/or reduced inactivation favor(s) more rapid attainment of higher concentrations in the TM cells of the living eye. Although an understanding of the mechanism is not necessary in order to use the present invention, it is also contemplated that the TM cells are more sensitive to LAT-B than they are to LAT-A, that the structural changes in the TM following LAT-B administration are partially different from those induced by LAT-A, and/or that some additional non-cytoskeletal action enhances LAT-B's facility effect. Again, although an understanding of the mechanisms is not necessary in order to use the present invention, it is contemplated that any or all of these factors, or other pharmacodynamic differences and/or tissue specificities, contributes to the differential potency in vivo. Regardless of the reasons, it is noteworthy from a clinical perspective, that LAT-B had less effect on AHF and corneal endothelial permeability than LAT-A in the monkey eye (Peterson et al., [1998], supra) despite having an equal or greater effect on facility. In addition, inactivation by serum makes systemic toxicity less likely for LAT-B in the event of system absorption, without diminishing the efficacy of the compound in the protein-poor anterior chamber of the eye.

As indicated herein, LAT-A and LAT-B dramatically increase outflow facility in living monkey eyes, with LAT-B producing a stronger initial facility elevation than LAT-A. In experiments conducted during the development of the present invention, it was found that both LAT-A and B significantly reduced IOP in living monkeys, consistent with their facility effects. However, the IOP reduction did not occur until 6 hours after LAT-A administration; while LAT-B reduced IOP within 1 hour. Although an understanding of the mechanism(s) is not necessary in order to use the present invention, it is hypothesized that this difference may be due to the smaller initial facility increase after LAT-A, compared to LAT-B, or to LAT-A, but not LAT-B, initially increasing AHF (as discussed further below). In addition, other unknown mechanisms also may be involved. However, as indicated above, an understanding of the mechanism(s) is not necessary in order to use the present invention.

LAT-B's effect on the morphology and actin organization in cultured hamster fibroblasts requires higher concentrations than LAT-A. In living monkeys, both LAT-A and LAT-B increase outflow facility by up to 4-fold, probably by disrupting the actin cytoskeleton in TM cells, in turn relaxing the TM and separating C—C and C-ECM adherens junctions within it. However, LAT-B is as effective and 10 times more potent than LAT-A. Although an understanding of the mechanisms is not necessary in order to use the present invention, it is not clear why the relative potency of the two drugs in vivo and in vitro are so different. The only structural difference between the two compounds is in the macrolide, a large apolar part of the molecule that is probably important for permeation into the cell. Therefore, a pharmacokinetic mechanism may be involved.

In normally hydrated human corneas, IOP measured by applanation tonometry increases with the corneal thickness (See, Ehlers et al., Acta Ophthalmol. (Copenh) 53:34–43 [1975]; and Whitacre et al., Amer. J. Ophthalmol., 115:592–596[1993]). However, applanation measurements of IOP in edematous corneas is sometimes artifactually low, due to the increased sponginess of the edematous cornea; in essence, the epithelium and stroma are applanated, rather than the entire cornea, and the measurement reflects intracorneal rather than just intraocular pressure (See e.g., Simon et al., Refract. Corneal Surg., 9:110–117[1993]). In experiments conducted during the development of the present invention, LAT-B thickened the central cornea of the live monkey eye, and presumably LAT-A would do the same. However, the LAT-A—or LAT-B—induced IOP reduction is probably not related to changes in corneal thickness, because (1) LAT-B only transiently and slightly thickened the central cornea, with the increase being ~47 $\mu$m at hour 3.5 (maximal change; only ~10% thicker compared to normal monkey cornea) or ~26 $\mu$m at hour 6 (only ~6% thicker than normal); (2) the maximal IOP reduction after LAT-B occurred at hour 6 rather than hour 3.5.

LAT-A increased the estimate of AHF by 87% during the first 3 hours after its application. However, what was calculated as increased AHF could also reflect changes in the cornea and blood-aqueous barrier that increase apparent fluorescein clearance without a true change in flow rate. Maus and Brubaker recently demonstrated an apparent increase in flow rate of 132%, without a simultaneous increase in IOP, after dilating the pupil with tropicamide and phenylephrine (Maus and Brubaker, Invest. Ophthalmol. Vis. Sci., 40:542–546[1999]). These researchers concluded that an actual increase in flow of that magnitude was unlikely and that fluorescein may have left the AC through the dilated pupil as well as through conventional outflow.

When the determination of AHF rate based on the clearance of fluorescein is made, it is assumed that the AC and cornea behave as a two-compartment system and that most of the fluorescein leaves by outflow, while a fixed amount (representing about 10% of normal daytime flow) leaves by diffusion. It is also assumed that the fluorescence measured accurately represents the mean concentration of fluorescein in the cornea and AC. It is contemplated that drugs, such as LAT-A, that change structural properties of the anterior segment could violate these assumptions by altering the route and rate of fluorescein clearance as well as the ability to measure it accurately. Thus, it cannot be determined whether the apparent increase in flow measured shortly after LAT-A administration represents a true increase in AHF, or an overestimate of flow rate, because of limitations of the model of the anterior segment and the ability to measure fluorescein in this changing environment. However, an understanding of the mechanism is not necessary in order to use the present invention. In addition, regardless of the mechanisms involved the present invention provides methods and compositions suitable for the treatment of ocular disorders, particularly those disorders associated with abnormal aqueous outflow.

Corneal endothelial cells are held together by apical and lateral junctional complexes (See, Hirsch et al., Exp. Eye Res., 23:385–397[1976]; and Ottersen and Vegge, Acta Ophthalmol., 55:69–78[1977]). The barrier function of the endothelium depends in part on the state of these junctions (See, Ota et al., Invest. Ophthalmol., 13:945–949[1974]; and Maurice, Am. J. Ophthalmol., 49:1011∫1016[196]). Cytochalasin B, a fungal metabolite, which affects the actin microfilament system by a complex mechanism (Cooper, J. Cell. Biol., 105:1473–1478[1987]; and Samath and Pollard, Biochem., 30:1973–1980[1980]), disrupts the apical microfilament network of corneal endothelial cells, causing a change in corneal endothelial morphology and increasing corneal thickness (Ota et al., supra; Kaye et al., J. Cell Biol., 61:537–543 [1974]; and Fischbarg, Exp. Eye Res., 15:615–638[1973]). After topical administration of LAT-A, corneal endothelial cell borders were transiently indistinct. This could represent disruption of C—C junctions (Kim et al., Am. J. Ophthalmol., 114:329–335[1992]). However, cell shape changes and swelling could simply reorient the cell borders so that they were no longer perpendicular to the incident light, thereby diminishing specular reflected light, and rendering the cell periphery and borders indistinct. The central surface of the swollen cells would still be perpendicular to incident light, and would appear as a bright central reflex (McDermott et al., Ophthalmol. Surg., 19:724–733 [1988]). Biomicroscopy revealed that both LAT-A and LAT-B transiently produced such innumerable small brightly refractile granule-like spots or pseudoguttata on the corneal endothelium. Nonetheless, the morphological and functional changes in the corneal endothelium induced by LAT-A and LAT-B were reversible, indicating that the cells were not lost.

Collectively, the fact that both LAT-A and B increase outflow facility and reduce IOP indicates their utility as anti-glaucoma medications. However, their effects on the cornea, ciliary body and blood-aqueous barrier present potential safety issues that practitioners should keep in mind when treating patients. LAT-B induces a stronger initial facility increase, earlier IOP reduction and smaller and less consistent changes in AHF, $k_a$ and $[Protein]_{AC}$ compared to LAT-A, suggesting that LAT-B may be a better choice, at least for some settings. The reason for these difference is not clear yet, but could be due to different sensitivities of ocular tissues to the two drugs. Nonetheless, an understanding of the mechanism(s) is not necessary in order to use the present invention.

It is also contemplated that adjustment of drug administration strategies is effective in reducing side effects. Thus, it is contemplated that administration of lower concentrations of LAT-A over a longer time will decrease outflow resistance and IOP decrease without affecting the cornea or ciliary body, in some settings. The high concentration/small volume formulations used in the topical drug protocols described herein to avoid systemic and contralateral effects in the small cynomolgus monkey place the cornea at a disadvantage. Clinically, lower concentrations in larger volumes are used, spreading the drug more evenly over the entire corneal surface and exposing the central cornea to a much lower dose. Also, it is contemplated that the use of other vehicles, delivery systems and penetration routes that are less toxic to the cornea will find use with the present invention.

2. Swinholide-A

Swinholide-A is isolated from the marine sponge *Theonella swinhoei*, and has been described as a 44-membered dilactone macrolide with a 2-fold axis of symmetry. The compound exhibits antifungal activity and has been shown to be highly cytotoxic to several cancer cell lines. Its chemical structure is set forth in FIG. 2.

Swinholide-A reportedly disrupts the actin cytoskeleton of cells grown in culture, sequesters actin dimers in vitro in both polymerizing and non-polymerizing buffers, and rapidly severs F-actin in vitro with high cooperativity (Bubb et al., J. Biol. Chem., 270:3463–3466[1995]).

In relation to its effect on outflow facility in monkeys, one of swinholide-A's primary mechanisms of action is believed to entail induction of the formation of G-actin dimers. However, an understanding of the mechanism(s) is not necessary in order to use the present invention. Indeed, it is not intended that the present invention be limited to any particular mechanism(s).

As detailed in the Experimental section, in preliminary experiments, swinholide-A did not increase facility, whether administered via bolus or exchange infusion, at the doses studied. However, the apparent ineffectiveness of swinholide-A may result from inadequate dose or exposure time. Indeed, this was determined to be the case in later experiments, as described in the Experimental section below.

3. Jasplakinolide (Jas)

Jasplakinolide (Jas), derived from the Indo-Pacific marine sponge *Jaspis johnstoni*, is a cyclic peptide with a 15-carbon macrocyclic ring that contains three amino acid residues (Crews et al., Tetrahed. Lett., 27:2797–2800[1986]; and Zabriskie et al., J. Amer. Chem. Soc., 108:3123–3124 [1986]). This compound has fungicidal and antiproliferative activities that are similar to swinholide-A. Jas is also a potent inducer of actin polymerization in rabbit skeletal muscle actin (Bubb et al., J. Biol. Chem., 269:14869–14871[1994]), and is believed to stabilize actin filaments by binding F-actin (e.g., similarly to phalloidin, a peptide isolated from the mushroom *Amanita phalloides*). Chemically, the 15-carbon macrocyclic ring of Jas bears little resemblance to that of phalloidin. However, phalloidin and Jas have similar affinities for F-actin and Jas appears to be more effective in stabilizing filaments (Bubb et al., [1994]).

4. Cytochalasins

The fungal metabolites cytochalasin B and D inhibit actin filament elongation and promote actin filament nucleation, resulting in a decrease in average filament length, although the fraction of F-actin may remain constant or even increase. This decrease in length (but not net actin depolymerization) is likely responsible for the effects of cytochalasins on the actin cytoskeleton structure and cell morphology. In living monkeys and enucleated porcine eyes, these cell changes have been considered to be related to the drug-induced decrease of outflow resistance across the trabecular meshwork and Schlemm's canal (Peterson et al., Invest. Ophthalmol. Vis. Sci., 40:931–941 [1999]; Peterson et al., Exp. Eye Res., Exp. Eye Res., 70:307–313[2000]; Peterson et al., Invest. Ophthalmol. Vis. Sci., 41:1749–1758[2000]; Kaufman et al., Invest. Ophthalmol. Vis. Sci., 23:646–650[1982]; and Epstein et al., Invest. Ophthalmol. Vis. Sci., 40:74–81 [1999]). On possible explanation of the incomplete inhibition of cytochalasin B's activity by phalloidin is phalloidin's poor cellular penetration (Robinson and Kaufman, Arch. Ophthalmol., 112:1610–1613[1994]). As Jas is reportedly more potent at stabilizing actin filaments and has better cell membrane penetration than phalloidin, it was thought that Jas might be a useful agent for use in increasing outflow facility. However, an understanding of the mechanism(s) involved is not necessary in order to utilize the present invention. Indeed, it is not intended that the present invention be limited to any particular mechanism(s) of action.

As discussed in greater detail in Example 12, in 80 to 90 minute post-drug perfusions, 10, 100 and 500 nM Jas had no significant effect on outflow facility. In addition, the effect of a facility-inefficient dose of Jas plus an effective or submaximal facility-increasing dose of latrunculin B were also determined. In these experiments, it was determined that 2.5 $\mu$M Jas significantly increased outflow facility by 157±57% (adjusted for baseline and resistance washout in contralateral control eyes). However, it was also determined that the increase in outflow facility in the 500 nM Jas plus 60 or 200 $\mu$M latrunculin B-treated eye was similar to that observed with an eye treated only with 60 or 200 nM latrunculin B.

C. Tyrosine Kinase Inhibitors or Stimulators

The third class of chemical entities which is contemplated, based on work in in vitro cell culture systems, for facilitating aqueous humor outflow includes the tyrosine kinase inhibitors or stimulators.

The tyrphostins represent one family of tyrosine kinase inhibitors. These compounds, synthetic tyrosine kinase inhibitors with a highly diversified specificity, effect growth factor stimulation. Studies have demonstrated their capacity to selectively inhibit tyrosine phosphorylation of junctional (C—C and/or C-ECM) proteins. Tyrphostins may either stabilize or de-stabilize cell adhesions (See, Volberg et al., EMBO J., 11:1733–1742[1992]; and Volberg et al., Cell Regul., 2:105–120[1991]).

VI. Composition and Administration of Compounds

As indicated above, the present invention contemplates using therapeutic compositions of agents that mainly disrupt cell junctions through an effect on microfilaments and/or membrane-microfilament binding in the ocular fluid drainage pathways to reduce intraocular pressure. It is not intended that the present invention be limited by the particular nature of the therapeutic preparation. For example, such compositions can be provided together with physiologically tolerable liquid (e.g., saline), gel or solid carriers or vehicles, diluents, adjuvants and excipients, such as pharmaceutical grades of mannitol, lactose, starch, magnesium stearate, sodium saccharin, cellulose, magnesium carbonate, and the like. These compositions typically contain 1%-95% of active ingredient, preferably 2%-70%.

These therapeutic preparations can be administered to mammals for veterinary use, such as with domestic animals, and clinical use in humans in a manner similar to other therapeutic agents. In general, the dosage required for therapeutic efficacy will vary according to the type of use and mode of administration, as well as the particularized requirements of individual hosts.

The therapeutic compositions contemplated by the present invention may be mixed with diluents or excipients which are physiologically tolerable and compatible. Suitable diluents and excipients are, for example, water, saline, dextrose, glycerol, or the like, and combinations thereof. In addition, if desired the compositions may contain minor amounts of auxiliary substances such as wetting or emulsifying agents, stabilizing or pH buffering agents or preservatives.

For topical administration, the compounds of the present invention are generally dissolved or suspended in a carrier like physiological saline (e.g., 0.9%) or methyl cellulose (e.g., 3%). The high viscosity of a compound like methyl cellulose allows for increased contact time between the eye and the corneal surface, thereby allowing increased corneal penetration. Similarly, a compound like benzalkonium chloride (e.g., 0.025%) that disrupts the corneal membrane can also be used to facilitate corneal penetration.

As alluded to in the preceding paragraph, the preferred mode of administration for these compounds entails a solution or suspension that can be administered as an eyedrop. In addition, infrequent intracameral administration could be feasible if done infrequently (e.g., once yearly) or for acute post-surgical situations. Of course, the therapeutic compounds may be investigated for their efficacy via other routes of administration, including oral, intravenous, intramuscular, and injection into the collector channels of Schlemm's canal itself.

Because some data has indicated that the compounds have a long duration of action, they may be effective at a dosing interval greater than that of currently available agents. Less frequent administration may be required if extracellular matrix material takes some time to re-accumulate in the ocular fluid drainage pathway following drug-induced washout of extracellular material.

Experimental

The following examples serve to illustrate certain preferred embodiments and aspects of the present invention and are not to be construed as limiting the scope thereof.

In the experimental disclosure which follows, the following abbreviations apply: mm (millimeters); Hg. (mercury); eq (equivalents); M (Molar); mM (millimolar); $\mu$M (micromolar); mmol (millimoles); plmol (micromoles); nmol (nanomoles); g (grams); mg (milligrams); $\mu$g (micrograms); kg (kilograms); L (liters); mL or ml (milliliters); $\mu$L or $\mu$l (microliters); cm (centimeters); mm (millimeters); $\mu$m (micrometers); nm (nanometers); mA (milli-amperes); min. (minutes); ° C. (degrees Centigrade); $Ca^{2+}$ (calcium ion); IV (intravenous); IM (intramuscular); SQ (subcutaneous); QD (daily); BID (twice daily); TID (three times daily); QID (four times daily); AIDS (acquired immune deficiency syndrome); SAIDS (simian acquired immune deficiency syndrome); C—C (cell-cell); C-ECM (cell-extracellular matrix); MLCK (myosin light chain kinase); AVMA (American Veterinary Medical Association); American Optical (Scientific Instrument Div., Buffalo, N.Y.); Coherent/Ocumetrics, (Coherent/Ocumetrics, Palo Alto/Mountain View, Calif.); Bausch and Lomb (Bausch and Lomb, Inc., Rochester, N.Y.); DGH Technology (DGH Technology, Inc., Solana Beach, Calif.); B. Braun Melsungen AG (Germany); Calbiochem (San Diego, Calif.); Calbiochem-Novabiochem (La Jolla, Calif.); Alcon (Alcon, Ft. Worth, Tex.); Borden (Borden, Inc., Columbus, Ohio); Haag-Streit (Carl Zeiss, Thornwood, N.Y.); Hamilton Co. (Reno, Nev.); Harvard Apparatus Co., Inc. (South Natick); Keeler (Keeler Instruments, Inc., Broomall, Pa.); Kipp & Zonen (Bohemia, N.Y.); Norma Goertz Instruments (Elk Grove Village, Ill.); Seiler (Seiler Instrument Co., St. Louis, Mo.); Sigma (Sigma Chemical Company, St. Louis, Mo.);

Statham (Ording Inc., Houston, Tex.); Alexa (Alexa Corporation, San Diego, Calif.); Tri-Point Medical L. P. (Raleigh, N.C.); SD (standard deviations); FDA (United States Food and Drug Administration); USP (United States Pharmacopeia); DMSO (dimethyl sulfoxide); DMEM (Dulbecco's Modified Eagle's Medium); MES (2-[N-morpholino]ethanesulfonic acid); s.e.m. (standard error of the mean); df (degrees of freedom).

Unless otherwise indicated, the examples that follow utilized the procedures and experimental animals described hereafter.

1. The Experimental Animals and the Animal Model

Absent definitive statements to the contrary, the procedures were performed on adolescent or young adult cynomolgus (*Macaca fascicularis*) or rhesus (*Macaca mulatta*) monkeys. Though both sexes were tested, female monkeys weighing 2–12 kg were primarily used. Rhesus monkeys were used for selective procedures only. Specifically, rhesus monkeys were used in (i) the ciliary muscle disinsertion protocols (which encompassed both rhesus and cynomolgus monkeys) and in (ii) the in vitro muscle contraction experiments (which encompassed rhesus monkeys almost, if not entirely, exclusively). It should be noted that, in order to minimize the risk of infection, cynomolgus and rhesus monkeys are rarely physically together in the laboratory (i.e., they are infrequently anesthetized in the same room).

In order to avoid the possibility of corneal decompensation, the number of anterior chamber cannulations the eyes underwent was limited. Rhesus monkey eyes had up to 8 perfusions, most of which were 2-needle. With cynomolgus monkeys, animals with less than five perfusions were chosen for the topical drop and perfusion experiments (though some animals not used in these experiments have had up to 20 perfusions). It should be noted that cynomolgus monkey eyes will usually tolerate 10 or more invasions before experiencing corneal decompensation. Although less experimental data are available for the rhesus as compared to the cynomolgus monkey aqueous formation and drainage apparati, enough data is known about each model to be confident that they are both representative of human physiology. The reason for using both rhesus and cynomolgus monkeys in the experiments relating to the present invention was to ensure that enough experimental animals would be available.

Empirically, it was found that approximately 8–10 experiments are required for any drug dose in order to obtain a reliable quantitative, statistically testable estimate of the response. Formal sample size calculations have corroborated this impression, as hereafter described. Generally speaking, the inventors wished to identify mean physiologic responses that were >25% of the baseline value (adjusted for non-drug or non-stimulus-related baseline drift) and >1.5 SD of the mean response. The following standard equation for sample size calculation was used: $N=2\ (Z\alpha+Z\beta)^2/(\Delta/\sigma)^2$, where $Z\alpha=1.645$ or $1.960$ for one-sided and two-sided 5% significance, respectively; $Z\beta=0.84$ or $1.282$ for 80% and 90% power, respectively; $\Delta$=population standard deviation; $\sigma$=the difference (i.e., response) in the parameter being measured ($\Delta$ and $\sigma$ must have the same units). From that equation, it was determined that 5.5 experiments were required to detect differences of 1.5 standard deviations in a paired test at a one-sided 5% significance level with 80% power, while 9.3 experiments were needed to detect such a difference at a two-sided 5% significance level with 90% power.

Some of the experimental animals were donated by or purchased from Corning Hazelton Laboratories (Madison, Wis.) or from the Wisconsin Regional Primate Research Center (Madison, Wis.). Other experimental animals were obtained from one of the inventor's breeding colony. The animals were used repeatedly until humanitarian considerations or loss of suitability required their sacrifice. The animals were used in the following experiments:

a) A group of approximately thirty surgically untouched animals underwent anterior chamber perfusion to work out drug dose-facility response relationships and/or drug interactions.

b) A group of approximately twelve monkeys underwent unilateral or bilateral ciliary muscle disinsertion. This group then underwent intracameral drug treatment/anterior chamber perfusion to assess drug effects on outflow facility independent of the drugs' effects on ciliary muscle tone. Non-invasive experiments were conducted up to twice weekly, depending on the type and duration of anesthesia; long-duration deep anesthesia experiments were neither performed on an animal more than once weekly nor for too many consecutive weeks. Invasive experiments were performed at four-to-six week intervals (whether the animal was ciliary muscle-disinserted or not) and only when the anterior chambers have no cells or flare at slit-lamp examination by a trained ophthalmologist.

Regarding care of the experimental animals, the animals were neither chained nor otherwise chronically restrained. In general, post-surgical analgesic medications were not employed for relatively minor surgical procedures (e.g., iridectomy, perfusions, tail cut-downs); the rationale was to allow recovery to be judged in the undrugged animal. Post-surgically, the animals were isolated in a recovery cage warmed with a heat lamp, given food and water ad libitum, and observed at least once daily by both a veterinarian or caretaker staff and one of the inventors or a project specialist staff. Following major procedures (e.g., ciliary muscle disinsertion), post-surgical analgesic medication (butorphanol 0.2–0.3 mg/kg SQ BID) was administered and the animals received intramuscular antibiotics (procaine penicillin G+dihydrostreptomycin sulfate; Pfizer, N.Y.) and glucocorticosteroids (methylprednisolone acetate; UpJohn, Kalamazoo, Mich.) daily for varying lengths of time.

When monkeys are having significant discomfort, they exhibit certain easily detectable behavior traits, including decreased activity, holding their heads, decreased responsiveness to human presence and other external stimuli, diminished interest in food and water. Any animal behaving in that manner was anesthetized with ketamine (dosing parameters described below) and carefully examined to determine the cause. Based upon the inventors' personal experience, something is usually wrong (e.g., infection, overwhelming inflammation) with an animal behaving in such a manner so as to make the animal experimentally valueless and therapy difficult and protracted. Therefore, such animals are immediately euthanized in conjunction with the protocols of other investigators to spare them suffering (the details on euthanasia are set forth below).

2. Administration of Anesthesia and Euthanasia

Several different anesthesia protocols were performed depending on the procedures being utilized or the length thereof. The protocols may be summarized as follows:

a) For experiments or procedures lasting less than 1 hour (e.g., iridectomy, suture removal, slit lamp examination, and photography), the following agents were administered: IM ketamine 10 mg/kg+IM diazepam 1 mg/kg or acepromazine 1 mg/kg.

b) For experiments or procedures lasting more than 1 hour (e.g., ciliary muscle disinsertion, anterior chamber perfusion, refraction with drugs), the following agents were administered: IM ketamine 10 mg/kg or IM methohexital-sodium 15 mg/kg in conjunction with IM pentobarbital-sodium 35 mg/kg. For especially long experiments (i.e., experiments exceeding approximately 3–4 hours), hourly supplemental IM pentobarbital doses of 10 mg/kg were usually required after the first 2–3 hours.

c) For euthanasia, the following agents were administered: IM ketamine 10 mg/kg+IM/IV pentobarbital overdose. The absence of a heart beat was confirmed in a manner consistent with recommendations of the AVMA Panel of Euthanasia.

3. Surgical Procedure

The methods of iris removal (limbal incision) and ciliary muscle disinsertion (goniotomy-like approach) are well known and have been described in detail elsewhere (See e.g., Kaufman and Luiten-Drecoll, Invest. Ophthalmol., 14:766–771[1975]; and Kaufman and Bárány, Invest. Ophthahnol., 15:793–807[1976]). Those well-known procedures were followed in the experiments of this invention. Ciliary muscle disinsertion was verified gonioscopically, physiologically (i.e., through loss of accommodative and outflow facility responses to pilocarpine), and, in some eyes, histologically.

4. Drug Delivery a) Topical: Eye drops were applied to the anesthetized monkeys as previously described.

b) Transcorneal: A 30 gauge needle was removed from its hub, connected directly to narrow-bore polyethylene tubing, and threaded through the cornea for several millimeters using a needle driver. The beveled tip of the needle was then pushed into the anterior chamber and drug was administered. The volume of solution delivered did not exceed 20 $\mu$l. The needle was then withdrawn from the anterior chamber without any loss of aqueous humor.

c) Intravitreal: A 27–30 gauge needle, prepared as above, was inserted directly into the vitreous through the pars plana at either the 10:00 or 2:00 positions. The total volume injected did not exceed 50 $\mu$l.

d) Systemic: Drug was administered via IM or IV injection. Alternatively, a venous or arterial line of polyethylene tubing was placed in the monkey's tail following a small incision and isolation of the vessel (See e.g., Gabelt and Kaufman, Exp. Eye Res., 49:389–402 [1989]).

5. Cell Culture

To evaluate the junction- and cytoskeleton-disrupting potential of the various drugs, monolayers of cultured bovine aortic endothelial cells, as well as a variety of other cells (e.g., human TM cells) were used. These cells form, in culture, a continuous monolayer with well-developed intercellular junctions, extensive adhesion to the underlying matrix and a well-developed network of actin microfilaments. The integrity of the monolayer can be determined by light- and electron-microscopy, and the organization of the actin cytoskeleton by fluorescent labeling with fluorophore-conjugated phalloidin.

These cells were selected because they are related to the trabecular meshwork cells which line the outflow system and because they were found to be very sensitive indicators for junction integrity. However, it is not intended that the present invention be limited to the particular cells used in the Examples described herein. Indeed, it is contemplated that various cells will find use with the present invention.

The cells were plated at half confluency on clean glass coverslips and cultured in complete medium for 2–4 days until they reached confluency. The drug was then added to the culture medium for different periods of time, after which the cells were either fixed with a fixative appropriate for the specific antigen being examined or further incubated in a drug-free medium to examine recovery. Fixed or fixed-permeabilized cells were then either fluorescently labelled for actin using a fluorescein- or rhodamine-conjugated phalloidin or immunofluorescently labelled for the different cytoskeletal or junctional proteins.

Immunofluorescence microscopy and transmitted light microscopy were conducted, and the integrity of the microfilament system in control- and drug-treated cells was then compared visually. At the resolution of the light microscope used (Axiophot, Zeiss Oberkochen, Germany), intact junctions usually appeared as a single actin, vinculin-catenin-, and cadherin-rich "line." Disruption of the junctions led to disappearance of this line or its apparent division or "splitting" into two lines due to the dissociation of the junction. A digital microscopic system (Kam et al., J. Cell Sci., 108:1051–1062[1995]) was used for quantitative analyses, morphometry and 3-dimensional reconstruction.

6. Anterior Chamber Perfusion/Outflow Facility

As previously indicated, the apparatus for determining aqueous humor outflow facility in the living monkey eye employs the two-level constant pressure perfusion technique. This technique, and variations thereof, are well known in the art (See Bárány, Invest. Ophthalmol., 3(2): 135–143[1964]; and Kaufman and Bárány, Invest. Ophthalmol., 15:793–807[1976]).

Figure 3:
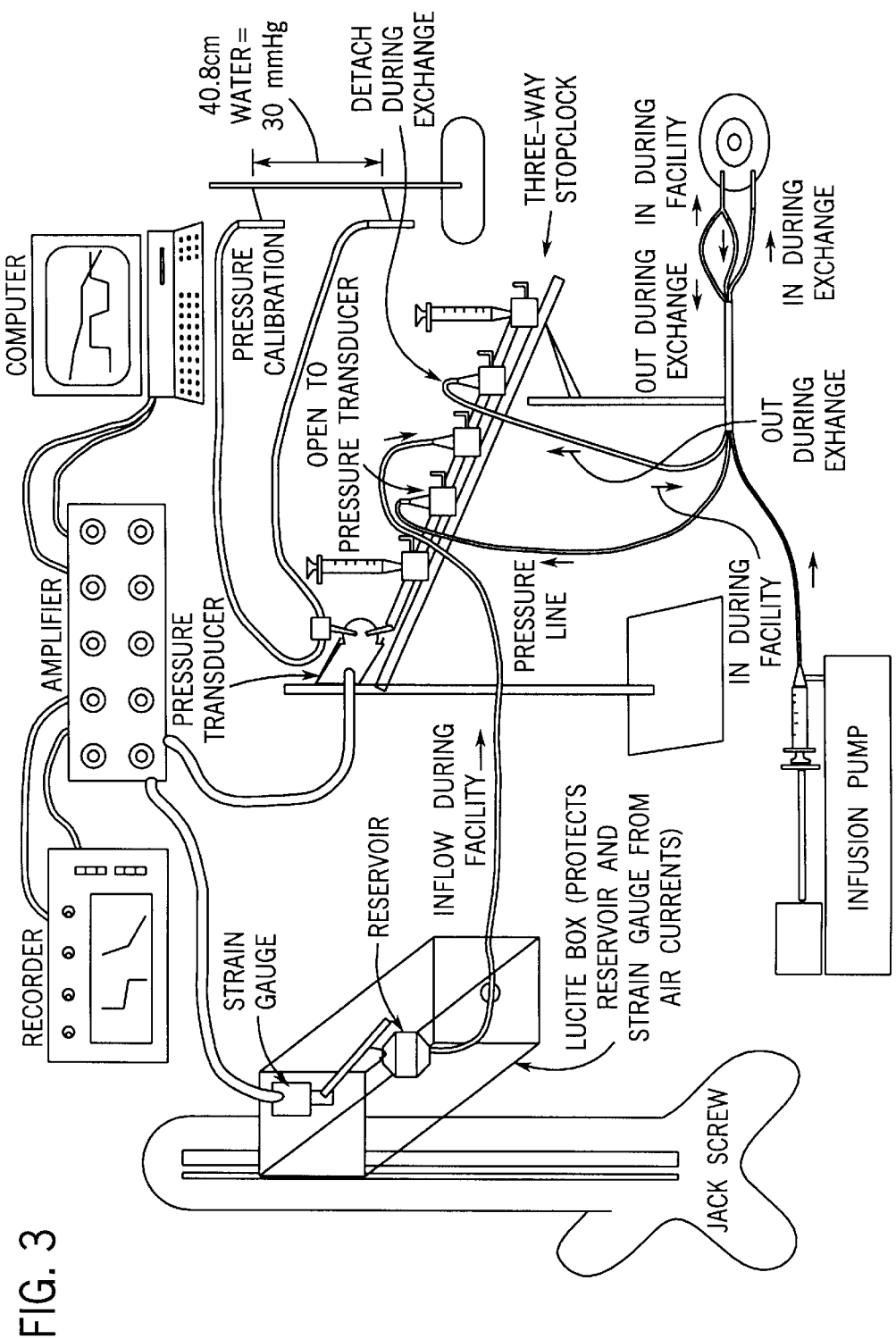
FIG. 3 is a schematic drawing of the anterior chamber perfusion set-up used in conjunction with some of the experiments.

FIG. 3 schematically illustrates the present apparatus as used for one eye. Two identical set-ups are used when studying two eyes of an animal simultaneously, as in the data presented hereafter. However, only one computer (Apple Macintosh II with National Instruments NB MIO-16 data acquisition board running perfusion program written by David Schuh using Labview for Macintosh, National Instruments, Austin, Tex.), amplifier and recorder (Soltec Corp. 4-channel recorder models 3314 and 6400, San Fernando; Linseis 4-channel recorder model 2045, Princeton Junction) are needed; they handle the input from both eyes simultaneously. The major components of the apparatus include customized 26-gauge needles and polyethylene tubing which connect the anterior chamber of the eye to a continuously-weighed fluid reservoir (Harvard Precision Adjustable Screw Stand (modified with motor and microswitches to raise and lower the reservoir), Harvard Apparatus Co., Inc., South Natick), the change in weight with time providing a measurement of flow. Other major components include a pressure transducer (Statham Universal Transducer P23XL; Ording Inc., Houston, Tex.), strain gauges (Statham Universal Transducing Cell GM2/GM3 with Microscale Accessory; Ording Inc.) and an infusion system via a series of two- and three-way stopcocks (HV3-2 and HV3-2; Hamilton Co., Reno). The infusion system allows regulation and measurement of intraocular pressure and rate of fluid flow from the reservoir and infusion syringe into the eye and calculation of outflow facility from those measurements (See e.g., Ménage et al. Invest. Ophthalmol. Vis. Sci., 36(9):1745–1749 [1995]). The flow and pressure data are calculated from the electronic signals provided by the pressure transducer and strain gauge, the signal processing and calculations being performed on-line in real-time by the amplifier and computer, according to the inventors' own software. The recorder simply provides a back-up record of the flow and pressure data, from which the facility can be calculated off-line, should the computer fail.

In a typical experiment, the anterior chamber of each eye was cannulated transcorneally with one branched and one unbranched needle, and connected to the apparatus as described above. The exchange needles were inserted with the branched needle superior to the single needle and separated by several mm, and the opposite ends of the needles were attached to perfusand-filled tubing through which drug, vehicle, and perfusion solutions could pass into the eye. Anterior chamber exchange was accomplished by attaching the tubing of the single needle to a syringe on a pump. One tubing arm of the branched needle was detached from the reservoir of the perfusion apparatus and fixed at an intraocular pressure so that fluid could exit the eye without changing the intraocular pressure.

Baseline outflow facility measurements were taken for 35–45 minutes, after which the previously-clamped tubing from the unbranched needle was connected to syringes containing drug for one eye and vehicle for the opposite eye via customized cone-tipped needles, and unclamped. The syringes were placed in a Harvard Apparatus (Harvard pump model 944) variable-speed infusion pump. One tubing arm of the branched needle was detached from the reservoir of the perfusion apparatus and fixed at an elevated position so that fluid could exit the eye without changing intraocular pressure.

The inflow tubing was disconnected and the pump turned on to inflow at a rate that allowed 2 ml of drug/vehicle solution to pass through the anterior chamber in a 10–15 minute period via the single needle; the solution then exited the eye via the detached arm of the branched needle. During this period, the reservoirs were emptied and filled with the same solution that was infused into that eye. Following the exchange, the inflow line was reconnected to the reservoir of the perfusion apparatus and the tubing from the infusion syringes was clamped.

Facility measurements were taken for ninety minutes beginning either immediately, or after a waiting period of up to 90 minutes during which the infusion line from the reservoir was clamped. The content of the solutions in the syringes and reservoirs and the number and temporal spacing of infusions varied with the protocol. For example, (i) in a reversibility experiment, there was a second infusion after the post-first infusion measurement, in which both eyes received vehicle without active drug, and (ii) in monkeys with ciliary muscle disinsertion in one eye, both eyes received active drug after the baseline measurements. In all cases, facility was calculated by the method of successive weighted averaging.

7. The Muscle Chamber

Thus far, only H-7 has been tested in the muscle chamber. The muscle chamber will be used for additional compounds that show effectiveness on facility in vivo, and especially if they affect accommodative responses to pilocarpine in vivo. A description of the set-up and methodology follows hereafter.

The muscle chamber and the protocol for rhesus monkey tissue collection, ciliary muscle dissection and chamber mounting have been described in detail elsewhere (See e.g., Poyer et al., Curr. Eye Res., 12(5):413–422[1993]; and Poyer et al., Invest. Ophth. Vis. Sci., 36:2461–2465[1995]). Briefly, globes were enucleated from rhesus monkeys (*Macaca mulatta*) aged 6 to 18 years under deep pentobarbital anesthesia (25 mg/kg IV) just prior to or within 5 minutes of euthanization and placed in a cell culture medium (Medium 199 with added penicillin G/streptomycin (50 units/ml) and 10% fetal bovine serum; all from Sigma) at 4° C. The ciliary muscle was then dissected under a surgical microscope (Zeiss OP-MI 6), yielding a section of muscle approximately 4 cm circular×4 mm meridional and including the entire anterior-posterior extent of the ciliary muscle from the scleral spur to the ora serrata. A 5 mm circular×4 mm meridional strip was then cut from the section, secured to four acrylic attachment rods with cyanoacrylate adhesive (Tri-Point Medical and B. Braun Melsungen AG) and mounted in the apparatus.

Figure 4:
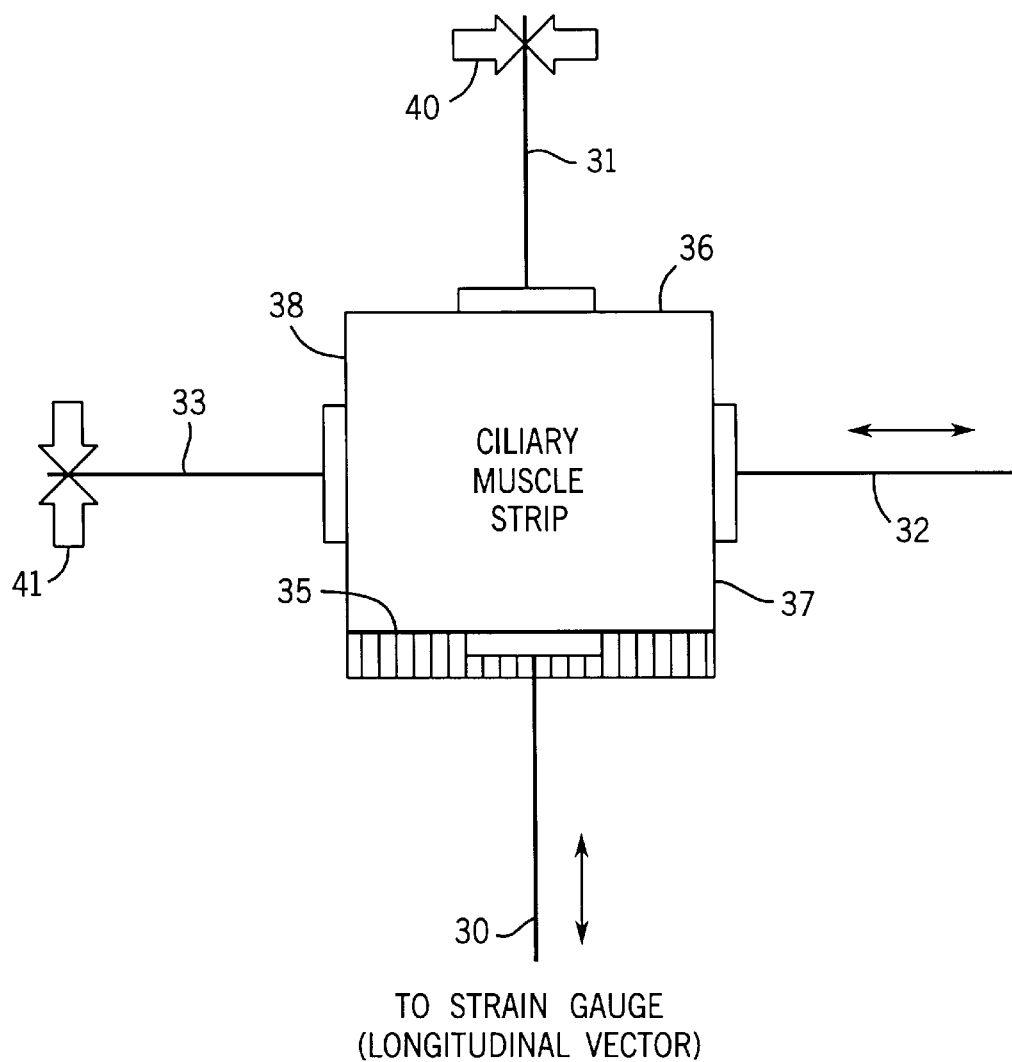
FIG. 4 is a schematic diagram showing the attachment of a ciliary muscle strip to strain gauges in the muscle chamber apparatus. The muscle chamber apparatus is used to measure contractile force simultaneously in the longitudinal and circular vectors.

FIG. 4 is a schematic diagram showing the attachment of a ciliary muscle strip to strain gauges in the muscle chamber apparatus. The muscle chamber apparatus is used to measure contractile force simultaneously in the longitudinal and circular vectors. Referring to FIG. 4, the first acrylic attachment rod 30 was positioned at the cut anterior end of the muscle 55 analogous to the scleral spur/trabecular meshwork; the second acrylic attachment rod 31 was positioned at the cut posterior end of the muscle analogous to the ora serrata 36. The first rod was connected to a first strain gauge (not shown) via a drop of paraffin wax, while the second, opposing rod, was clamped in position in the apparatus; the position of the clamp is depicted by the solid arrows 40. Force registered from the first strain gauge was represented primarily in the longitudinal (putatively more outflow-specific) vector of ciliary muscle contraction.

The third acrylic attachment rod 32 was positioned at the medial cut edge of the muscle 37 and was connected to a second strain gauge (not shown), while the fourth acrylic attachment rod 33 was clamped in position at the opposite lateral cut muscle edge 38; the position of the clamp is depicted by the solid arrows 41. The second strain gauge thus registered force representing primarily the circular (putatively more accommodation-specific) vector of ciliary muscle contraction. The remainder of the original muscle section is stored in culture medium (Medium 199; Sigma) at 4° C. for future use.

The muscle chamber was maintained at 34° C. and perfused continuously with warmed oxygenated Krebs solution (prepared by the inventors: ionic composition (mM): $Na^+$ 143.3, $K^+$ 5.9, $Ca^{+2}$ 2.6, $Mg^{+2}$ 1.2, $Cl^-$ 128.3, $H_2PO_4^{-2}$ 2.2, $HCO_3^-$ 24.9, $SO_4^-$ 2 1.2, glucose 11.1, pH 7.4, continuously oxygenated with 95% $O_2$/5% $CO_2$) or Krebs solution containing drug. As alluded to above, the first and third attachment rods were secured via paraffin to two strain gauges (force transducers); the strain gauges were mounted on micropositioners for precise control of muscle resting tension. Muscle strip dimensions were measured by the use of dividers and Vernier calipers prior to and immediately following mounting in the muscle chamber. The original strip dimensions, reestablished in the muscle chamber, determined the muscle's resting tension (which ranged from 100 to 200 mg in both muscle vectors). Output from both strain gauges was recorded on a 2-channel flatbed recorder (Kipp & Zonen (model BD112) and Norma Goertz Instruments (model Servoger 124)).

A muscle strip was mounted in the muscle chamber beginning 1 hour after enucleation, used for 2 to 3 hours, and replaced by new strips (stored at 4° C. until use) successively over the next 8 to 10 hours. Muscle strips were also used on the day following enucleation, having been kept in the cell culture medium at 4° C. overnight.

In this system, the muscarinic agonist carbachol induced reproducible dose-dependent, atropine-inhibitable contractions in both vectors, with essentially super-imposable dose-response curves (data not shown). The responses were reproducible for the 2–3 hours use of fresh, same-day-stored and overnight-stored strips.

After a ciliary muscle strip has been equilibrated, increasing concentrations of the experimental compound dissolved in perfusand (Krebs solution) were perfused through the ciliary muscle chamber to establish a concentration-response curve. Different protocols were followed for compounds which mediate ciliary muscle contraction and for compounds which mediate ciliary muscle relaxation. For compounds which mediate ciliary muscle contraction, following equilibration of a ciliary muscle strip with plain Krebs solution, the strip was exposed to each successive concentration of test compound for a period of 15 minutes, followed by a further 15 minute period of exposure to plain Krebs solution once again, followed by the next concentration of test compound for 15 minutes, etc. The 15 minute period was used based on the inventors' experience that it is the minimum time necessary for establishment of a full drug effect or reversal of a drug effect.

For compounds which mediate ciliary muscle relaxation, after equilibration, each ciliary muscle strip was exposed to Krebs solution incorporating pilocarpine (10 μM) or carbachol (1 μm) concentrations of these cholinergic agonists known to mediate "just-maximal" contraction of the in vitro ciliary muscle in both contractile vectors. After 15 minutes of such exposure, the strips were then exposed to Krebs solution incorporating both a just-maximal concentration of cholinergic agent plus increasing concentrations of test compound (15 minutes at each concentration) until a reversal of some cholinergic-induced tone was seen. Thereafter, higher concentrations of test compound were utilized until a maximal reversal was seen. For compounds which mediate ciliary muscle relaxation, there was no 15 minute period between delivery of test compound at each concentration. However, at the conclusion of the test compound investigation, the strip was given a further 15 minute perfusion with Krebs solution incorporating the cholinergic agent for the purpose of testing the ability of the strip to recontract. Finally, perfusion with plain Krebs solution was used to establish the ability of the tissue to relax once again.

Starting concentrations of each test compound were determined from reports in the literature regarding the compound's effects on ciliary muscle contractility, accommodation, outflow facility and other biological parameters. In addition, starting concentrations were also influenced by in vivo monkey studies performed in the inventors' laboratories.

8. Other Experimental Procedures, Equipment, and Reagents a) Tissue Culture Facilities: Tissue culture room contains two BioFlo laminar hoods, four $CO_2$ incubators, and a full set of accessory tools.

b) Microscopy: Two units were available for light microscopy. The first unit is equipped for live-specimen recording, with one upright and one inverted microscope, with temperature-controlled tables, video recording devices, videotape and video disc recorders and a semiautomatic microinjection system. The second unit consists of a digital microscopic system, with several light microscopes including a confocal microscope, and a computerized image reconstruction facility. The electron microscopic unit contains three transmission electron microscopes (Philips EM400, TECHNAI12, CM12) and two scanning electron microscopes (Philips 515, Jeol 6400) and is fully equipped for sample preparation.

c) Refraction/Accommodation: Refraction and Accommodation were measured with a Hartinger coincidence refractometer (Jena Hartinger model 602520-01220; Seiler).

d) Cell Counts and Morphology: Corneal endothelial cell counts and morphology were determined for H-7 by specular microphotography (Wide Field Specular Microscope fitted with an Olympus OM1 35 mm camera; U.S. Pat. No. 4,170,398, hereby incorporated by reference) using black and white negative film (Kodak TMY 400 ASA). Animals were anesthetized with ketamine alone or ketamine and acepromazine.

The microscope probe was placed on the cornea along the optical axis of the eye and photographs were taken. Prints were made by enlarging the negative 3.5-times, and the prints were overlaid by a grid with 14×14 mm squares. The total number of cells in each of four squares was counted and the average taken and multiplied by 100 to obtain the number of cells per square millimeter of the cornea.

e) Ocular Tolerability/Toxicity: Ocular exams, including slit lamp biomicroscopy (Zeiss or Haag-Streit), gonioscopy, and binocular indirect ophthalmoscopy (American Optical or Keeler), were performed by a trained ophthalmologist, using when necessary contact lenses specially fabricated for the small monkey eye (Kaufman and Wallow, Exp. Eye Res., 40:883–885 [1985]). In addition, specular microscopy was used to evaluate drug effects on the corneal endothelium.

f) Bárány's Solution: Bárány's solution, a specialized physiologic phosphate buffer designed to minimize the facility increase induced by anterior chamber perfusion, is well-known in the art (Bárány, Invest. Ophthalmol., 3(2): 135–143 [1964]). The inventors prepared their own solution, one liter of solution containing: 8 g NaCl; 0.35 g KCl; 0.17 g $CaCl_2$; 64 mg $MgCl_2$; 69 mg $Na_2H_2PO_4$; 13.7 mg $NaH_2PO_4$; and 1 g glucose.

g) Source of Chemical Compounds: Both H-7 and staurosporine are commercially available from Sigma. Some of the latrunculin-A and swinholide-A were provided by Dr. Ilan Spector, while in some experiments (as indicated herein), these compounds were obtained from Molecular Probes (LAT-A) or Calbiochem (LAT-B). However, it is not intended that the present invention be limited to compounds obtained from any particular source, as there are various sources of suitable compounds for use with the present invention.

As previously discussed, latrunculin-A is a 2-thiazolidinone macrolide isolated from the marine sponge *Latrunculia magnifica*. The sponges are prominent in and may be collected from the Red Sea, where they can be found at a depth of 6.0 to 30.0 meters. The sponges may be squeezed manually to collect the toxic fluid. A combination of Sephadex LH-20 and Silica-gel chromatographies allows one to get rid of the glycerides in the fluid, and obtain three pure toxins, one of which is latrunculin-A which may be isolated via separation techniques known in the art. The structure of latrunculin-A, an oil, is presented in FIG. 2 (Kashman et al., Tetrahedron Letters 21:3629–3632[1980]; and Spector et al., Cell Motil. Cytoskel., 13:127–44[1989]).

Swinholide-A is a macrolide isolated from the marine sponge *Theonella swinhoei*; the sponge may be collected, among other places, from the Red Sea. Swinholide-A may by obtained from frozen *Theonella swinhoei* lyophilized and successively extracted with petrol-ether and $CH_2Cl_2$/MeOH (8:2). The latter extract may then be chromatographed on Sephadex LH-20(MeOH/$CHCl_3$(1:1)) and on silica gel (petrol-ether, ether, ethyl acetate). The ethyl acetate fractions provide swinholide-A as a microcrystalline compound (melting point, 102° C., $C_{39}H_{66}O_{10} \cdot H_2O$) (Carmely and Kashman, Tetrahedron Lett., 26:511–514[1985]; Bubb et al, J. Biol. Chem., 270:3463–3466[1995]).

In addition, ML-7 (Sigma) and KT5926 (Sigma, Calbiochem) are commercially available. KT5926 may also be prepared from a related compound, K-252a, which is isolated by techniques, known in the art, from the culture broth of Nocardiopsis sp. K-252 (Kase et al., J. Antibiotic. (Tokyo) 39:1059–1065[1986]). K-252a is acetylated with acetic anhydride and dimethylamineopyridine at the —NH and —OH positions. The acetate that is obtained is then acetylated by a Friedel-Crafts reaction and oxidized by a Baeyer-Villiger reaction at the 14-position and the acetyl groups are removed by treatment with sodium methoxide. The 14-hydroxy group introduced above is then n-propylated with sodium hydride and n-propyl iodide to yield KT5926 (Nakanishi et al., Mol. Pharmacol., 37:482–488[1990]).

9. Data Analysis a) Control Experiments: For each animal tested, one eye received drug and the opposite eye received vehicle without drug (i.e., a simultaneous contralateral, sham-treated paired control). For unilaterally ciliary muscle-disinserted animals, both eyes received a dose of drug known to be effective. In this situation, the control is the contralateral normal eye, as the question being addressed is whether ciliary muscle disinsertion matters (i.e., whether the drug's action depend on ciliary muscle-trabecular meshwork connection). The statistical analysis is as described below.

For the cell culture experiments, the control was culture medium without drug. There is no statistical analysis in this context, the interpretation being descriptive, analogous to pathology. The effects are routinely monitored by microphotography.

b) Statistical Analysis: Well-known and accepted techniques were utilized to determine the effect of the compounds tested. The techniques are summarized below.

First, mean baseline facility for (i) treated eyes (more accurately, to-be-treated eyes) and (ii) control eyes (contralateral eyes from (i)) were determined. The mean baseline ratio of treated eyes/control eyes was then determined; eyes were deemed "equivalent" if they did not differ statistically from 1.0. Second, mean post-drug administration facility and mean control (i.e., post-vehicle) administration facility were determined, and the mean post-administration ratio was compared. Third, the mean ratio of post-administration/baseline was determined for both the treated eyes and the control eyes; using ratios reduces inter-animal variability. Finally, the mean ratio of the ratios determined in the third step was determined: $[(\text{post-drug}/\text{baseline})_{treated}/(\text{post-drug}/\text{baseline})_{control}]$; this reduces inter- and intra-animal variability. A value statistically greater than 1.0 indicates a drug-induced facility increase (determined using a 2-tailed paired t-test).

As alluded to in the preceding paragraph, this strategy accounts for differences in baseline values between opposite eyes of the same animal, the effect of the perfusion itself, and differences in starting values between animals, thereby isolating the drug effect from other confounding variables.

The following Examples serve to illustrate certain preferred embodiments and aspects of the present invention and are not to be construed as limiting the scope thereof.

EXAMPLE 1

Dose-Dependent Affect of H-7 on Total Outflow Facility Occurs Through a Direct Effect on the Trabecular Meshwork This Example describes experiments to examine the dose-dependent effect of H-7 on total outflow facility, as measured by 2-level constant pressure perfusion of the anterior chamber (described above) of both eyes simultaneously with Bárány's solution.

Initially, it should be noted that the protocols for the testing of H-7 (and some of the other compounds, described below) were as follows: (i) after determination of vehicle-only baselines, one eye received drug and the other eye received vehicle without drug; (ii) analogous to the first protocol, with the exception that after the post-drug determination, both eyes received vehicle without drug to determine reversibility of the drug effect; (iii) in monkeys with unilateral disinsertion of the ciliary muscle, both eyes received drug after determination of vehicle-only baseline; (iv) drug-free baseline facility was again determined in both eyes of animals which had received a facility-effective drug dose unilaterally on the first occasion; this protocol was conducted four-to-six weeks after the first. The second and first baselines were then compared, corrected for any change in the control eye, to see if the drug effect had persisted.

Increasing concentrations of H-7 were tested to determine the approximate dose which yielded a statistically significant increase in outflow facility. Initially, each concentration of H-7 was prepared by dissolving the appropriate amount of H-7 in Bárány's solution. For the treated eye, H-7 was administered in Bárány's solution without DMSO as a vehicle, while the contralateral eye was administered vehicle alone. In separate experiments, 2 ml of H-7 solution was passed through the anterior chamber of the eye in a 10–15 minute period. Facility measurements were taken 60 minutes thereafter.

Figure 5A:
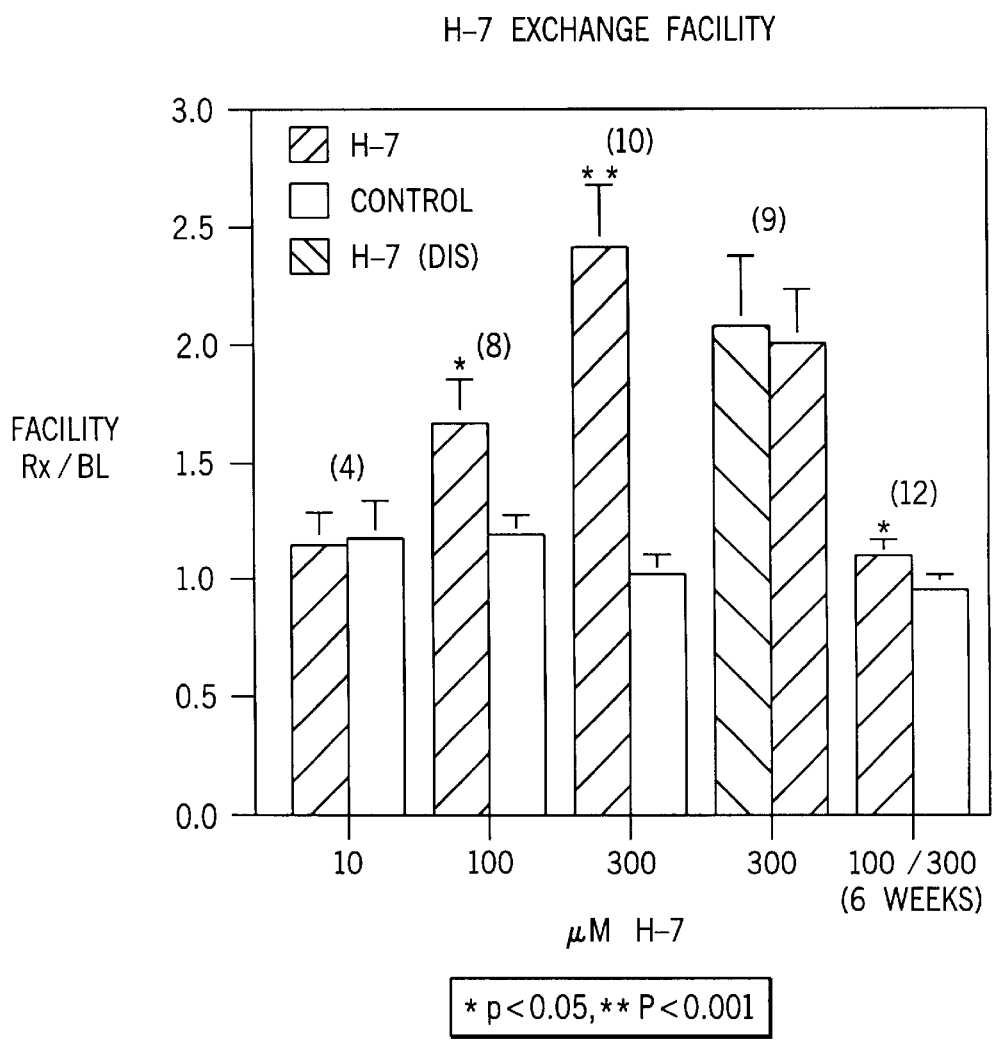
FIG. 5A is a bar graph illustrating the effect of several concentrations of H-7 on facility in living monkey given as an exchange infusion with total outflow facilities measured by 2-level constant pressure perfusion before and after drug administration.

FIG. 5A is a bar graph illustrating the effect of several concentrations of H-7 on facility. In FIG. 5A, the difference between the ratio of Rx/BL and 1.0 indicates the increase in facility in eyes administered H-7 (ipsilateral eyes) or vehicle alone (i.e., control or contralateral eyes) over baseline measurements (BL=pre-treatment (baseline) and Rx=post-treatment with H-7 or vehicle alone). In FIG. 5A, the "open" bars represent eyes administered vehicle only, while the "speckled" bars indicate eyes administered H-7. The numbers in parentheses represent the number of experimental animals, while *=p<0.05 and **=p<0.001 are the probabilities that the double ratio defined above equals 1.0 by the 2-tailed paired t-test.

At a concentration of 10 $\mu$M, no increase in outflow facility was found. However, at a concentration of 100 $\mu$M, a borderline-significant effect was observed (data not shown). When the initial post-treatment values for both the treated and the control eyes were eliminated (thereby examining a longer exposure time) at a concentration of 100 $\mu$M H-7, a stronger and statistically-significant effect was observed. Administration of 300 $\mu$M H-7 provided a larger and more strongly significant increase in outflow facility.

In addition, an experiment was also conducted to determine where H-7 exerts its effect. For this experiment, 300 $\mu$M H-7 was administered to nine monkeys with disinserted ciliary muscle in one eye, the contralateral eyes without disinsertion. As expected, the ciliary muscle-disinserted eyes had lower baseline facilities. However, both the ciliary muscle disinserted and the non-disinserted eyes exhibited essentially identical proportional increase in outflow facility following drug administration (FIG. 5A). In FIG. 5A, the "shaded" bar indicates ciliary muscle-disinserted eyes administered H-7, while the "speckled" bar represents normal eyes administered H-7. These data indicate that H-7 exerts its effect directly on the trabecular meshwork and not via the ciliary muscle. By comparison, pilocarpine exerts its effect via the ciliary muscle.

Finally, six-weeks after treatment, drug-free baseline facility was again determined in both eyes of animals which had received a facility-effective drug dose (100 or 300 µM) unilaterally on the first occasion. The second and first baselines were then compared, corrected for any change in the control eye, to see if the drug effect had persisted. As indicated on the far right in FIG. 5A (labeled 100/300), there was a significant increase in facility for the H-7 treated eyes as compared to the control eyes.

The results presented in FIG. 5A indicate that H-7 induced a dramatic dose-dependent facility increase. As set forth in the preceding paragraph, this increase is due to a direct effect on the trabecular meshwork. These in vivo experiments provide important information regarding the dose-dependent and the pharmacologic behavior of 1H-7, demonstrating its potential usefulness as an anti-glaucoma agent in humans.

EXAMPLE 2

H-7 Does not Significantly Effect Corneal Endothelial Cell Counts at a Concentration Effective at Increasing Total Outflow Facility In this Example, the effect of 300 µm H-7 on corneal endothelium was determined in cynomolgus monkeys via transcorneal intracameral injection.

The basic experimental protocol was as follows. Following administration of ketamine (10 mg/kg) anesthesia, slit lamp examination was performed to provide a baseline evaluation of the cornea, lens, and anterior chamber. Thereafter, the monkeys were anesthetized with IM pentobarbital-sodium (35 mg/kg). A 3 mM H-7 solution (2.1858 mg H-7 dissolved in 2 ml Bárány's solution, pH adjusted to 6–7) was manufactured, and 10 µl of that solution was administered to one eye and 10 µl of Bárány's solution to the opposite eye (keeping the needle away from the area to be photographed during the transcorneal intracameral injection). Specular micrographs were taken at 1 and 3 hours after H-7 administration to determine corneal endothelial cell counts and morphology, and slit lamp examination was repeated, observing the cornea, lens, and anterior chamber for any changes from baseline. Finally, specular micrographs were performed again at two-three weeks after H-7 administration, allowing the determination of corneal endothelial cell counts and morphology.

Corneal endothelial cell counts were measured as the number of cells/mm$^2$ and are reported in Table 3. In Table 3, BL=baseline cell counts; Rx(1)=cell counts 1 hour after H-7 administration, Rx(2)=cell counts 3 hours after H-7 administration, and Rx(3)=cell counts 2 weeks after H-7 administration; Treated=eyes administered H-7; Control= eyes administered vehicle only; and T/C=Treated/Control. As indicated by the data presented in Table 3, the specular micrographs did not reveal a statistical change in cell counts (n=4, p=NS).

TABLE 3

Cell Counts

| | Cell Count (cell/mm$^2$) | | |
|---|---|---|---|
| | Treated | Control | T/C |
| BL | 2328 ± 51 | 2344 ± 54 | 0.99 ± 0.02 |
| Rx(1) | 2481 ± 98 | 2756 ± 117 | 0.91 ± 0.06 |
| Rx(1)/BL | 1.07 ± 0.06 | 1.18 ± 0.06 | 0.91 ± 0.07 |
| Rx(2) | 2513 ± 131 | 2544 ± 33 | 0.99 ± 0.05 |
| Rx(2)/BL | 1.08 ± 0.07 | 1.09 ± 0.04 | 0.99 ± 0.04 |
| Rx(3) | 2569 ± 91 | 2525 ± 71 | 1.02 ± 0.04 |
| Rx(3)/BL | 1.10 ± 0.05 | 1.08 ± 0.05 | 1.02 ± 0.03 |

Similarly, no morphological changes in cells were observed. These results suggest that administration of outflow-facilitating doses of H-7 does not have a detrimental effect on corneal safety, at least in the young healthy monkey. Of course, this may or may not be the same situation in the older human population, which has an age-related decrease in endothelial cells.

It should be noted that the above-mentioned basic protocol for corneal endothelial cell counts will also be followed for other agents that show a positive effect on outflow facility. Moreover, determinations of corneal thickness, one measure of corneal endothelial cell function, can be performed to supplement these results.

EXAMPLE 3

The Effect of Topical Administration of H-7 on Outflow Facility in Cynomolgus Monkeys Generally speaking, agents used in the treatment of glaucoma are administered topically as an eyedrop, rather than being injected into the eye. This Example describes the results on outflow facility following the topical administration (i.e., via an eyedrop) of four different concentrations of H-7.

Following administration of ketamine (10 mg/kg) anesthesia, slit lamp examination was performed on the monkeys. Thereafter, the monkeys were anesthetized with IM pentobarbital-sodium (35 mg/kg). Baseline facility was measured (7 periods) by 2-level constant pressure perfusion of the anterior chamber; thereafter, the perfusion system was closed.

Four H-7 solutions of differing concentrations were manufactured: (i) a 90 mM solution (~0.3 mg H7 dissolved in 10 µl of 10% DMSO with Bárány's solution, pH of the resulting solution adjusted to approximately 7); (ii) a 150 mM solution (~1.1 mg H7 dissolved in 20 µl of 25% DMSO with Bárány's solution, pH of the resulting solution adjusted to approximately 7); (iii) a 450 mM H-7 solution (~3.3 mg H7 dissolved in 20 µl of 25% DMSO with Bárány's solution, pH of the resulting solution adjusted to approximately 7), and (iv) a 650 mM H-7 solution (~5.7 mg H-7). Thereafter, each concentration of H-7 solution was administered to the superior cornea of one eye and vehicle (25% DMSO) to the opposite eye (5 µl×4 drops), waiting 90 seconds between each drop; in addition, the lower eyelid was lifted immediately after each drop to allow adequate drug/vehicle contact with the cornea. Two hours after H-7 administration, the perfusion system was reopened and facility was measured for 9 periods.

Figure 5B:
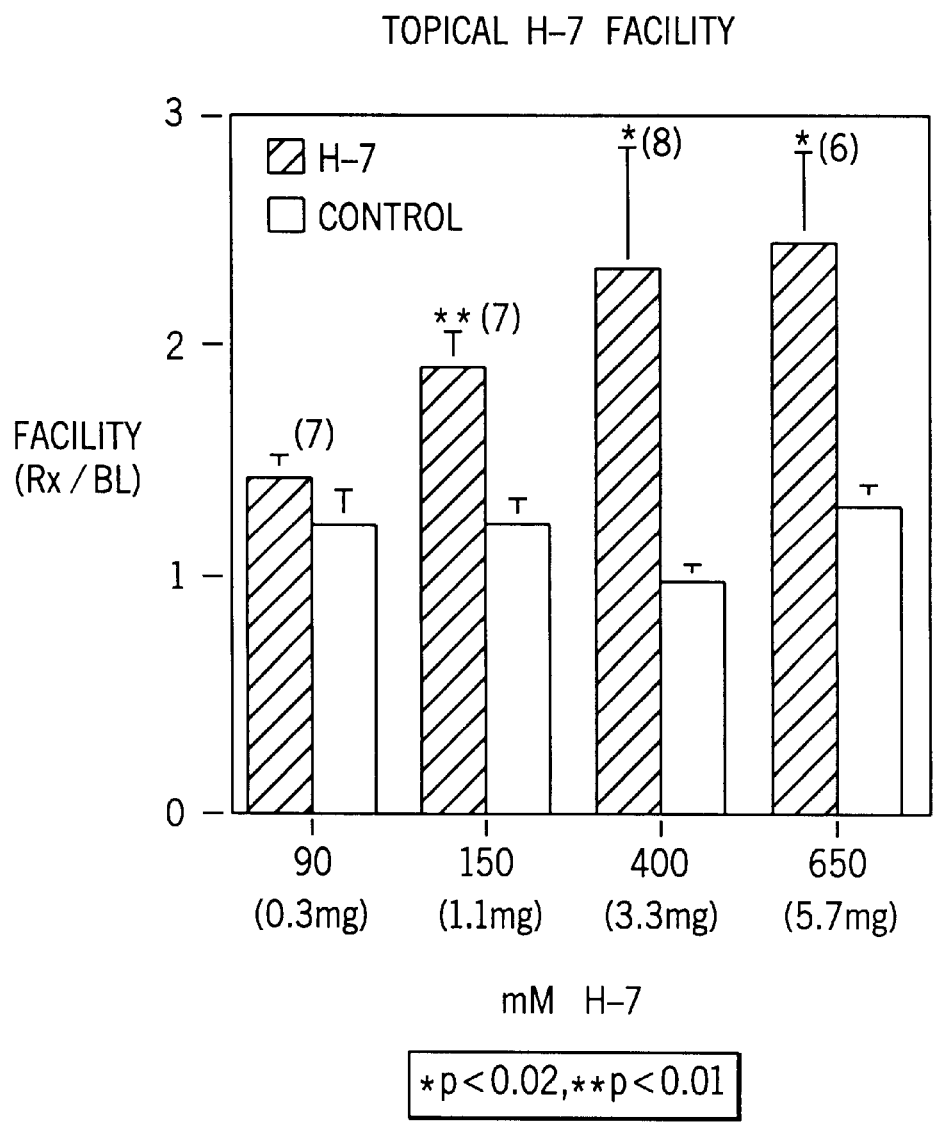
FIG. 5B is a bar graph illustrating the effect on facility of several concentrations of H-7 topically administered to living monkeys.

The resulting data are presented in FIG. 5B. In FIG. 5B, the ratio of Rx/BL indicates the increase in facility in eyes administered H-7 (ipsilateral eyes) or vehicle alone (i.e., control or contralateral eyes) over baseline measurements (BL=pre-treatment (baseline) and Rx=post-treatment with H-7 or vehicle alone). The "open" bars represent eyes administered vehicle only, while the "speckled" bars indicate eyes administered H-7. The numbers in parentheses represent the number of experimental animals, while *=p<0.02 and **=p<0.001 are the probabilities that the double ratio defined above will equal 1.0 by the 2-tailed paired t-test.

At 90 mM H-7, there was a suggestion of a small effect on outflow facility, but the effect was not statistically significant. By comparison, topical administration of 150 mM H-7 had a definite statistical effect on outflow facility. The administration of 450 and 650 mM had a larger effect, demonstrating that H-7 has a defined dose-response relationship when administered topically.

EXAMPLE 4

The Effect of Topical Administration of H-7 on Pupil and Accommodation in Cynomolgus Monkeys The previous Examples have been directed at the effect of H-7 on outflow facility. By contrast, this Example describes experiments to examine the effect of topical administration of H-7 on pupil size and refraction in cynomolgus monkeys.

The experimental protocol was as follows. Following administration of ketamine (10 mg/kg) anesthesia, baseline slit lamp examination was performed on the six monkeys tested. Thereafter, the monkeys were anesthetized with IM pentobarbital-sodium (35 mg/kg). Baseline refraction (2–3 readings) and pupil size were then measured as described above. Subsequently, a 150 mM 1H-7 solution (1.0929 mg H7 dissolved in 20 $\mu$l of 25% DMSO with Bárány's solution, pH of the resulting solution adjusted to approximately 7) was administered to the cornea of one eye, and vehicle (25% DMSO) to the opposite eye (5 $\mu$l×4 drops).

Beginning 45 minutes after H-7 administration, pupil size and refraction were evaluated every 15 minutes until 2 hours after the H-7 administration. A slit lamp examination was then performed to check for toxicity. The data are presented in FIGS. 6A and 6B.

Figure 6A:
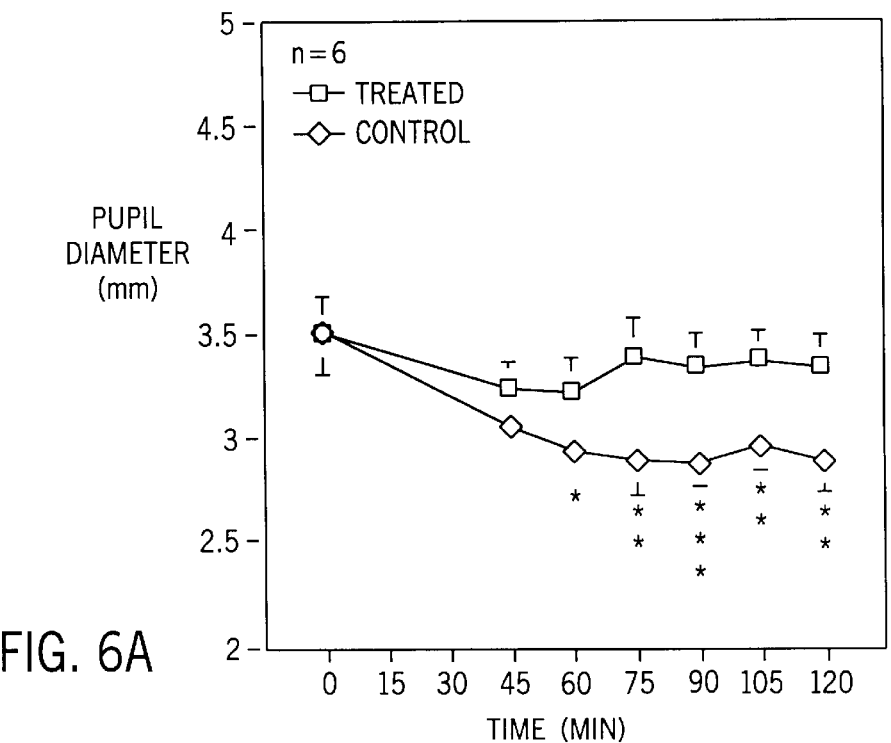
FIG. 6A graphically illustrates the effect of topical H-7 on pupil size.

FIG. 6A graphically illustrates the effect of topical H-7 on pupil size, pupil diameter (mm) being indicated as a function of time (min). Time 0 represents drug administration, and the open squares represent eyes treated with H-7, while the open diamonds represent the control eyes. The results indicate that the control pupil gets smaller with prolonged anesthesia, while the pupil subjected to H-7 does not. The following statistical levels are depicted in FIG. 6A: *=p<0.05, =p<0.02, and *=p<0.005 by the 2-tailed paired t-test for differences between eyes unequal to 0.0.

Figure 6B:
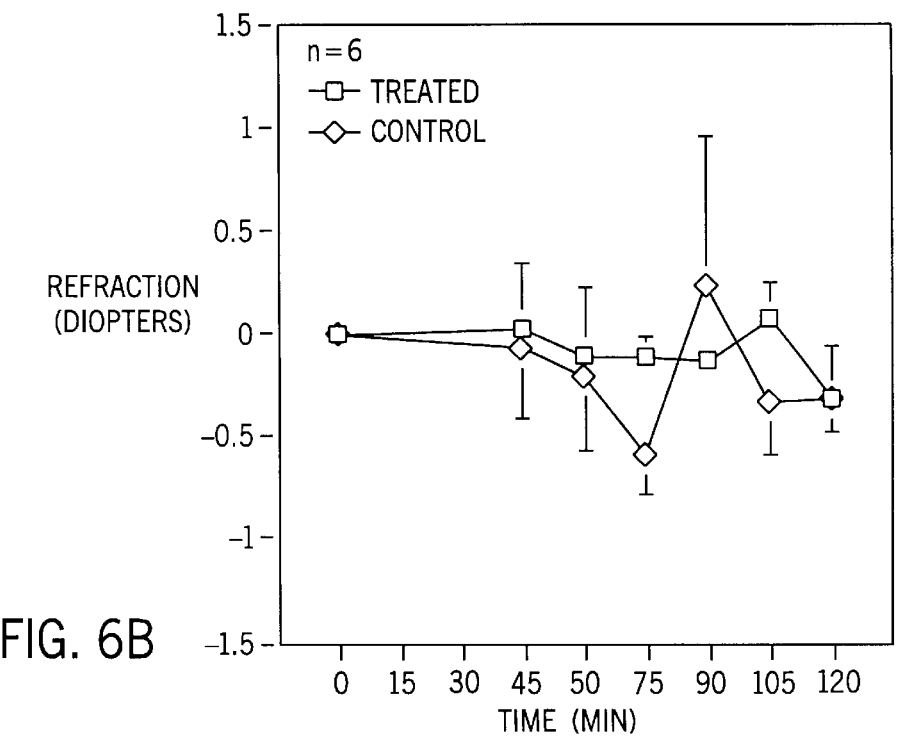
FIG. 6B graphically illustrates the effect of topical H-7 on refraction.

FIG. 6B graphically illustrates the effect of topical H-7 on refraction (diopters) indicated as a function of time (min). Again, time 0 represents drug administration, and the open squares represent eyes treated with H-7, while the open diamonds represent the control eyes. The results indicate that there is no statistically significant difference in refraction between the control eye and the treated eye.

Therefore, while H-7 did have an effect on pupil size, a concomitant effect on refraction was not observed in monkeys.

EXAMPLE 5

H-7 Prevents Pupillo-Constrictive Effect of Pilocarpine, but not Accommodative Effect of Pilocarpine This Example is directed at determining whether selective inhibition of miosis (dependent on contraction of the iris sphincter muscle) as compared to accommodation (dependent on contraction of the ciliary muscle) can be achieved.

FIGS. 7A–H graphically depict the results of this experiment, and reference to those figures will also assist in understanding the experimental protocol. The experiments of this example examined the miotic response (FIGS. 7A, C, E, and G), determined by pupil diameter (mm), and the accommodative response (FIGS. 7B, D, F, and H), measured in diopters, to pilocarpine in the presence or absence of H-7 in normal living monkey eyes. Each of the 4 rows of panels represents a different dose of H-7. In each row, the left-hand panel represents the pupillary diameter, while the right-hand panel represents the accommodative response in the same animals. Within each panel, "n" represents the number of animals for that protocol. In each experiment, baseline readings (BL) of the pupillary diameter were obtained with vernier calipers held just in front of the cornea, after which phenylephrine (2.5%) was topically administered to the eyes, resulting in mydriasis.

Figure 7A:
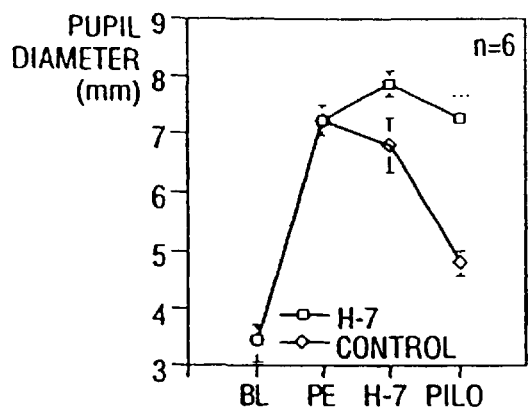
FIGS. 7A–H graphically depict miotic response (FIGS. 7A, 7C, 7E, and 7G) and accommodative response (FIGS. 7B, 7D, 7F, and 7H) to intramuscular pilocarpine in either the presence or absence of H-7.
Figure 7C:
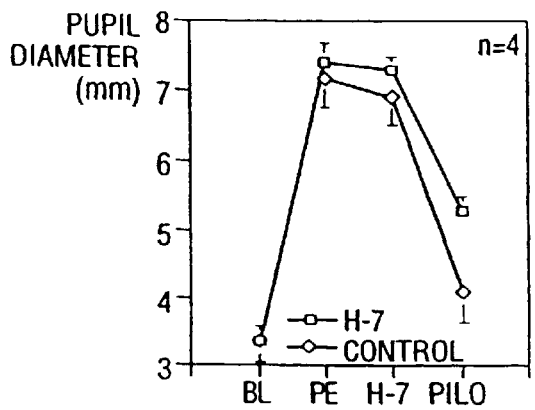
Figure 7E:
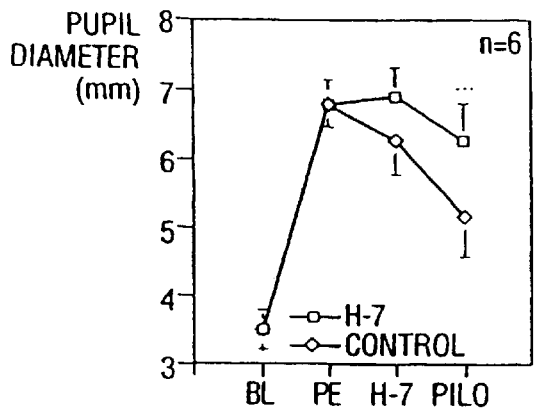
Figure 7G:
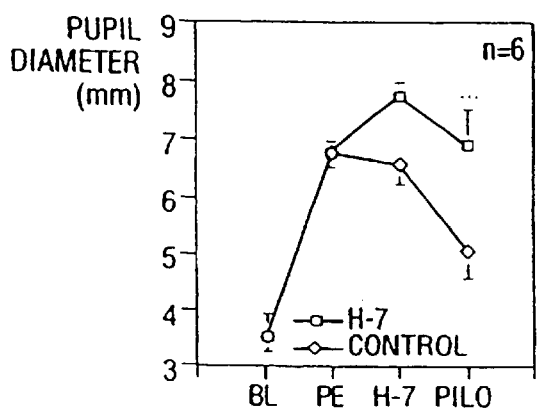

Thereafter, different protocols were used in the administration of H-7 to the animals. Six animals (FIGS. 7A and 7B) received 10 $\mu$l of 3 mM H-7 via transcorneal intracameral injection, resulting in a final anterior chamber concentration =~300 $\mu$M (microM). The remaining animals received H-7 by intravitreal injection as follows: (i) four animals (FIGS. 7C and 7D) received 10 $\mu$l of 75 mM H-7; (ii) six animals (FIGS. 7E and 7F) received 20 $\mu$l of 75 mM H-7, and (iii) six animals (FIGS. 7G and 7H) received 20 $\mu$l of 150 mM H-7, all in 50% DMSO. The final intravitreal concentrations of H-7 were 300 $\mu$M, 600 $\mu$M, and 1.2 mM, respectively. Contralateral control eyes received Bárány's solution with 50% DMSO (FIGS. 7C–H) or without 50% DMSO (FIGS. 7A, B). Pupillary diameter and refraction (accommodation being defined as refraction at a given time point minus the baseline refraction) were measured approximately 25–30 minutes after phenylephrine (PE on the abscissae of the panels). H-7 was then administered, and pupil diameter and accommodation were measured 25 minutes later (H-7 on the graphs).

Thirty minutes following H-7 administration, pilocarpine (1.5 mg/kg) was infused IM into the thigh of the monkeys over a 10-minute period, insuring slowly rising but always equal pilocarpine concentrations reaching the iris sphincter and ciliary muscles of both eyes simultaneously. Pupillary diameter was then measured 30 minutes after pilocarpine administration (Pilo on the left-hand panels), while accommodation was measured every 5 minutes for ~50 minutes beginning at the start of the IM infusion (Pilo on the right-hand panels). In FIGS. 7A–H, the solid lines connecting the solid squares indicate the eyes which will receive or have received H-7, while the solid lines connecting the open diamonds indicate the contralateral eyes of the same animals which received vehicle without H-7. The data in FIGS. 7A–H are mean±s.e.m. for "n" monkeys. The following significance levels are depicted in FIGS. 7A–H: *P<0.05; P<0.01; *P<0.001. The significance of the difference between treated and control pupil diameter (FIGS. 7A, 7E, 7G) or final accommodative response (FIG. 7H) was determined by the 2-tailed paired t-test.

Figure 7B:
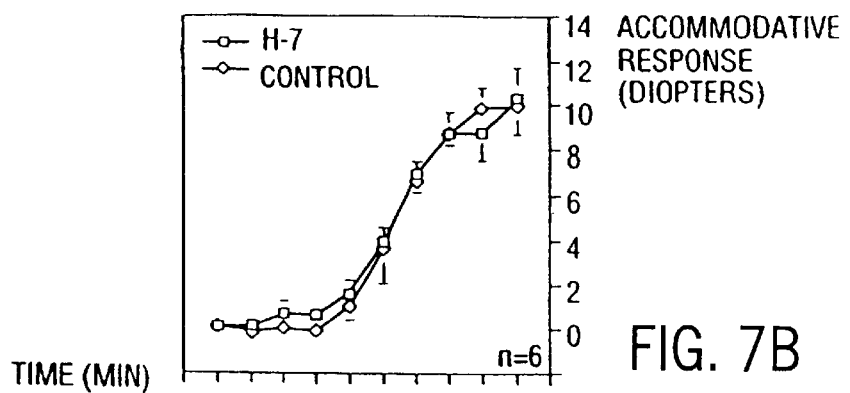
Figure 7D:
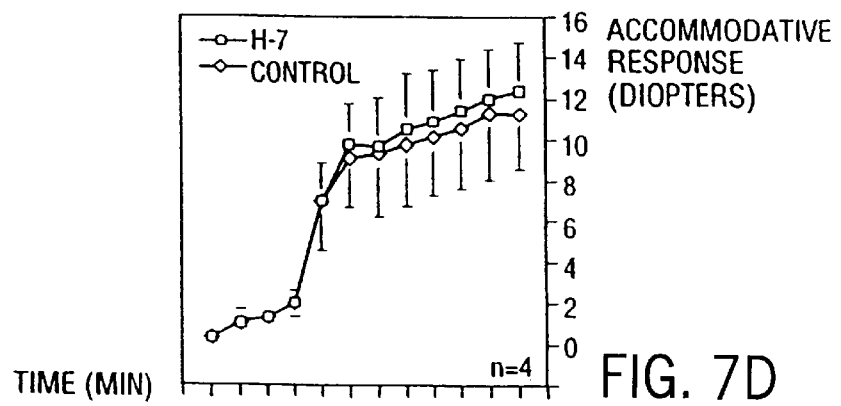
Figure 7F:
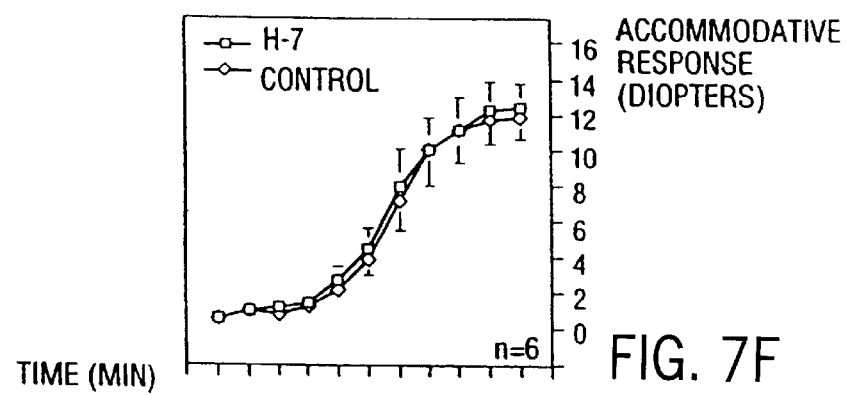
Figure 7H:
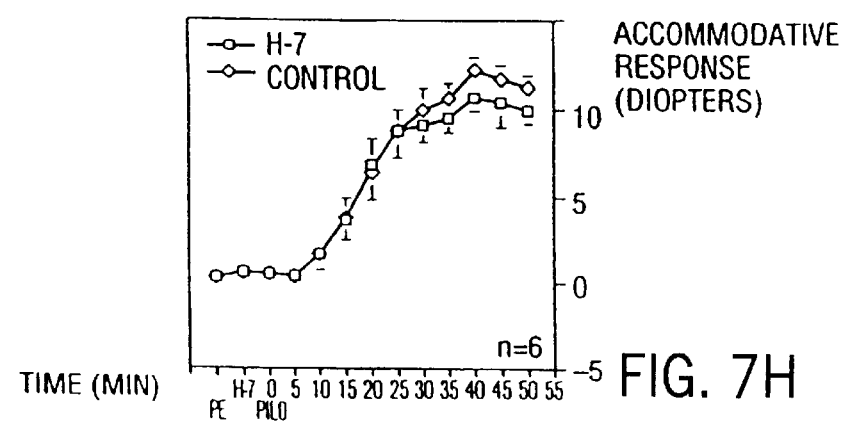

As depicted in FIGS. 7A–H, the data show that H-7 dilates the ipsilateral pupil even beyond the effect of phenylephrine, and inhibits ipsilateral pilocarpine-induced miosis, at intracameral and intravitreal doses far lower than required for inhibition of accommodation. This is best shown in FIGS. 7A–B for intracamerally administered H-7 and FIGS. 7E–F and 7G–H for intravitreally administered H-7.

EXAMPLE 6

The Effect of H-7 on Pilocarpine-Induced Contraction of the Ciliary Muscle

The experiments described in this Example were designed to determine the effect of H-7 on the ciliary muscle's contractile response to pilocarpine. The muscle chamber apparatus that has been previously described was used in these experiments.

Figure 8A:
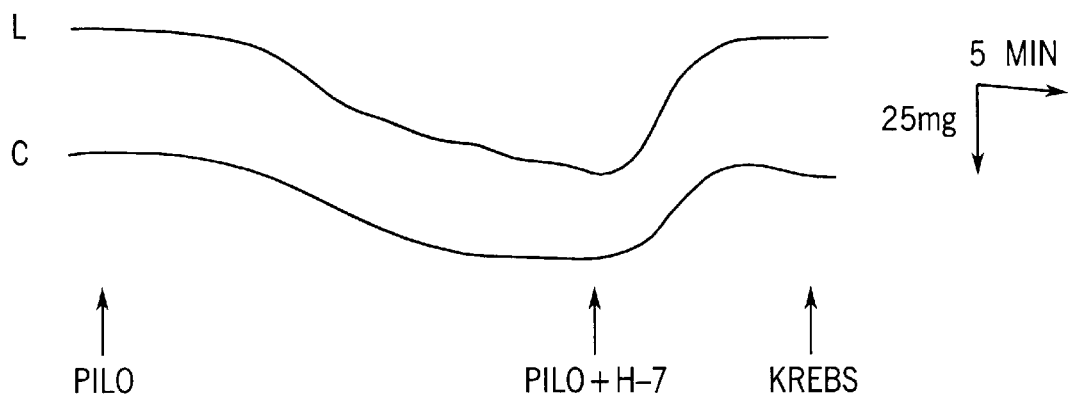
FIGS. 8A–C depict chart recorder traces obtained from a single in vitro ciliary muscle strip and were designed to determine the effect of H-7 on the ciliary muscle's contractile response to pilocarpine.
Figure 8B:
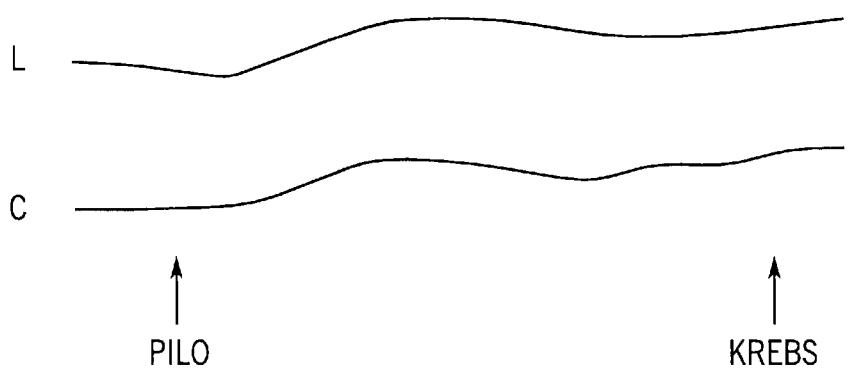
Figure 8C:
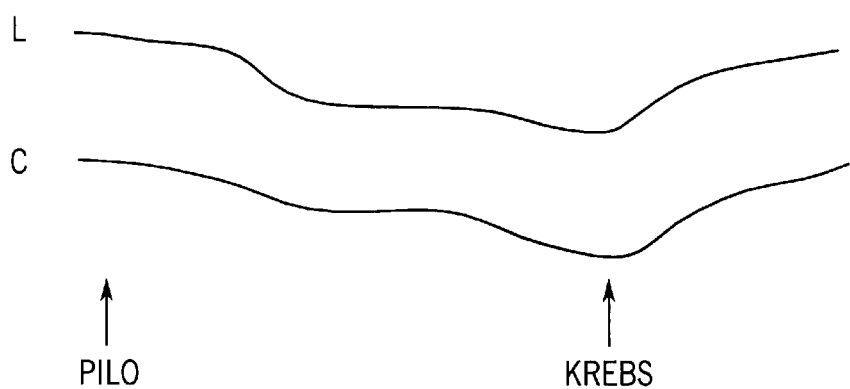

FIGS. 8A–C depict chart recorder traces obtained from a single in vitro ciliary muscle strip maintained in Krebs solution. In the traces, which are read from left to right, muscle strip contraction is indicated in the downward direction per the scale indicated; more specifically, in the scale shown in FIG. 8A, the length of the downward-pointing arrow indicates a contraction (tension) of 25 mg, while the length of the horizontal arrow pointing to the right indicates a duration of 5 minutes. Referring to FIGS. 8A–C, L=longitudinal contractile vector and C=circular contractile vector; Krebs=administration of Krebs solution without other drugs; pilo=administration of pilocarpine; and Pilo+ H-7=concomitant administration of pilocarpine and H-7

In FIG. 8A, a ciliary muscle strip under baseline tone was first exposed to 10 $\mu$M pilocarpine, then to 10 $\mu$m pilocarpine+300 µM H-7. As indicated by the chart recorder trace, the initial addition of pilocarpine resulted in contraction. However, the addition of H-7 (i.e., pilocarpine+H-7) resulted in inhibition of the initial pilocarpine contraction within 10 minutes of exposure. At the conclusion of the experiment, washout of the muscle strip was achieved by exposure of perfusand without drugs for a 90 minute period (indicated by the "Krebs" designation in FIG. 8A).

Subsequent to the washout period, the same ciliary muscle strip was exposed to 10 µM of pilocarpine. As shown by the chart recorder trace in FIG. 8B, such exposure elicited no contraction in either vector. Finally, in the same ciliary muscle strip following a further 60 min of washout (now 2.5 hours after removal of H-7), 10 µM of pilocarpine now elicited sluggish contraction in both vectors; this is shown by the chart recorder trace in FIG. 8C.

The experiments described above suggest that the effects of H-7 are relatively long-lasting, even after its removal from the perfusand. This finding also suggests that the in vivo dissociation of miosis and accommodation in response to an intracameral or intravitreal infusion of H-7 (300 µm) may have a pharmacokinetic basis. Based on the data from this one concentration, H-7 appears to have no selectivity for one vector over the other; however, vector-selectivity might be observed at other concentrations.

EXAMPLE 7

Latrunculin-A Inhibition of Cell Contractility

The experiments in this Example were conducted to establish probable dose and time course for latrunculin-A for subsequent in vivo studies on living monkeys. As previously indicated, latrunculin-A is a Red Sea sponge-derived macrolide which forms a 1:1 molar complex with G-actin, preventing the nucleation and elongation of actin filaments.

An established line of bovine aortic endothelial cells were plated at half confluency on clean glass coverslips and cultured in DMEM, containing 1 g of glucose, 9% bovine calf serum, 100 mg penicillin, 100 mg streptomycin per 550 ml, for 2–4 days at 37° C., 7% $CO_2$/93% $O_2$, 90% humidity. The medium was then changed to one containing Latrunculin-A concentrations of 0.02, 0.05. 0.2, 0.5, or 2.0 µM for 1, 2, 3, 5, or 24 hours, after which the cells were washed with 50 mM MES buffer, permeabilized with 0.5% Triton X-100 in MES, and fixed with 3% paraformaldehyde. The medium was then exposed to rhodamine phalloidin (for fluorescent labelling of actin), or to rabbit pan-cadherin primary antibody followed by goat anti-rabbit secondary antibody (for immunofluorescent labelling of cadherin, a major protein associated with C—C adherens junctions); and examined by fluorescence microscopy.

In associated experiments to judge the ability of the cells to recover from the drug, after exposure to drug for various concentrations and times (based on the previous experiments), the medium was changed to an identical one without drug for 15 minutes, 1 hour, 5 hours, 18 hours or 22 hours, and the cells washed, fixed, labelled, and examined as above. Structural alterations were found in both the actin filaments and the C—C adhesions (in summary, disruption of the actin filaments within the cells and separation of cells from their neighbors) which were both drug-dose and exposure time-dependent; the higher the dose and the longer the exposure time, the more pronounced the effects. Analogously, recovery was also dose- and time-dependent; the lower the dose, the shorter the exposure time, and the longer the drug-free interval, the more normal the appearance.

Latrunculin-A concentrations greater than 0.5 µM had unequivocal effects after 1 hour of exposure, with partial recovery evident within 0.1–5 hours after removal of the drug. Lower concentrations had more subtle slower onset effects. Based on these findings, doses of 0.2, 0.5, 2.0, and 5.0 µM were studied in living monkeys, with the positive findings as described below. It is quite likely, albeit not yet tested, that lower concentrations for longer exposure times might also be effective.

EXAMPLE 8

Dose-Dependent Effects of Latrunculin-A, Staurosporine, and Swinholide-A on Total Outflow Facility This Example involved an examination of the dose-dependent effect of latrunculin-A, staurosporine, and swinholide-A on total outflow facility. As previously described, latrunculin-A is a sea sponge-derived macrolide which forms a 1:1 molar complex with G-actin; staurosporine is a protein kinase inhibitor which disrupts the actin cytoskeleton, probably through a pathway involving inhibition of myosin light chain kinase; and swinholide-A is another sea-sponge derived macrolide which severs actin filaments and induces formation of G-actin dimers.

The experiments of this example were performed on adult cynomolgus and rhesus monkeys. Both normal monkeys and monkeys with unilateral ciliary muscle disinsertion from the scleral spur/trabecular meshwork were utilized. Briefly, the animals were anesthetized with ketamine (10 mg/kg) followed by pentobarbital sodium (35 mg/kg).

Bolus Injection: Total outflow facility was measured by 2-level constant pressure perfusion of the anterior chamber of both eyes simultaneously with Bárány's solution, as described above. The anterior chamber of both eyes was cannulated with a single branched 26-gauge needle; one arm of the needle was connected by polypropylene tubing to a continuously-weighed reservoir of Bárány's solution, while the other arm was connected to a pressure transducer. Facility measurements were taken for 35–45 minutes. With reservoirs open, 10 µl of either 5 or 20 µM latrunculin-A or 100 or 300 nM of swinholide-A were injected into the inflow tubing in one eye (0.5 µM, 2.0 µM, 10 nM, and 30 nM, respectively, in the 100,l anterior chamber), vehicle in the other, via a custom-designed micro-t-piece (positioned 2–3 cm for the eye) and a micrometer syringe. After five minutes to allow the perfusand from an elevated reservoir to wash into the anterior chamber and 3 minutes for convection mixing of the anterior chamber by blowing cold air on the cornea, facility measurements were taken for 90 minutes.

Exchange Infusion: The anterior chamber of each eye was cannulated with a branched needle connected to a reservoir and an unbranched 26 gauge needle with the tubing clamped off. Baseline facility measurements were taken for 35–45 minutes. The clamped tubing from the unbranched needle was then connected to syringes containing either drug (0.2, 0.5, 2.0, and 5.0 µM latrunculin-A, 0.1, 1.0 or 10 µM staurosporine; and 10 or 30 nM swinholide-A) or vehicle. The vehicles used were as follows: i) latrunculin-A: 0.01% DMSO for 0.2 µM and 2.0 µM, 0.25% DMSO for 0.5 µM, and 0.025% DMSO for 5.0 µM; ii) staurosporine: 0.001% DMSO for 0.1 µM, 0.1% DMSO for 1.0 µM, and 1% DMSO for 10 µM; and iii) swinholide-A: 0.1% DMSO for 10 and 30 nM. The monkeys with unilateral ciliary muscle disinsertion received drug in both eyes. The syringes were placed in a variable-speed infusion pump and the reservoir (inflow) tubing disconnected, allowing infusion of 2.0 ml of solution through the anterior chamber over 10–15 minutes (maintaining intraocular pressure at ~15 mm Hg).

The reservoirs were emptied and filled with the same solution being perfused through the eye. The reservoir tubing was then reconnected and the syringe tubing clamped. For latrunculin-A and swinholide-A, outflow facility measurements were immediately taken for 90 minutes. For staurosporine, the reservoirs were closed to inflow for 45 minutes, then opened and facility measurements were taken for 45 minutes. For the latrunculin-A reversibility exchanges, an exchange was done with 5.0 μM in one eye and vehicle in the other followed by a second exchange with vehicle give to both eyes. After each exchange, facility measurements were taken for 60 minutes.

Latrunculin-A

Figure 9A:
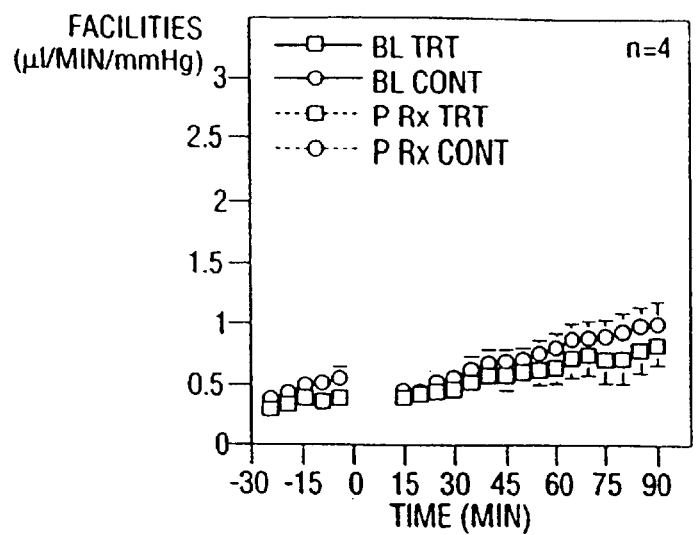
FIGS. 9A–D graphically depict the effect in living monkeys of latrunculin-A given as an exchange infusion with total outflow facilities measured by 2-level constant pressure perfusion before and after drug administration (FIG. 9A: 0.2 $\mu$M.
Figure 9B:
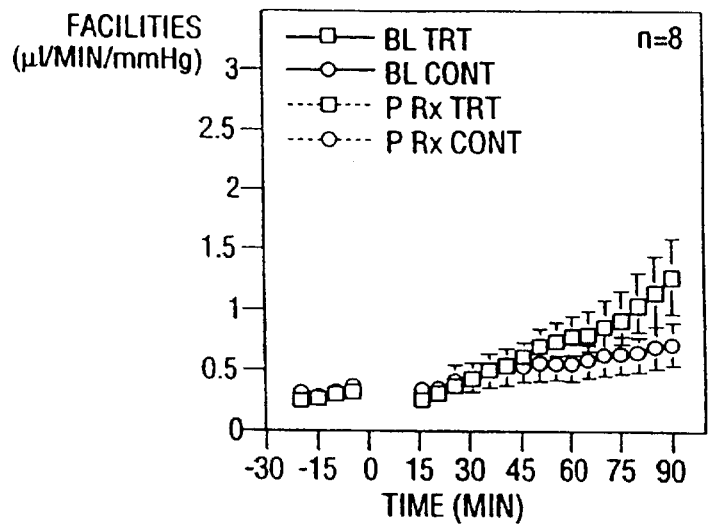
Figure 9C:
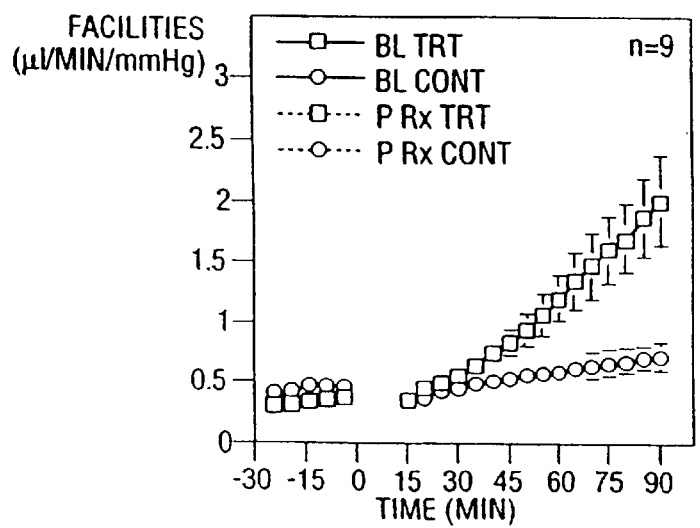
Figure 9D:
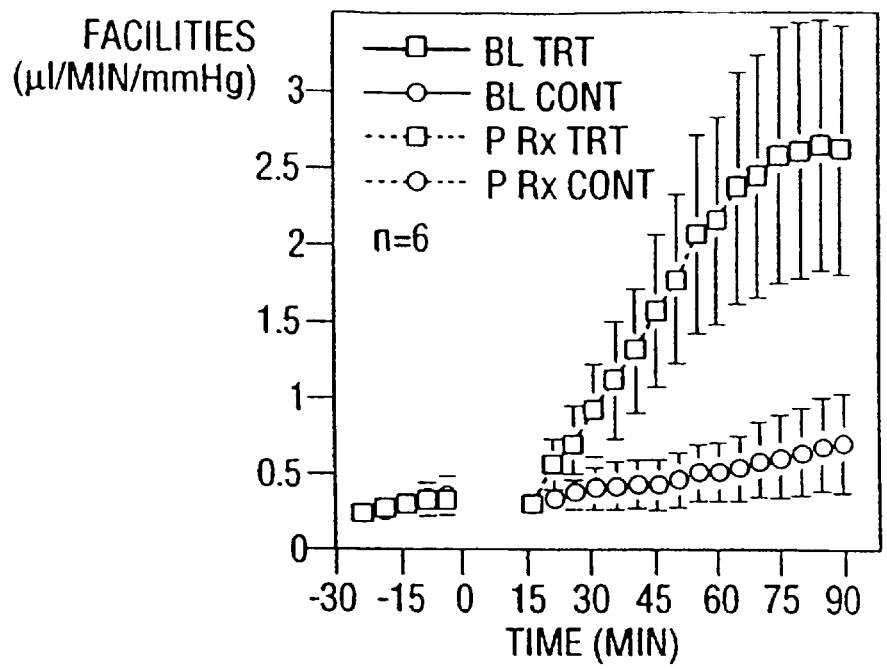

With regards to latrunculin-A, only exchange infusion induced a dose-dependent facility increase at 0.2, 0.5, 2.0, and 5.0 μM (8±14% (n=4, NS); 50±17% (n=8, p<0.025); 141±23% (n=9, p<0.001); and 329+119% (n=6, p<0.05); respectively) in normal monkeys. These data are graphically depicted in FIGS. 9A–D (FIG. 9A: 0.2 μM; FIG. 9B: 0.5 μM; FIG. 9C: 2.0 μM; and FIG. 9D: 5.0 μM), which show facility as a function of time, drug being administered at time=0. The following designations apply in those Figures: BL Trt=pre-drug administration in eyes to receive drug (open squares with solid lines); BL Cont=pre-drug administration in eyes to receive vehicle without drug (open circles with dashed lines); p rx Trt=post-drug administration in eyes which received drug (open squares with dashed lines); and p rx Cont=post-drug administration in eyes which received vehicle without drug (open circles with dashed lines). It should be noted that the bolus infusion of latrunculin-A was probably ineffective because an effective drug concentration was not maintained for sufficient time. The data are also presented in Table 4, analyzed by 30-minute post-drug time intervals where the average values for each eye are themselves averaged to give group means for the 30-minute intervals.

In this Table, BL=Baseline; Cont=Control eye; Rx=Drug treated eye. Data are mean±s.e.m. for "n" animals. Post-drug data encompasses 30 min time windows ending at the post-drug time indicated (i.e., "30 min"=0–30 min post-drug administration, etc.).

Figure 9E:
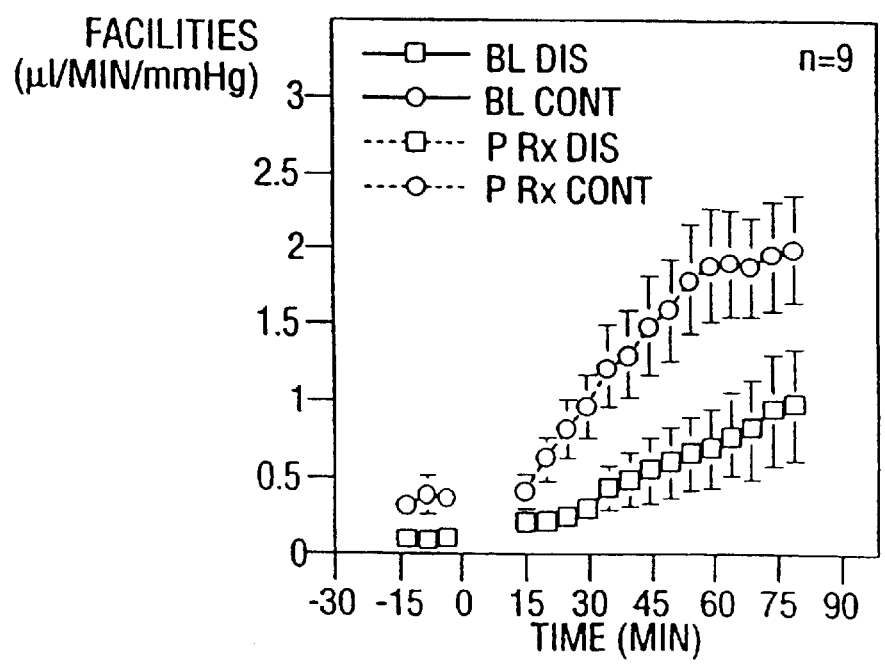
FIG. 9E graphical illustrates the effect of latrunculin-A in ciliary muscle-disinserted eyes.

In addition, latrunculin-A was equally effective in ciliary muscle-disinserted eyes, showing a facility increase of 353±129% (n=9, p<0.05), and the control eyes showing a facility increase of 328±35% (p<0.001, at the 5.0 μM dose). These data, depicted in FIG. 9E and presented in Table 5, indicate that latrunculin-A has a direct trabecular meshwork effect rather than a secondary ciliary muscle-mediated action. In this Table, BL=Baseline; PRx=Post drug administration; CM Dis=ciliary muscle disinsertion eye; and Cont=Control eye. Data are presented as the mean±s.e.m. for "n" animals with unilateral CM disinsertion receiving 5.0 μM Lat-AOU.

TABLE 5

Latrunculin-A-Ciliary Muscle Disinsertion

Facility (μl/min/mmHg)

| Dose | | CM Dis | Cont | CM Dis/Cont |
|---|---|---|---|---|
| 5.0 μM OU | BL | 0.13 ± 0.01 | 0.38 ± 0.09 | 0.45 ± 0.08 |
| (n = 9) | PRx | 0.65 ± 0.23 | 1.51 ± 0.30 | 0.43 ± 0.15 |
| | PRx/BL | 4.53 ± 1.29† | 4.28 ± 0.35# | 1.06 ± 0.27 |

†$P < 0.05$, #$P < 0.001$, for ratios different from 1.0 by the 2-tailed paired t test.

Figure 10:
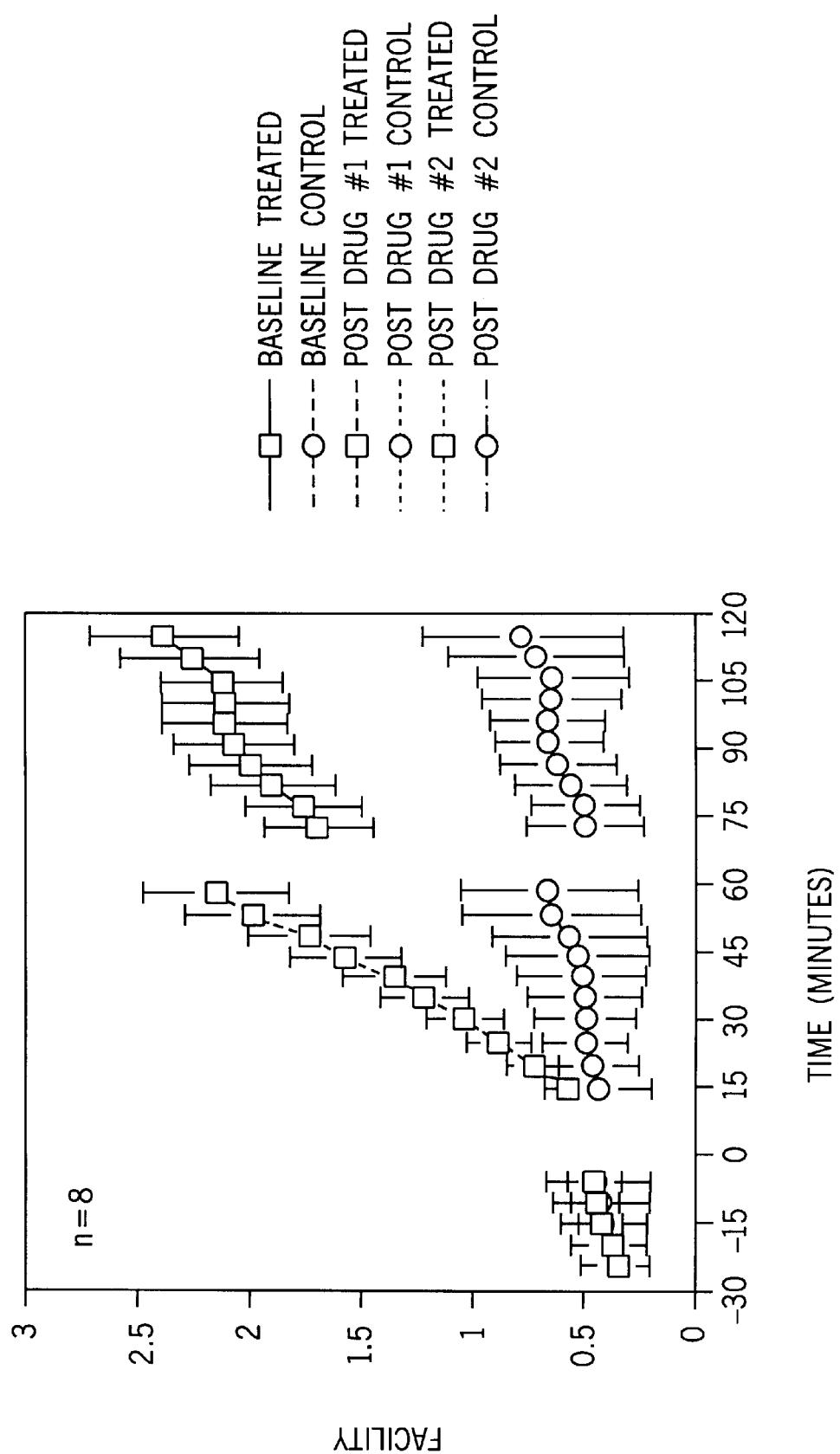
FIG. 10 graphically depicts the reversibility of the facility-effect of latrunculin-A.

Reversibility of the facility-effect of latrunculin-A (5.0 μM) was minimal for the first hour after removal of the drug, as depicted in FIG. 10. Referring to FIG. 10, each data point is the mean of the facility readings at that time for n monkeys, drug administration being at time=0. The following designations apply: baseline treated=pre-drug administration in eyes which will receive drug (open squares with solid lines); baseline control=pre-drug administration in eyes which will receive vehicle without drug (open circles with dashed lines); post drug #1/#2 treated=post-drug administration after the first/second exchange in eyes which received drug (open squares with dashed lines); post drug #1/#2 control=post-drug administration after the first/second exchange in eyes which received vehicle without drug (open circles with dashed lines).

TABLE 4

Latrunculin Exchange Facilities By 30 Minute Intervals

| Dose | | Facility (μl/min/mmHg) | | | (Rx/BL)/ |
|---|---|---|---|---|---|
| | | Rx | Cont | Rx/Cont | (Cont/BL) |
| 0.2 μM | BL | 0.38 ± 0.04 | 0.49 ± 0.09 | 0.80 ± 0.09 | |
| (n = 4) | 30 min | 0.50 ± 0.05 | 0.59 ± 0.11 | 0.90 ± 0.12 | 1.13 ± 0.12 |
| | 60 min | 0.65 ± 0.11 | 0.79 ± 0.12 | 0.85 ± 0.13 | 1.06 ± 0.14 |
| | 90 min | 0.79 ± 0.19 | 0.96 ± 0.16 | 0.85 ± 0.18 | 1.06 ± 0.20 |
| 0.5 μM | BL | 0.32 ± 0.05 | 0.36 ± 0.09 | 1.02 ± 0.13 | |
| (n = 8) | 30 min | 0.45 ± 0.08 | 0.47 ± 0.13 | 1.21 ± 0.19 | 1.17 ± 0.08 |
| | 60 min | 0.76 ± 0.15 | 0.59 ± 0.16 | 1.51 ± 0.23 | 1.53 ± 0.18‡ |
| | 90 min | 1.07 ± 0.26 | 0.69 ± 0.17 | 1.71 ± 0.29† | 1.77 ± 0.26‡ |
| 2.0 μM | BL | 0.33 ± 0.03 | 0.42 ± 0.06 | 0.85 ± 0.09 | |
| (n = 9) | 30 min | 0.58 ± 0.09 | 0.45 ± 0.05 | 1.33 ± 0.13† | 1.61 ± 0.15¶ |
| | 60 min | 1.09 ± 0.17 | 0.58 ± 0.08 | 1.91 ± 0.19† | 2.33 ± 0.22# |
| | 90 min | 1.74 ± 0.30 | 0.69 ± 0.11 | 2.56 ± 0.29# | 3.12 ± 0.36# |
| 5.0 μM | BL | 0.28 ± 0.06 | 0.29 ± 0.09 | 1.13 ± 0.13 | |
| (n = 6) | 30 min | 0.93 ± 0.30 | 0.39 ± 0.13 | 2.69 ± 0.51‡ | 2.34 ± 0.30‖ |
| | 60 min | 2.00 ± 0.61 | 0.50 ± 0.20 | 6.01 ± 2.10 | 4.83 ± 1.30† |
| | 90 min | 2.58 ± 0.80 | 0.66 ± 0.30 | 7.89 ± 3.15 | 6.14 ± 2.02 |
| Baseline | BL₁ | 0.37 ± 0.03 | 0.41 ± 0.04 | 0.97 ± 0.06 | |
| Comparison | BL₂ | 0.42 ± 0.06 | 0.44 ± 0.04 | 1.07 ± 0.17 | |
| (n = 22) | BL₂/BL₁ | 1.24 ± 0.19 | 1.19 ± 0.10 | 1.12 ± 0.15 | |

†$P < 0.05$; ‡$P < 0.025$; ‖$P < 0.01$; ¶$P < 0.005$; and #$P < 0.001$, for ratios different from 1.0 by the 2-tailed paired t-test.

The minimal reversibility exhibited by latrunculin-A was probably due to the washout of resistance-relevant material when the drug was present which does not reform quickly following drug removal. Indeed, it may not reform by the next perfusion, as indicated by the baseline comparisons.

Staurosporine

Figure 11A:
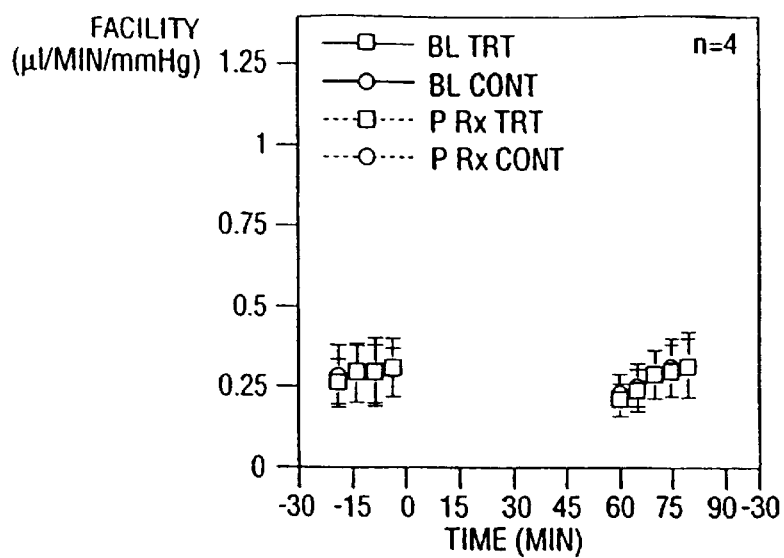
FIG. 11 graphically depicts the effect in living monkeys of staurosporine given as an exchange infusion with total outflow facilities measured by 2-level constant pressure perfusion before and after drug administration (FIG. 11A: 0.1 $\mu$M.
FIG. 11B: 01.0 $\mu$M.
FIG. 11C: 10.0 $\mu$M).
Figure 11B:
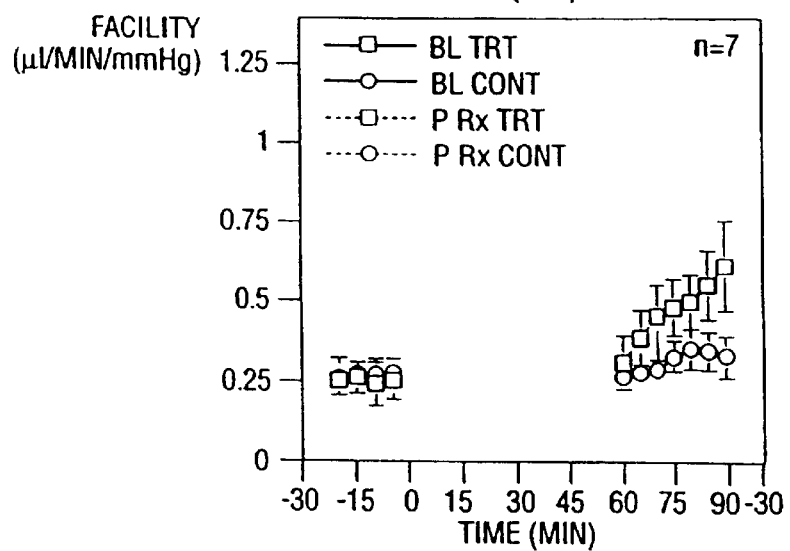
Figure 11C:
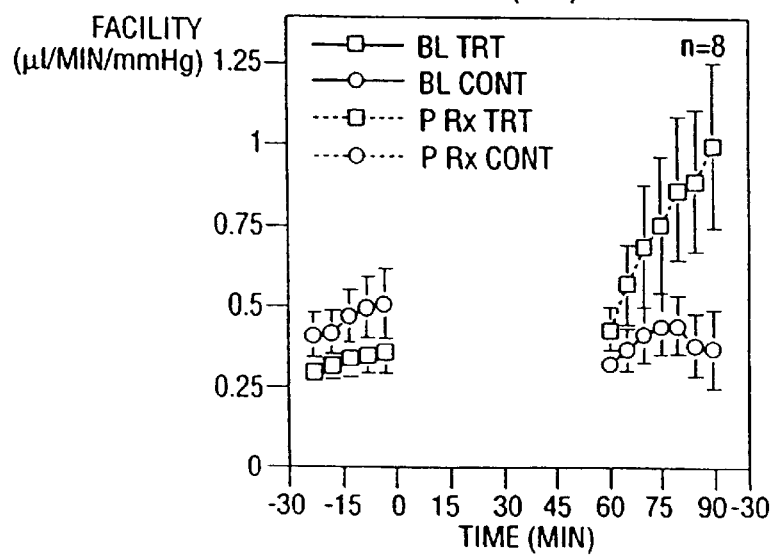

Exchange infusion of staurosporine produced a dose-dependent facility increase at 0.1 μM (microM), 1 M, and 10 μm (−2±3% (n=4, NS); 68±24% (n=7, p<0.05); and 168±48% (n=8, p<0.01); respectively). These data are graphically depicted in FIGS. 11A–C (FIG. 11A: 0.1 μM; FIG. 11B: 1.0 μM; FIG. 11C: 10.0 μM), which show facility as a function of time, drug being administered at time=0. The same designations described above for FIGS. 9A–D also apply for FIGS. 1A–C. In addition, these data are presented in Table 6, where the average value for each eye are themselves averaged to give group means for the entire time period. In Table 6, BL=Baseline; PRx=Post drug administration; Rx=Treated drug eye; and Cont=Control eye. The post-drug data encompasses 45 min, beginning 45 min after drug administration. Data are presented as the mean±s.e.m. for "n" animals.

TABLE 6

Staurosporine Exchange Facilities

| Dose | Sample | Facility (μl/min/mmHg) | | | (Rx/BL)/ |
| --- | --- | --- | --- | --- | --- |
| | | Rx | Cont | Rx/Cont | (Cont/BL) |
| 0.1 μM | BL | 0.30 ± 0.09 | 0.29 ± 0.09 | 1.04 ± 0.14 | |
| (n = 4) | PRx | 0.27 ± 0.07 | 0.28 ± 0.08 | 1.03 ± 0.17 | 0.98 ± 0.04 |
| 1.0 μM | BL | 0.28 ± 0.05 | 0.30 ± 0.05 | 0.96 ± 0.11 | |
| (n = 8) | PRx | 0.50 ± 0.08 | 0.33 ± 0.04 | 1.57 ± 0.25 | 1.69 ± 0.20[†] |
| 10 μM | BL | 0.32 ± 0.05 | 0.44 ± 0.08 | 0.81 ± 0.12 | |
| (n = 8) | PRx | 0.74 ± 0.18 | 0.39 ± 0.08 | 1.99 ± 0.43 | 2.68 ± 0.48[‡] |

[†]$P < 0.05$ and [‡]$P < 0.001$, for ratios different from 1.0 by the 2-tailed paired t-test.

Swinholide-A

In early experiments, swinholide-A doses of 10 and 30 nM did not increase facility, whether administered by bolus or exchange infusion (data not shown). It should be noted, however, that in vitro cell culture experiments with swinholide-A did reveal an effect on the cells' actin filaments and C—C adhesion. Indeed, those experiments suggested that the dosage range of swinholide-A tested in the in vivo monkey experiments described in this example would be at the low end of the dose-duration-efficacy relationship. Therefore, based on these experiments, the apparent ineffectiveness of swinholide-A was postulated to be due to inadequate dose or exposure time, not to the compound itself. In subsequent experiments, higher doses of swinholide-A than originally tested were successfully used to increase the total outflow facility in living monkeys, as discussed in Example 11, below.

Based on the results of the experiments described herein, latrunculin-A, swinholide-A, and staurosporine increased outflow facility. Though swinholide-A initially did not appear to be effective, these were likely due to the testing conditions employed, as proven in subsequent experiments (See, Example 11). In addition to being potentially advantageous agents in the treatment of glaucoma, the results of the latrunculin-A, swinholide-A, and staurosporine experiments indicate that actin cytoskeleton disorganization in the trabecular meshwork can increase outflow facility in monkeys.

EXAMPLE 9

Effect of Latrunculin-B on Outflow Facility

This Example describes experiments to observe the effects of LAT-B on outflow facility in living monkeys. As in other experiments, normal adult cynomolgus (*Macaca fascicularis*) monkeys were utilized in these experiments. The animals were anesthetized with intramuscular (i.m.) ketamine (10 mg/kg) followed by i.m. (35 mg/kg) or intravenous (i.v.; 15 mg/kg) pentobarbital sodium, supplemented by 10 mg/kg i.v. injections as needed. All experiments were conducted in accordance with UW and NIH guidelines, and with the ARVO Statement on the Use of Animals in Ophthalmic and Vision Research.

LAT-B (Calbiochem-Novabiochem) was stored as a 2 mM stock solution in DMSO (Sigma) at −20° C. LAT-B solutions for the 0.02, 0.06, 0.2 and 2 μM exchange perfusions were formulated as 0.2, 0.6, 2, or 20 μl of 2 mM LAT-B stock solution, 49.8, 49.4, 48, or 30 μl of DMSO and 19.95 ml of Bárány's mock aqueous humor solution (Bárány, Invest. Opthalmol., 3:135–143[1964]). Vehicle for all exchange perfusions was formulated as 50 μl DMSO and 19.95 ml Bárány's solution (0.25% DMSO). The LAT-B and vehicle solutions for topical application (200 μM and 500 μM LAT-B, 10% and 25% DMSO) were formulated respectively as 3 μl of 2 mM LAT-B stock solution or DMSO±27 μl of Bárány's solution; or 11.25 μl of 2 mM LAT-B stock solution or DMSO±33.75 μl of Bárány's solution.

In this Example, the data are presented as the mean±s.e.m. for "n" eyes or animals. Pre- or post-LAT-B treated vs contralateral control; post-LAT-B or post-vehicle vs ipsilateral baseline; and baseline corrected post-LAT-B treated vs control comparisons were made using the 2-tailed paired t-test for differences vs 0.0 or ratios vs 1.0.

Total Outflow Facility

Total outflow facility was determined by 2-level constant pressure perfusion of the anterior chamber (AC) with Bárány's mock aqueous humor (Bárány, supra), correcting for the internal resistance of the perfusion apparatus as appropriate. Most monkeys had undergone prior perfusions but not within the preceding 5–6 weeks; all were free of AC cells and flare by slit-lamp biomicroscopy.

The AC of both eyes was cannulated with a branched needle connected to a reservoir and pressure transducer and an unbranched needle with tubing clamped off. Baseline facility measurements were taken for 35–45 min. The clamped tubing from the unbranched needle was then connected to syringes containing drug (0.02, 0.06, 0.2, or 2 μM LAT-B) or vehicle (0.25% DMSO). The syringes were placed in a variable speed infusion pump and the tubing previously leading to the reservoir was disconnected from the reservoir and opened to air as a temporary outflow line, allowing infusion of 2 ml of solution through the AC over 10–15 min, while maintaining IOP at ~15 mmHg by adjusting the height (e.g., 15–16 cm higher than the eye) of the end of the outflow tubing. The reservoirs were emptied and re-filled with the same solution being perfused through the eye. The "temporary outflow" tubing was reconnected to the reservoir and the syringe tubing was clamped again, allowing infusion from the reservoir into the eye. Outflow facility measurements were immediately taken for 90 min.

The AC of both eyes of was cannulated with a branched needle as above, after which baseline facility measurements were taken for 35–45 min. With reservoirs closed, 2×5 µl drops of 200 µM (~0.8 µg) or 4×5 µl drops of 500 µM (~4.0 µg) LAT-B were given to one eye of the prone monkey, allowing 60–90 sec between drops. The drops were placed at the superior limbus and allowed to flow down the cornea, after which the lower lid was lifted two or three times. Vehicle (10 or 25% DMSO respectively) was given simultaneously to the opposite eye in a similar manner. The doses were chosen to give 0.2 µm and 1 µM LAT-B concentrations respectively in the 100 µl monkey AC (See e.g., Erickson-Lamy et al., Arch. Opthalmol., 102:1815–1820[1984]), assuming 1% penetration and no initial drug loss from the AC (Asseff et al., Amer. J. Ophthalmol., 75:212–215[1973]; Harris, in Leopold (ed.), *Symposium on Ocular Therapy*, C. V. Mosby, St. Louis, Mo., [1968], pp. 96–105; Janes and Stiles, Arch. Ophthahnol., 62:69–74[1959]). The perfusion system remained closed for 2 hr, after which facility measurements were taken for 90 min. Biomicroscopy was performed by an ophthalmologist before and 3, 7 and 14 days after drug administration.

Figure 12:
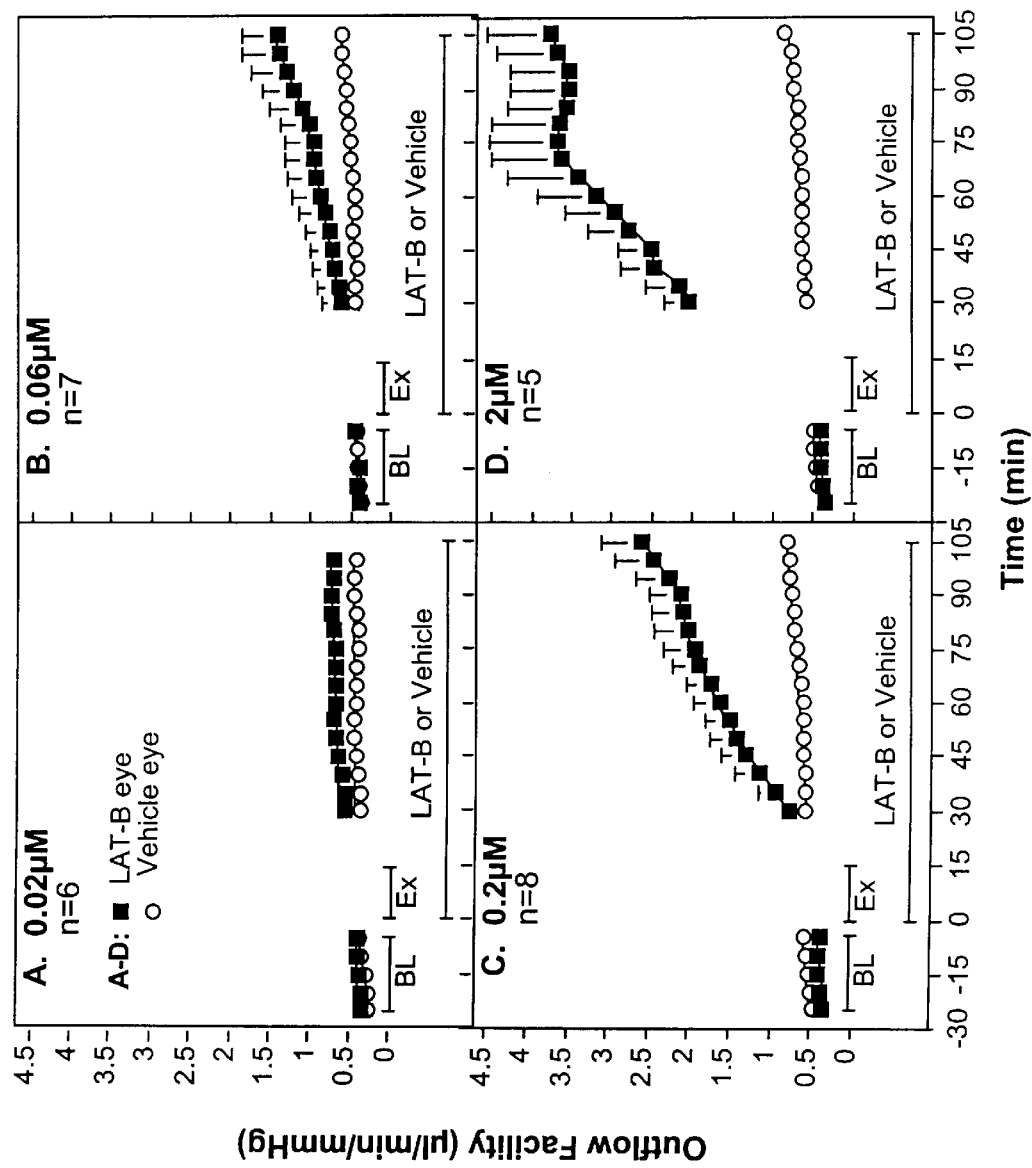
FIGS. 12A–D provide data showing outflow facilities vs time for LAT-B exchange protocols. Each data point is the mean±s.e.m. of the facility readings at that time (some error bars are smaller than the symbols) for "n" monkeys, each contributing one LAT-B-treated and one vehicle-treated eye to the data set (FIG. 12A: 0.02 $\mu$M.

Exchange infusion of 0.02–2.0 µm LAT-B produced a dose- and time-dependent facility increase, with 2 µM LAT-B infusion increasing facility by an average of 456±128% (n=5, p<0.025) over a 90 min period, correcting for baseline differences and control eye washout (See, FIG. 12, and Table 7). In Table 7, "BL" refers to baseline values, while "Veh" refers to values for the vehicle-treated eye, and "LAT-B" indicates the LAT-B treated eye. Data are shown as the mean±s.e.m. for "n" animals, each contributing one LAT-B treated and one vehicle-treated eye to the data set. The P values indicated were determined using the two-tailed paired t-test for ratios different from 1.0.

TABLE 7

Intracameral LAT-B Exchange Facilities (30 Minute Intervals)

Facility ($\mu l$ min$^{-1}$ mmHg$^{-1}$)

| LAT-B | Dose | Sample/Time | LAT-B | Vehicle (Veh) | LAT-B/Vehicle | (LAT-B/BL)/Veh/BL) |
|---|---|---|---|---|---|---|
| (A) | 0.02 µM (n = 6) | BL | 0.38 ± 0.06 | 0.31 ± 0.05 | 1.30 ± 0.18 | |
| | | 0–30 min | 0.64 ± 0.11 | 0.44 ± 0.06 | 1.61 ± 0.32 | 1.19 ± 0.14 |
| | | 30–60 min | 0.70 ± 0.14 | 0.42 ± 0.06 | 1.84 ± 0.40* | 1.34 ± 0.19 |
| | | 60–90 min | 0.73 ± 0.14 | 0.45 ± 0.06 | 1.81 ± 0.37* | 1.33 ± 0.14* |
| (B) | 0.06 µM (n = 7) | BL | 0.43 ± 0.13 | 0.41 ± 0.10 | 1.10 ± 0.25 | |
| | | 0–30 min | 0.77 ± 0.27 | 0.46 ± 0.08 | 1.59 ± 0.24* | 1.51 ± 0.18† |
| | | 30–60 min | 0.98 ± 0.34 | 0.50 ± 0.10 | 1.79 ± 0.25‡ | 1.81 ± 0.20§ |

TABLE 7-continued

Intracameral LAT-B Exchange Facilities (30 Minute Intervals)

Facility ($\mu l$ min$^{-1}$ mmHg$^{-1}$)

| LAT-B | Dose | Sample/Time | LAT-B | Vehicle (Veh) | LAT-B/Vehicle | (LAT-B/BL)/Veh/BL) |
|---|---|---|---|---|---|---|
| | | 60–90 min | 1.30 ± 0.43 | 0.61 ± 0.11 | 1.97 ± 0.28‡ | 2.05 ± 0.28§ |
| (C) | 0.2 µM (n = 8) | BL | 0.39 ± 0.04 | 0.54 ± 0.12 | 0.83 ± 0.10 | |
| | | 0–30 min | 1.29 ± 0.26 | 0.61 ± 0.11 | 2.48 ± 0.62† | 2.99 ± 0.60‡ |
| | | 30–60 min | 1.86 ± 0.32 | 0.68 ± 0.10 | 2.98 ± 0.60‡ | 3.73 ± 0.63‖ |
| | | 60–90 min | 2.31 ± 0.42 | 0.78 ± 0.09 | 2.95 ± 0.40‖ | 3.88 ± 0.64‖ |
| (D) | 2 µM (n = 5) | BL | 0.41 ± 0.08 | 0.46 ± 0.09 | 0.90 ± 0.07 | |
| | | 0–30 min | 2.60 ± 0.45 | 0.64 ± 0.08 | 4.34 ± 1.01† | 4.79 ± 0.97‡ |
| | | 30–60 min | 3.54 ± 0.81 | 0.69 ± 0.10 | 5.64 ± 1.72* | 6.16 ± 1.64† |
| | | 60–90 min | 3.64 ± 0.73 | 0.79 ± 0.11 | 5.00 ± 1.37† | 5.47 ± 1.29† |

*P < 0.1; †P < 0.05; ‡P < 0.02; §P < 0.01; and ‖P < 0.005, for ratios different from 1.0 by the 2-tailed paired t-test.

Figure 13:
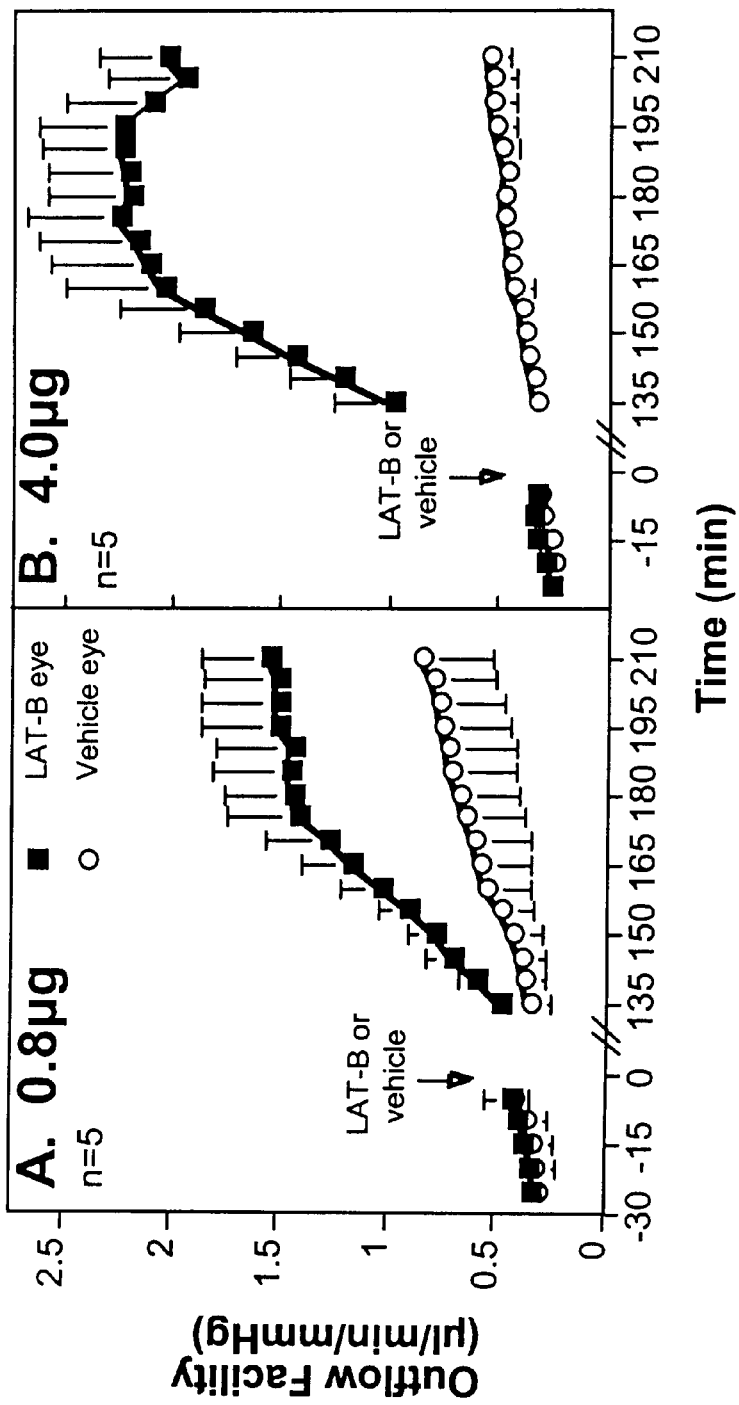
FIGS. 13A–B provide data showing outflow facilities vs time for LAT-B topical protocols (FIG. 13A: 0.8 $\mu$g.

Topical application of LAT-B produced a dose- and time-dependent facility increase of 123±67% (n=5, p=NS) and 272±45% (n=5, p<0.005) for the 0.8 and 4.0 µg doses respectively, averaged over a 90 min period (See, FIG. 13, and Table 8). In Table 8, "BL" refers to the baseline values, while "Veh" refers to the values for the vehicle-treated eye, and "LAT-B" refers to the LAT-B-treated eye. Data are presented as the mean±s.e.m. for "n" animals, each contributing one LAT-B treated and one vehicle-treated eye to the data set. The P values indicated were determined using the two-tailed paired t-test for ratios different from 1.0.

Biomicroscopy 3 days after topical drug administration and AC perfusion showed no adverse effects at the 0.8 µg dose. At the 4.0 µg dose, two drug-treated eyes exhibited a small clot of blood in the AC, and two drug-treated eyes and one vehicle-treated eye exhibited a few keratic precipitates on day 3 after perfusion. However, by day 7, all eyes appeared biomicroscopically normal.

TABLE 8

Topical LAT-B Exchange Facilities (30 Minute Intervals)

Facility ($\mu l$ min$^{-1}$ mmHg$^{-1}$)

| LAT-B | Dose | Sample/Time | LAT-B | Vehicle (Veh) | LAT-B/Vehicle | (LAT-B/BL)/Veh/BL) |
|---|---|---|---|---|---|---|
| (A) | 0.8 µg 2 hr wait (n = 5) | BL | 0.37 ± 0.07 | 0.34 ± 0.10 | 1.18 ± 0.11 | |
| | | 0–30 min | 0.80 ± 0.13 | 0.44 ± 0.14 | 2.30 ± 0.65 | 1.84 ± 0.33 |
| | | 30–60 min | 1.35 ± 0.30 | 0.64 ± 0.27 | 3.37 ± 1.40 | 2.59 ± 0.81 |
| | | 60–90 min | 1.50 ± 0.34 | 0.77 ± 0.31 | 3.14 ± 1.47* | 2.37 ± 0.87 |
| (B) | 4.0 µg 2 hr wait (n = 5) | BL | 0.31 ± 0.03 | 0.27 ± 0.04 | 1.18 ± 0.16 | |
| | | 0–30 min | 1.64 ± 0.34 | 0.38 ± 0.07 | 4.49 ± 1.12† | 3.68 ± 0.47‖ |
| | | 30–60 min | 2.19 ± 0.46 | 0.46 ± | 4.74 ± | 4.03 ± |

TABLE 8-continued

Topical LAT-B Exchange Facilities (30 Minute Intervals)

| LAT-B | Dose | Sample/Time | LAT-B | Vehicle (Veh) | LAT-B/Vehicle | (LAT-B/BL)/Veh/BL) |
|---|---|---|---|---|---|---|
| | | min | 0.42 | 0.07 | 0.86‡ | 0.46‖ |
| | | 60–90 min | 2.11 ± 0.36 | 0.52 ± 0.10 | 4.22 ± 0.67§ | 3.68 ± 0.52§ |

*$P < 0.1$; †$P < 0.05$; ‡$P < 0.02$; §$P < 0.01$; and ‖$P < 0.005$, for ratios different from 1.0 by the 2-tailed paired t-test.

To determine the initial LAT-B effect, the first facility value upon restarting the perfusion after drug administration was compared with the final baseline value obtained just prior to drug administration ($PRx_f/Prx_i$ in Table 9). Exchange infusion and topical eyedrop administration both caused a dose-dependent initial facility increase, with the initial post-drug value increasing over the final baseline value by 379±125% (n=5, p<0.05; Table 9D) following 2 μM LAT-B exchange infusion and by 173±73% (n=5, p<0.1; Table 9F) 2 hr after topical administration of 4.0 μg LAT-B. In Table 9, "BL" refers to the baseline values, while "Veh" refers to the values for the vehicle-treated eye, "Ex" refers to exchange infusion, "Top: indicates topical administration, "LAT-B" refers to the LAT-B-treated eye, "PRx" refers to facility post-ipsilateral LAT-B and contralateral vehicle administration, "i" refers to the first value of the measurement period, and "f" refers to the final value of the measurement period. Data are presented as the mean±s.e.m. for "n" animals, each contributing one LAT-B treated and one vehicle-treated eye to the data set. The P values indicated were determined using the two-tailed paired t-test for ratios different from 1.0.

TABLE 9

Intracameral and Topical LAT-B (Initial Facilities)

| LAT-B | Dose | Time | LAT-B | Veh | LAT-B/Veh |
|---|---|---|---|---|---|
| (A) | 0.02 μM | $BL_f$ | 0.40 ± 0.07 | 0.37 ± 0.05 | 1.14 ± 0.17 |
| | Ex | $PRx_i$ | 0.57 ± 0.09 | 0.37 ± 0.05 | 1.70 ± 0.33* |
| | (n = 6) | $PRx_f$ | 0.72 ± 0.15 | 0.44 ± 0.07 | 1.85 ± 0.41* |
| | | $PRx_i/BL_f$ | 1.47 ± 0.14‡ | 1.02 ± 0.08 | 1.45 ± 0.11‖ |
| | | $PRx_f/BL_f$ | 1.86 ± 0.30† | 1.21 ± 0.07† | 1.56 ± 0.23* |
| | | $PRx_f/PRx_i$ | 1.26 ± 0.14 | 1.21 ± 0.09* | 1.06 ± 0.11 |
| (B) | 0.06 μM | $BL_f$ | 0.46 ± 0.14 | 0.43 ± 0.10 | 1.15 ± 0.28 |
| | Ex | $PRx_i$ | 0.63 ± 0.23 | 0.48 ± 0.11 | 1.29 ± 0.26 |
| | (n = 7) | $PRx_f$ | 1.43 ± 0.44 | 0.64 ± 0.12 | 2.09 ± 0.31§ |
| | | $PRx_i/BL_f$ | 1.31 ± 0.09§ | 1.16 ± 0.11 | 1.16 ± 0.09 |
| | | $PRx_f/BL_f$ | 3.52 ± 0.72§ | 1.61 ± 0.10# | 2.16 ± 0.36§ |
| | | $PRx_f/PRx_i$ | 2.63 ± 0.43‖ | 1.43 ± 0.11‖ | 1.83 ± 0.23§ |
| (C) | 0.2 μM | $BL_f$ | 0.41 ± 0.04 | 0.59 ± 0.12 | 0.78 ± 0.10* |
| | Ex | $PRx_i$ | 0.78 ± 0.13 | 0.58 ± 0.09 | 1.64 ± 0.46 |
| | (n = 8) | $PRx_f$ | 2.60 ± 0.49 | 0.81 ± 0.09 | 3.18 ± 0.43¶ |
| | | $PRx_i/BL_f$ | 2.07 ± 0.44† | 1.02 ± 0.06 | 2.01 ± 0.34‡ |
| | | $PRx_f/BL_f$ | 6.51 ± 1.16¶ | 1.55 ± 0.20† | 4.36 ± 0.66¶ |
| | | $PRx_f/PRx_i$ | 3.38 ± 0.45¶ | 1.49 ± 0.14‖ | 2.40 ± 0.37‖ |
| (D) | 2.0 μM | $BL_f$ | 0.43 ± 0.09 | 0.51 ± 0.09 | 0.94 ± 0.07 |
| | Ex | $PRx_i$ | 2.07 ± 0.28 | 0.59 ± 0.06 | 3.63 ± 0.58§ |
| | (n = 5) | $PRx_f$ | 3.80 ± 0.75 | 0.88 ± 0.13 | 4.69 ± 1.29† |
| | | $PRx_i/BL_f$ | 5.70 ± 1.40† | 1.22 ± 0.10* | 4.79 ± 1.25† |
| | | $PRx_f/BL_f$ | 9.76 ± 2.05§ | 1.77 ± 0.11¶ | 5.73 ± 1.37† |
| | | $PRx_f/PRx_i$ | 1.78 ± 0.14‖ | 1.47 ± 0.09‖ | 1.24 ± 0.16 |
| (E) | 0.8 μg | $BL_f$ | 0.43 ± 0.09 | 0.41 ± 0.13 | 1.14 ± 0.08 |
| | Top | $PRx_i$ | 0.47 ± 0.08 | 0.34 ± 0.10 | 1.65 ± 0.38 |
| | (n = 5) | $PRx_f$ | 1.54 ± 0.33 | 0.84 ± 0.32 | 2.82 ± 1.22 |
| | | $PRx_i/BL_f$ | 1.16 ± 0.11 | 0.87 ± 0.06* | 1.36 ± 0.16* |
| | | $PRx_f/BL_f$ | 3.78 ± 0.70§ | 2.00 ± 0.31† | 2.12 ± 0.64 |
| | | $PRx_f/PRx_i$ | 3.41 ± 0.73† | 2.33 ± 0.35§ | 1.50 ± 0.28 |
| (F) | 4.0 μg | $BL_f$ | 0.32 ± 0.04 | 0.31 ± 0.05 | 1.09 ± 0.11 |
| | Top | $PRx_i$ | 0.98 ± 0.27 | 0.27 ± 0.05 | 3.19 ± 1.16 |
| | (n = 5) | $PRx_f$ | 2.03 ± 0.31 | 0.54 ± 0.10 | 3.92 ± 0.58‖ |
| | | $PRx_i/BL_f$ | 3.03 ± 0.94* | 1.04 ± 0.10 | 2.73 ± 0.73* |
| | | $PRx_f/BL_f$ | 6.19 ± 0.48# | 1.83 ± 0.31* | 3.69 ± 0.55‖ |
| | | $PRx_f/PRx_i$ | 3.16 ± 1.08 | 1.77 ± 0.25† | 1.80 ± 0.53 |

*$P < 0.1$; †$P < 0.05$; ‡$P < 0.025$; §$P < 0.02$; ‖$P < 0.01$; ¶$P < 0.005$; and #$P < 0.001$, for ratios different from 1.0 by the 2-tailed paired t-test.

Figure 14:
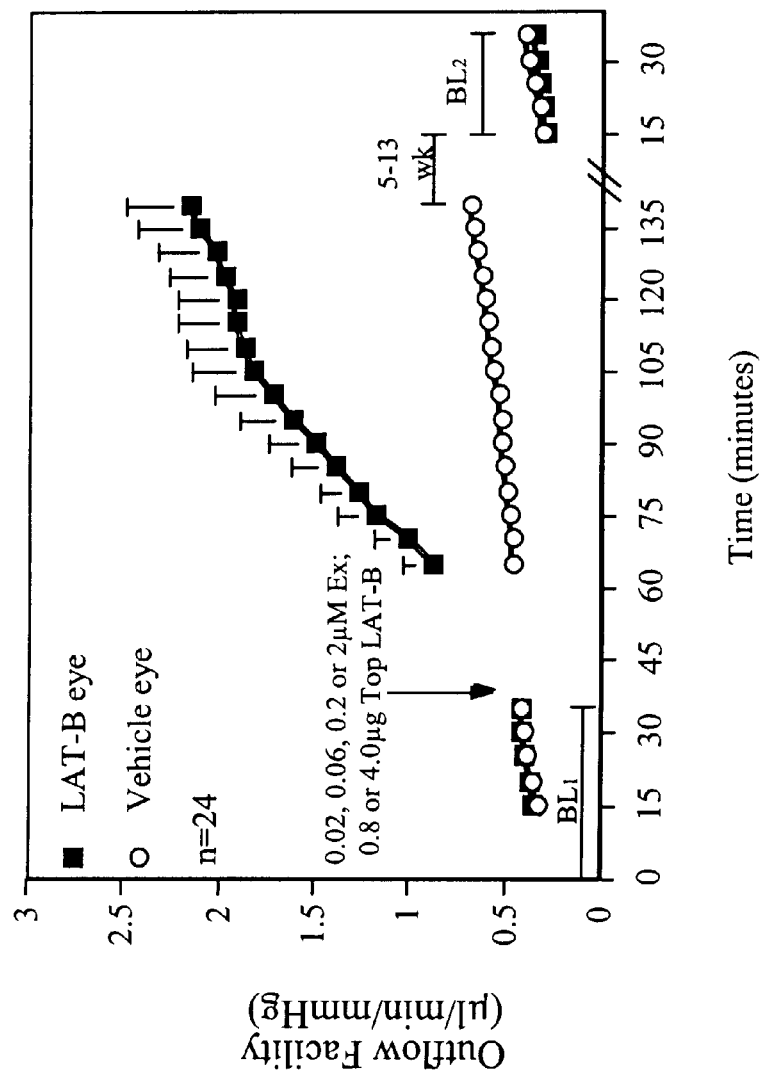
FIG. 14 provides results showing the baseline (BL) outflow facility, post-drug facility for 90 min after different concentrations of intracameral or topical LAT-B or vehicle, and baseline facility from the following perfusion 5–13 weeks later, vs time. Each data point is the mean±s.e.m. facility at that time (some error bars are smaller than the symbols) for n monkeys that received only one dose of LAT-B following $BL_1$ and did not receive any other treatment between $BL_1$ and $BL_2$. Each monkey contributed one LAT-B-treated and one vehicle-treated eye to the data set ($BL_1$=baseline before LAT-B or vehicle administration, $BL_2$=baseline at the following perfusion, Ex=AC exchange infusion).

The baseline facility 5–13 wk after intracameral or topical LAT-B was not significantly different from the baseline immediately prior to receiving LAT-B, as indicated in FIG. 14 and Table 10. In Table 10, "LAT-B" refers to the LAT-B treated eye, while "Veh" refers to the vehicle-treated eye. "$BL_1$" refers to the baseline immediately before intracameral or topical LAT-B/vehicle administration, while "$BL_2$" refers to the baseline at the following perfusion 5–13 weeks after LAT-B administration. The data are presented as the mean±s.e.m. for 24 animals that received only one dose of different concentrations of intracameral or topical LAT-B following BL, and did not receive any other treatment between $BL_1$ and $BL_2$. Each monkey contributing one LAT-B treated and one vehicle-treated eye to the data set.

TABLE 10

Comparison of Baseline Outflow Facilities Immediately Before and 5–13 Weeks After LAT-B Administration

| Sample | Facility ($\mu l\ min^{-1}\ mmHg^{-1}$) | | |
|---|---|---|---|
| | LAT-B | Veh | LAT-B/Veh |
| $BL_1$ | 0.40 ± 0.04 | 0.39 ± 0.04 | 1.12 ± 0.09 |
| $BL_2$ | 0.33 ± 0.03 | 0.36 ± 0.03 | 1.01 ± 0.08 |
| $BL_2/BL_1$ | 0.90 ± 0.05 | 1.03 ± 0.10 | 0.96 ± 0.06 |

EXAMPLE 10

Effect of Latrunculin-A and Latrunculin-B on Intraocular Pressure Aqueous Humor Flow, and Corneal Endothelium This Example describes investigations of the effects of LAT-A and LAT-B on IOP, aqueous humor flow (AHF), anterior segment fluid barrier and permeability characteristics, and/or corneal endothelial morphology and function in living monkey eyes.

For these experiments, the LAT-A was obtained from Dr. Yoel Kashman (Dept. of Organic Chemistry, Tel-Aviv University, Tel-Aviv, Israel) and stored as a 20 mM stock solution in DMSO, at 4° C. LAT-B (Calbiochem-Novabiochem) was stored as a 2 mM stock solution in DMSO (Sigma) at –20° C. The LAT-A and vehicle solutions were formulated as 11.25 µl of 20 mM LAT-A stock solution or DMSO and 33.75 µl of Báràny's mock aqueous humor to give a 5 mM LAT-A and 25% DMSO (vehicle) solution; 2×5 µl (21 µg) or 4×5 µl (42 µg) drops of the LAT-A solution are submaximal and maximal facility-effective doses respectively. The LAT-B and vehicle solutions for topical application (500 µM LAT-B, 25% DMSO) were formulated respectively as 11.25 µl of 2 mM LAT-B stock solution or DMSO+33.75 µl of Báràny's solution; 4×5 µl (4.0 µg) of the LAT-B solution is a maximal facility-effective dose. All chemicals for the Lowry assay were obtained from Sigma. Fluorescein Na used for i.v. injection was Fluorescite® 10% (Alcon).

In these experiments, the data are presented as mean±s.e.m. for "n" eyes or animals as indicated. Pre- or post-LAT-A or LAT-B treated vs contralateral control; post-LAT-A, post-LAT-B or post-vehicle vs ipsilateral baseline; and baseline corrected post-LAT-A or LAT-B treated vs control were compared by using a 2-tailed paired t-test. Differences were compared to 0.0 and ratios were compared to 1.0.

Animals and Anesthesia

The animals used in these experiments were adult cynomolgus monkeys (*Macaca fascicularis*) of both sexes, weighing 2.0–5.5 kg. Anesthesia was induced by intramuscular (i.m.) ketamine (10 mg/kg) and maintained with supplemental injections of ketamine as required (5 mg/kg every 30 to 45 minutes). Between ketamine injections during a given experiment, monkeys were in transfer cages after each measurement and usually were waking up. The duration of each experiment was 9 hours or less. Some animals received an extra single IOP measurement at 24 hr following a 9 hr experiment; they were allowed to recover fully from the anesthesia in their regular cages in the Animal Care Unit between the 9 and 24 hr measurements. Those monkeys used in the specular microscopy protocol also received i.m. acepromazine (1 mg/kg). All experiments were conducted in accordance with the ARVO Statement on the Use of Animals in Ophthalmic and Vision Research, and in compliance with NIH and University of Wisconsin guidelines.

Slit Lamp Biomicroscopy

For slit lamp biomicroscopy, a trained ophthalmologist examined all eyes by slit lamp, for integrity of the corneal epithelium and endothelium, presence of flare or cells in the anterior chamber and clarity of the lens. All animals were free of ocular abnormalities when studied.

Slit lamp examination after LAT-A or LAT-B and vehicle (25% DMSO) administration showed mild transient corneal epithelial cloudiness in both eyes, more pronounced in the LAT-treated eyes. Four LAT-A- treated eyes and one LAT-B-treated eye developed flare (1–2$^+$ on a scale of 0–4+), evidencing blood-aqueous barrier breakdown. However, these eyes recovered by 24–48 hr. None of the control eyes exhibited flare. The most obvious effect of LAT-A or LAT-B was on the corneal endothelium. One to 5 hr after receiving the drug, the cell borders in almost all LAT-A- or LAT-B-treated eyes were indistinct and the cells could not be counted. However, almost all drug-treated eyes exhibited innumerable small brightly refractile granule-like spots on the endothelium, presumably representing the endothelial cells. The spots could not be counted from the specular microphotographs, because they were not as clear on the photos as at the slit lamp. Eyes receiving the lower dose of LAT-A had fewer spots usually localized to the central area of the endothelium at 3 hr, and recovered almost completely by 6 hr. Half of the eyes receiving the higher dose of LAT-A exhibited these spots over a large area of the endothelium within 3 hr, but most recovered by 10 hr. Eyes receiving 4 µg LAT-B exhibited as many spots as those receiving the higher dose of LAT-A at 1 hr; by 3 hr, two eyes had returned to normal and all other eyes had improved; by 6 hr, the corneal endothelium of almost all treated eyes had recovered. The lens always appeared normal after both drugs.

Intraocular Pressure

The intraocular pressure (IOP) was determined with a "minified" Goldmann applanation tonometer (Kaufman and Davis, Arch. Ophthalmol., 98:542–546[1980]), using "Half and Half®" creamer solution (Borden) as the tear film indicator (Croft et al., in Lakshminarayanan (ed.), *Basic and Clinical Applications of Vision Science,* Dordtecht, Kluwer, [1997], pp. 213–216), with the monkey lying prone in a head holder and the eyes positioned 4 to 8 cm above the heart. All monkeys were examined by slit-lamp before the first IOP measurement in each protocol. For each eye, two or three IOP measurements were averaged as a baseline.

After baseline IOP was measured, 21 or 42 µg LAT-A or 4 µg LAT-B were administered to the central cornea of supine monkeys in one eye and the vehicle to the opposite eye. Blinking was prevented with lid speculums during and for 5 min. after drug administration (taking care to avoid touching the globe), to maximize drug penetration into the AC and minimize systemic absorption. Following drug administration, the speculums were gently removed and the monkeys were kept in the supine position for another 15 min to further facilitate penetration of drug/vehicle solution into the AC. For LAT-A, IOP was then measured every hr for 7 to 9 hr beginning 1, 6, or 15 hr after the 21 gg dose, or beginning 1 or 6 hr after the 42 $\mu$g dose, and again at 24 hr. Each protocol included two groups of monkeys. Group one (6 monkeys) underwent IOP measurement from 1–9 hr and again at 24 hr after the drug; group two (6 monkeys) were measured from 6–13 hr for both doses and again from 15 hr–21 hr on a separate occasion for the 21 $\mu$g dose. For both doses, one monkey in group one was used again in group two; therefore its two readings measured at baseline or the period 6–9 hr after the drug on the two different occasions was averaged for data analysis. Thus, "n" for baseline and the period 6–9 hr post-drug is 11 rather than 12. During intervals between the post-drug reading at 9 hr and that at 24 hr for group one or between the drug administration and the first post-drug reading at 6 hr for group two, the animals were returned to the Animal Care Unit for recovery. For LAT-B, IOP was measured every hr for 6 hr beginning 1 hr after the 4 $\mu$g dose, and again at 24 hr. The animals were returned to the Animal Care Unit for recovery between the measurements at 6 hr and 24 hr. Anterior segments were examined by slit-lamp at 3, 6, 10 or 24 hr after LAT-A, or at 1, 3, 6 or 24 hr after LAT-B.

Figure 15:
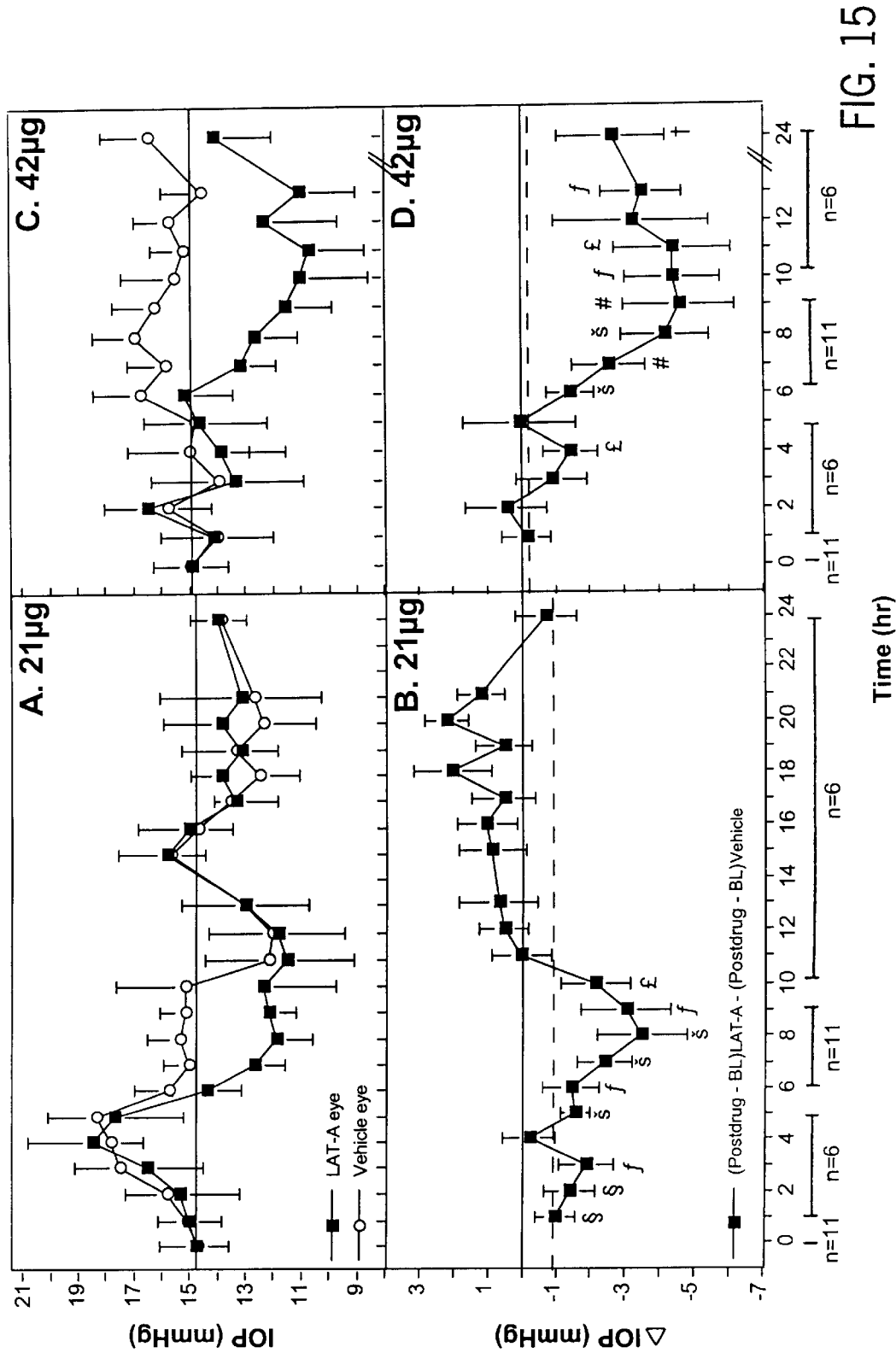
FIGS. 15A–D show the effect of topical LAT-A on IOP.

For each dose of LAT-A, the data were pooled such that continuous time lines could be created. The same monkeys were used for each time protocol whenever possible. The baseline 10 Ps for monkeys included in more than one time protocol for the same dose were averaged to provide one baseline IOP for each eye. For LAT-A, baseline IOP was ~15 mmHg. The 21 $\mu$g dose of LAT-A lowered IOP 5–10 hr after drug administration, with the maximal decrease of 3.48±1.29 mmHg below baseline (n=11, p<0.005) at 8 hr (See, FIGS. 15A and 15B). The 42 $\mu$g LAT-A dose lowered IOP 6–13 hr after drug administration, with maximal reduction of 4.60±1.61 mmHg below baseline (n=11, p<0.01) at 9 hr. IOP still had not clearly returned to baseline by 24 hr after the higher dose (See, FIGS. 15C and 15D).

Figure 16:
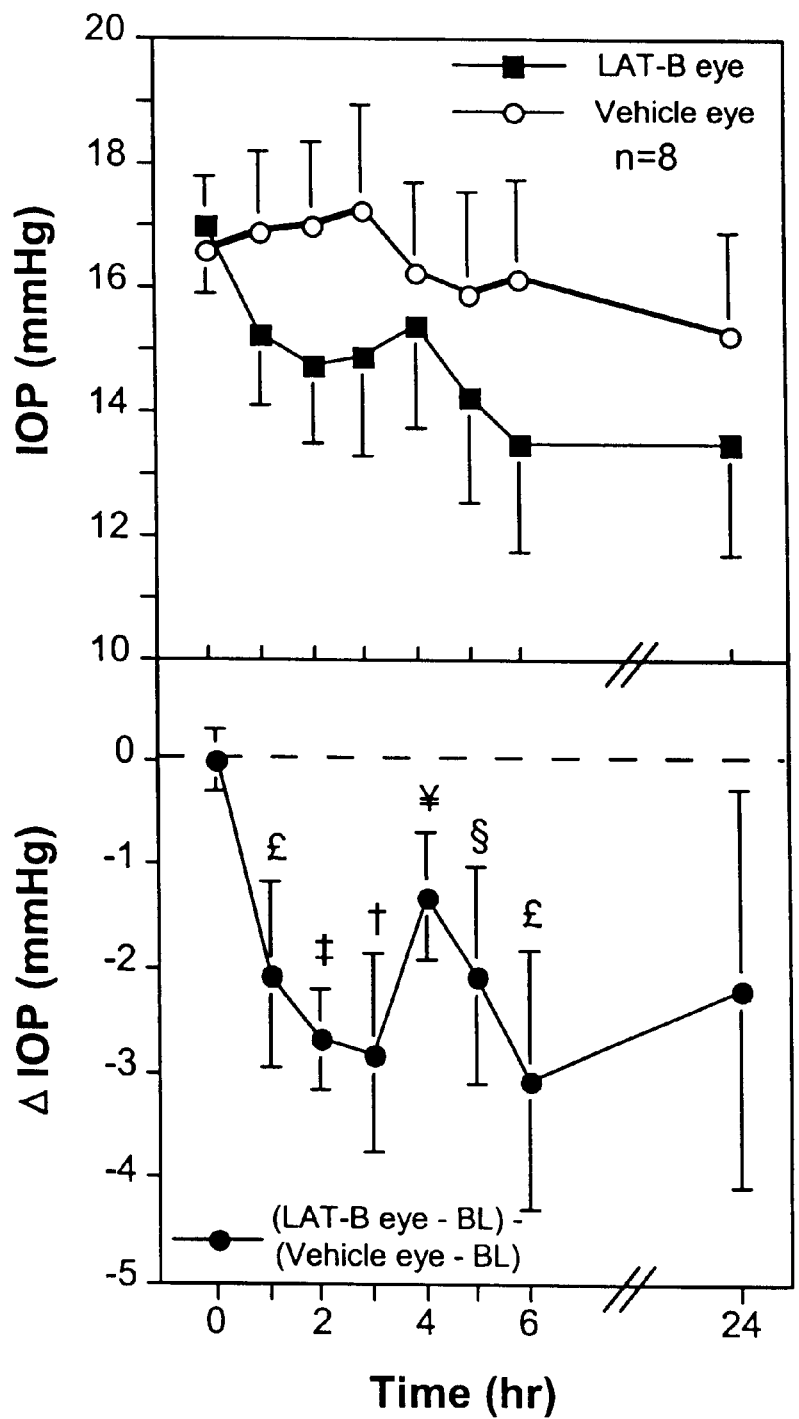
FIG. 16 shows the effect of topically administered 4.0 $\mu$g LAT-B on IOP. In this Figure, "BL" indicates the baseline. The dashed line represents no change from time 0 BL. The data are presented as the mean±s.e.m. for 8 monkeys at that time, each contributing one LAT-B-treated and one vehicle-treated eye to the data set. The IOP reduction was significantly different from 0.0 by the 2-tailed paired t-test for differences: $^\S p<0.025$, $^\pounds p<0.02$, $^\Upsilon p<0.01$, $^\dagger p<0.005$, $^\ddagger p<0.001$.

After LAT-B treatment, the IOP decreased from 17 mmHg to 15 mmHg within 1 hr and to 13.5 mmHg at 6 hr. After adjustment for baseline and contralateral control eyes, the maximal reduction of 3.1±1.2 mmHg (n=8, P<0.02) occurred 6 hr after drug administration; some IOP effect may have remained at 24 hr, as shown in FIG. 16.

Aqueous Humor Flow and Corneal Endothelial Permeability

AHF rate was determined noninvasively by scanning ocular fluorophotometry (Fluorotron Master, Coherent/Ocumetrics). Each monkey was examined biomicroscopically and background fluorescence in the cornea and AC was determined prior to fluorescein administration. On the afternoon preceding LAT-A or B administration (usually ~4:00–5:00 $\mu$m), one drop of 0.5% proparacaine HCl (Alcaine®, Alcon) was administered bilaterally (to enhance corneal penetration of fluorescein) to supine ketamine-anesthetized monkeys. Five min later, five 2 $\mu$l drops of 2% fluorescein Na (Alcon) were applied to the central cornea bilaterally at 30–60 sec. intervals. Blinking was prevented between drops and for 5 min after the final drop with lid speculums. The next morning (usually ~9:00–10:00 am), following a saline flush of the conjunctival sac, four 5 $\mu$l drops of 5 mM LAT-A (42 $\mu$g) or four 5 $\mu$l drops of 500 $\mu$M LAT-B (4 $\mu$g) were administered to the central cornea of one eye, and four 5 $\mu$l drops of vehicle (25% DMSO) to the opposite eye, with 1-min intervals between drops in each eye with the monkey kept supine. Blinking was prevented as described above. Beginning 30 min later, corneal and AC fluorescence was measured every 30 min for 6 hr. AC volume was estimated from corneal thickness, AC depth, corneal curvature, and corneal diameter, all determined optically (See, Erickson et al., Curr. Eye Res., 3:557–564 [1974]) AHF rate and $k_a$ (i.e., the transfer coefficient for fluorescein exchange across the corneal endothelium into the AC, calculated as the area of the corneal endothelium divided by the volume of the cornea and multiplied by the permeability coefficient of endothelium from aqueous to cornea; Ota et al., Invest. Ophthalmol., 13:945–949[1974]) were then calculated by a modified method (See, Brubaker, in Duane (ed.), *Clinical Ophthalmology*, Harper & Row, New York [1986], pp. 3:1–11) of Jones and Maurice (Jones and Maurice, Exp. Eye Res., 5:208–220 [1966]), as known in the art. Baseline AHF was measured in a similar way, without drug or placebo 2–13 days before and 10–26 days after LAT-A or B administration.

The two AHF baselines for individual eyes were similar and were therefore averaged. The vehicle had no effect on flow rate during any interval. LAT-A increased apparent AHF by 87±13% (n=8, p<0.001; Table 11) in the first 3 hr, relative to vehicle-treated controls and adjusted for baseline. During the second 3 hr, there were no significant differences between drug- and vehicle-treated eyes. Overall, the $k_a$ value increased by 94±9% (n=8, p<0.001), with the increase perhaps slightly greater during the first 3 hr (106±16%; p<0.001) than during the second 3 hr (68±10%; p<0.001; Table 11). The relative difference between the first and second 3-hr intervals was 27±12% (p<0.1). After LAT-B administration there was only a small, insignificant increase in AHF during the first 3 hr, and little effect on AHF overall (Table 12). LAT-B increased $k_a$ by 39±5% (n=6, p<0.001; Table 12) during the overall 6 hr measurement period, with the greatest increase during the first 3 hr (58±20%, p<0.05).

In Table 11 the results are shown for topical administration of vehicle or 42 $\mu$g LAT-A in contralateral eyes of eight monkeys. In Table 12, the results are shown for topical administration of vehicle or 4.0 $\mu$g LAT-B in contralateral eyes. In Table 11, "BL" is the average of the baseline values for AHF or $k_a$ measured 2 to 8 days before and 10 days after LAT-A treatment; "Rx" refers to results after drug administration. The AHF data are presented as the mean±s.e.m. microliters per minutes. The $k_a$ data are presented as the mean±s.e.m.×10$^{-3}$/minute. The times indicated correspond to the number of hours after treatment. The ratios are unitless. The P values in this Table were determined using the two-tailed paired t-test for ratios different from 1.0.

In Table 12, "BL" is the average of baseline values for AHF or $k_a$ measured 5 to 13 days before and 14 to 26 days after LAT-B and vehicle treatment; "Rx" refers to the results obtained after drug administration. The data are presented as the mean±s.e.m. For AHF, the results are shown as ml per minute, while the ka, the results are shown for the mean±s.e.m.×10$^{-3}$×min$^{-1}$. The ratios are unitless; "n"=6; the times shown are hours after treatment. The P values indicated in this Table were determined using the two-tailed paired t-test for ratios different from 1.0.

TABLE 11

Effect of 42 μg Topical LAT-A on AHF and $k_a$

| Sample/Time | Hour 0.5 to 3.0 | | | Hour 3.5 to 6.0 | | | Hour 0.5 to 6.0 | | |
|---|---|---|---|---|---|---|---|---|---|
| | LAT-A | Vehicle | LAT-A/Vehicle | LAT-A | Vehicle | LAT-A/Vehicle | LAT-A | Vehicle | LAT-A/Vehicle |
| AHF | | | | | | | | | |
| BL | 1.97 ± 0.21 | 1.92 ± 0.22 | 1.03 ± 0.03 | 1.89 ± 0.13 | 1.97 ± 0.18 | 0.98 ± 0.04 | 1.93 ± 0.15 | 1.96 ± 0.19 | 1.00 ± 0.02 |
| Rx | 3.48 ± 0.30 | 1.87 ± 0.21 | 1.94 ± 0.14‡ | 1.87 ± 0.25 | 1.88 ± 0.18 | 1.00 ± 0.09 | 2.65 ± 0.25 | 1.80 ± 0.20 | 1.51 ± 0.08 |
| Rx/BL | 1.82 ± 0.14 | 1.00 ± 0.09 | 1.87 ± 0.13‡ | 1.00 ± 0.12 | 0.98 ± 0.08 | 1.01 ± 0.07 | 1.38 ± 0.09 | 0.92 ± 0.06 | 1.51 ± 0.06‡ |
| $k_a$ | | | | | | | | | |
| BL | 5.45 ± 0.19 | 5.21 ± 0.16 | 1.05 ± 0.02* | 5.74 ± 0.16 | 5.77 ± 0.21 | 1.00 ± 0.03 | 5.58 ± 0.14 | 5.50 ± 0.15 | 1.02 ± 0.02 |
| Rx | 9.96 ± 0.59 | 4.79 ± 0.44 | 2.15 ± 0.17‡ | 9.25 ± 1.31 | 5.37 ± 0.37 | 1.69 ± 0.13† | 9.61 ± 0.51 | 4.93 ± 0.31 | 1.98 ± 0.10‡ |
| Rx/BL | 1.84 ± 0.13 | 0.91 ± 0.06 | 2.06 ± 0.16‡ | 1.59 ± 0.19 | 0.93 ± 0.06 | 1.68 ± 0.10‡ | 1.72 ± 0.08 | 0.89 ± 0.04 | 1.94 ± 0.09‡ |

*$P < 0.05$; †$P < 0.005$; and ‡$P < 0.001$, for ratios different from 1.0 by the 2-tailed paired t-test.

TABLE 12

Effect of 4.0 μg Topical LAT-B on AHF and $k_a$

| Sample/Time | Hour 0.5 to 3.0 | | | Hour 3.5 to 6.0 | | | Hour 0.5 to 6.0 | | |
|---|---|---|---|---|---|---|---|---|---|
| | LAT-B | Vehicle | LAT-B/Vehicle | LAT-B | Vehicle | LAT-B/Vehicle | LAT-B | Vehicle | LAT-B/Vehicle |
| AHF | | | | | | | | | |
| BL | 1.92 ± 0.26 | 1.83 ± 0.18 | 1.04 ± 0.05 | 1.87 ± 0.20 | 1.82 ± 0.15 | 1.03 ± 0.09 | 1.88 ± 0.22 | 1.87 ± 0.16 | 1.00 ± 0.05 |
| Rx | 2.37 ± 0.17 | 1.82 ± 0.17 | 1.33 ± 0.12§§ | 1.57 ± 0.18 | 1.71 ± 0.14 | 0.93 ± 0.10 | 1.90 ± 0.16 | 1.67 ± 0.12 | 1.14 ± 0.06* |
| Rx/BL | 1.31 ± 0.15* | 1.01 ± 0.09 | 1.33 ± 0.18 | 0.84 ± 0.05‡ | 0.95 ± 0.07 | 0.91 ± 0.10 | 1.04 ± 0.08 | 0.90 ± 0.04* | 1.16 ± 0.07* |
| $k_a$ | | | | | | | | | |
| BL | 5.09 ± 0.25 | 4.93 ± 0.20 | 1.03 ± 0.03 | 4.84 ± 0.27 | 5.02 ± 0.26 | 0.98 ± 0.07 | 4.88 ± 0.22 | 5.06 ± 0.17 | 0.96 ± 0.04 |
| Rx | 7.35 ± 0.67 | 4.83 ± 0.68 | 1.62 ± 0.18§ | 6.30 ± 0.43 | 5.31 ± 0.31 | 1.21 ± 0.11 | 6.48 ± 0.38 | 4.87 ± 0.34 | 1.34 ± 0.06¶ |
| Rx/BL | 1.44 ± 0.11§ | 0.97 ± 0.12 | 1.58 ± 0.20† | 1.31 ± 0.06¶ | 1.06 ± 0.06 | 1.25 ± 0.08† | 1.33 ± 0.04# | 0.96 ± 0.06 | 1.39 ± 0.05# |

*$P < 0.01$; †$P < 0.05$; ‡$P < 0.025$; §$P < 0.02$; ¶$P < 0.005$; and #$P < 0.001$, for ratios different from 1.0 by the 2-tailed paired t-test.

Blood-Aqueous-Barrier Permeability to Systemic Fluorescein

Topical LAT-A (42 μg) was given to one eye and vehicle to the opposite eye as described above, 1 hr prior to intravenous injection of fluorescein Na in the saphenous vein (10 mg/kg in 500–600 μl) followed by a 4 ml saline flush. The concentration of fluorescein ([fluorescein]) in the cornea and AC was determined by fluorophotometry 15, 30, 45, 60, 90, 120, 180 and 240 min after fluorescein injection.

Figure 17:
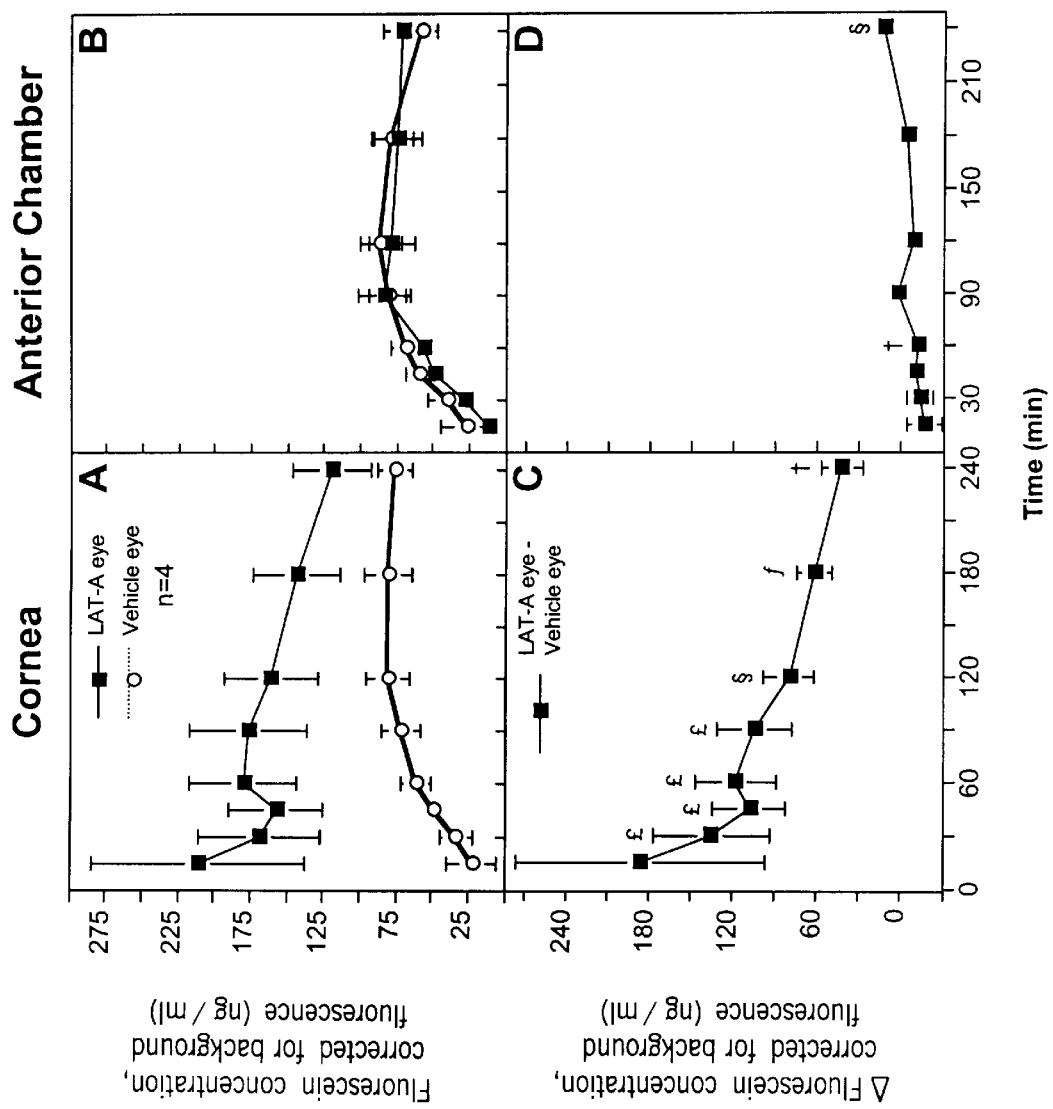
FIGS. 17A–D show the effect of topically administered 42 $\mu$g LAT-A on the rate of entry of fluorescein into the cornea (FIGS. 17A and 17C) and the anterior chamber (FIGS. 17B and 17D), after intravenous injection. The data are presented as the mean±s.e.m. for 4 monkeys (i.e., with each contributing one LAT-A treated and one vehicle treated eye to the data set). Fluorescein was injected at time 0, one hour after topical LAT-A administration. The difference in [fluorescein] between eyes was ≠0.0 by the 2-tailed paired t-test for differences: $^\dagger p<0.1$, $^\pounds p<0.05$, $^{\S p}<0.025$, $^f p<_0.02$.

Fifteen min after i.v. fluorescein injection (1.25 hr after topical LAT-A or vehicle), $[\text{fluorescein}]_{cornea}$ was ~10 times higher in LAT-A-treated eyes than in vehicle-treated eyes. The difference decreased to only ~1.5 times higher after 240 min (FIGS. 17A and 17C). $[\text{Fluorescein}]_{AC}$ increased slowly in both eyes after i.v. injection of fluorescein, but only after 240 min (300 min after drug instillation) was [Fluorescein]$_{AC}$ higher in LAT-A eyes than in vehicle-treated eyes (by 24±3% (n=4, p<0.025); FIGS. 17B and 17D).

Aqueous Humor Protein

Approximately 5.5 hr after LAT-A and vehicle (25% DMSO) administration, or approximately 6.5 hr after LAT-B and vehicle (25% DMSO) administration, when AHF measurements had been completed, a sample of AH was obtained under a Zeiss surgical microscope, using a 30-gauge needle connected via polyethylene tubing to a tuberculin syringe. The needle was threaded through the corneal stroma for 6 mm, then directed into the AC so that the wound was self-sealing. AH entered the tubing by very gentle suction with the tuberculin syringe; only occasionally was brief mild pressure on the cornea with a needle holder required to promote the initial flow of AH into the tubing via the very thin needle. Approximately 60–80 μl of AH was removed, leaving a shallow but not completely flattened AC. In separate protocols with different monkeys, AH was similarly obtained 2 hr after 42 μg LAT-A or 1 hr after 4 μg LAT-B to one eye and vehicle to the opposite eye. The AH samples were stored at −20° C. for up to 24 hr. The protein concentration in each sample was assayed by the Lowry method, as known in the art (See e.g., Lowry et al., J. Biol. Chem., 193:265–275[1951]; and Peterson et al., Anal. Biochem., 100:201–220[1979]), in duplicate, and the result averaged. Duplicate sets of protein standards containing 0, 1, 3, 5, 10, 20, 40, or 60 µg bovine serum albumin (BSA) were assayed by the same method and results averaged and graphed to give a linear equation that was used to estimate the protein content in the AH samples. The optical density of each sample was measured at 660 nm using a Spectronic 20 Spectrophotometer (Bausch and Lomb).

Figure 18:
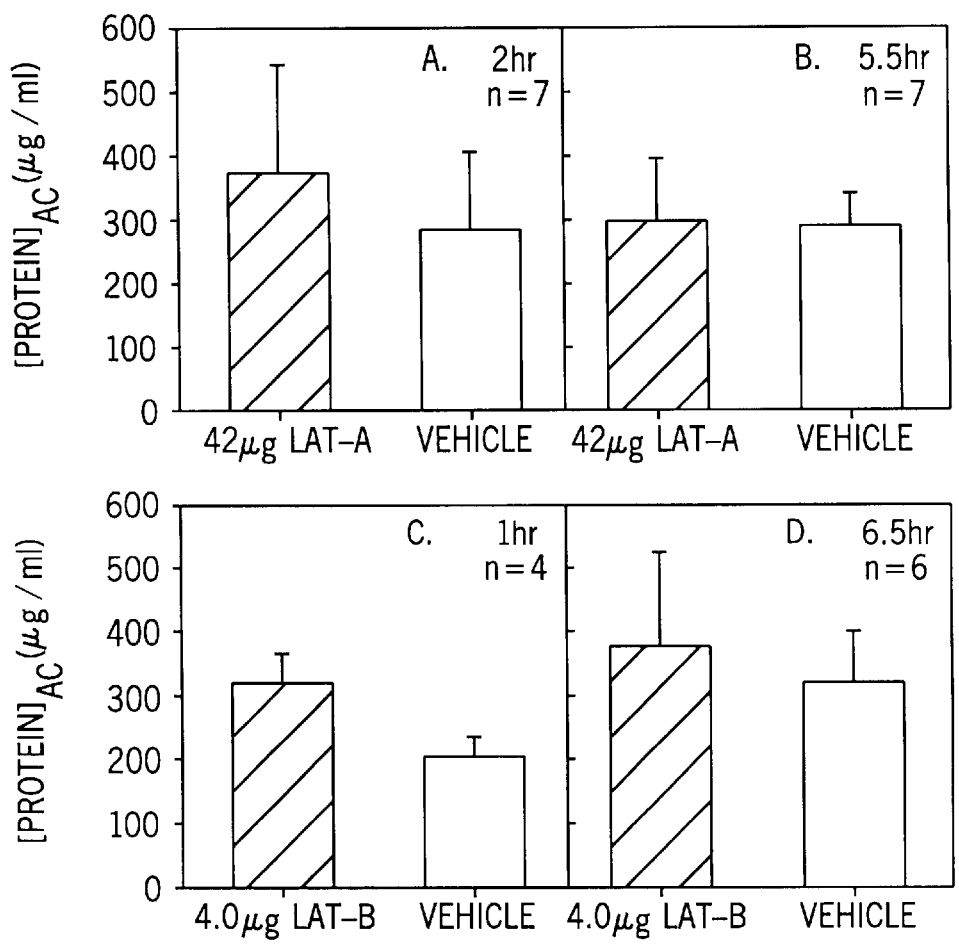
FIGS. 18A–D show the anterior chamber protein concentration (by Lowry method) after topical administration of 42 $\mu$g LAT-A or 4 $\mu$g LAT-B to one eye and vehicle to the opposite eye (FIG. 18A provides the results for tests conducted after 2 hours, while FIG. 18B provides the results for tests conducted 5.5 hours after administration, FIG. 18C provides the results for an eye treated with the vehicle one hour after administration of topical 42 $\mu$g LAT-A to one eye and vehicle to the opposite eye, and FIG. 18D provides the results 6.5 hours after topical 4.0 $\mu$g LAT-B to one eye and vehicle to the opposite eye). Data are presented as the mean±s.e.m. for "n" monkeys, each contributing one LAT-A or LAT-B-treated eye and one vehicle-treated eye to the data set. $^\pounds P<0.05$ for ratios different from 1.0, as determined using the 2-tailed paired t-test.

Two hr after LAT-A administration [Protein]$_{AC}$ in LAT-A-treated eyes was 25±9% higher than that in vehicle-treated eyes (n=7, p<0.05; FIG. 18A). There was no difference in protein concentration at 5.5 hr (FIG. 18B). After LAT-B, [Protein]$_{AC}$ was variable, but overall was insignificantly increased at 1 hr and 6.5 hr (80±51%; n=4 and 11±24%; n=6 respectively; FIGS. 18C and 18D) compared to the contralateral control eyes.

Ultrasonic Pachymetry

Corneal thickness was measured using a DGH-1000 ultrasonic pachymeter (DGH Technology). All eyes were examined by biomicroscopy prior to baseline measurements. Monkeys were placed supine in head holders. The central cornea was measured once and the peripheral cornea was measured four times midway between the center and the limbus on the vertical and horizontal axes. For each point in each eye, two baseline thickness measurements were averaged, and 4.0 µg LAT-B or 25% DMSO was administered to opposite eyes in the LAT-B protocol, or 25% DMSO or Bárány's administered to opposite eyes in the DMSO control protocol. The eyelids were held open manually during and for 5 min. after drug or vehicle administration. Corneal thickness was measured every 30-min. for 6 hr and again at 24 hr.

Figure 19:
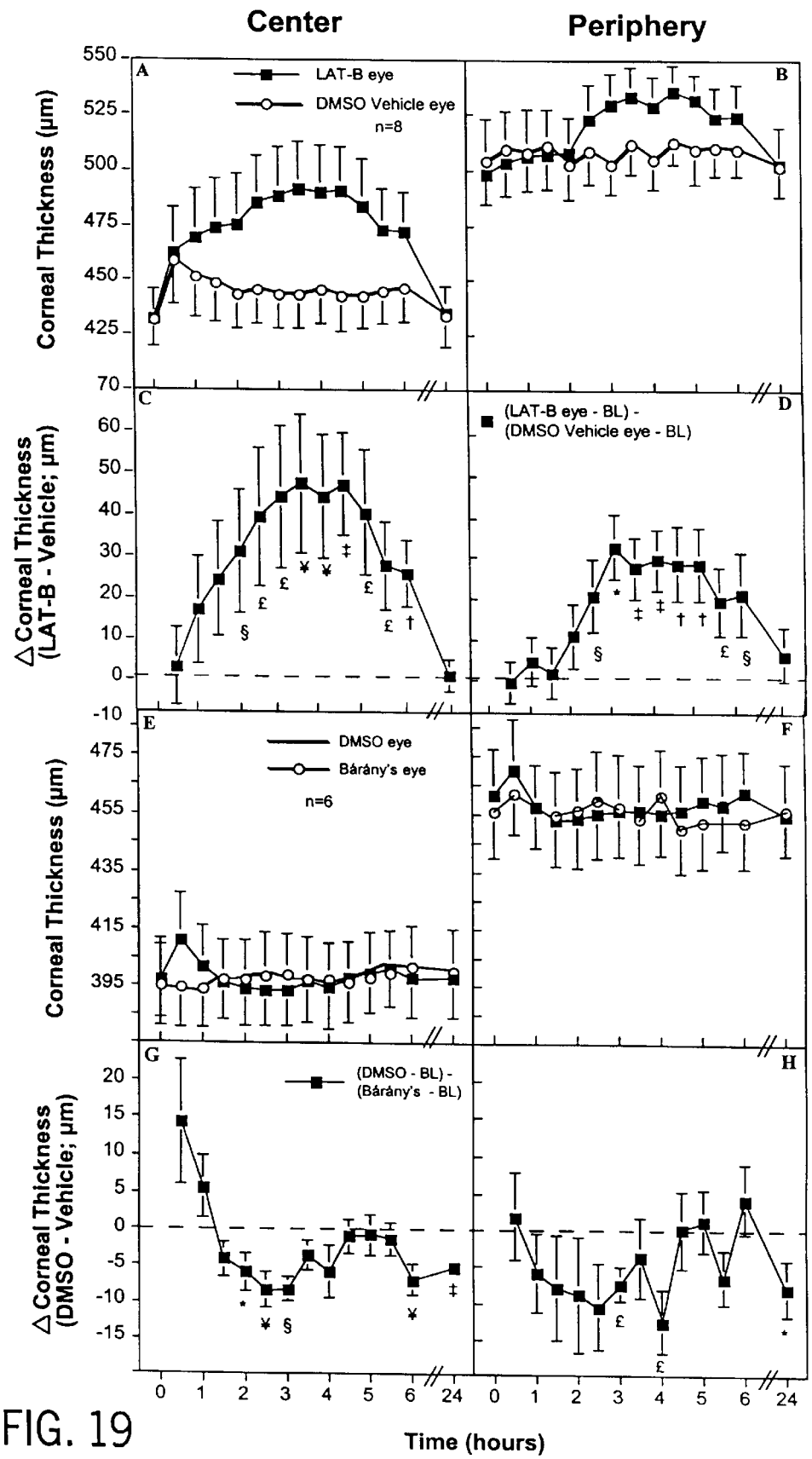
FIGS. 19A–H provide results showing the effect of topical 4.0 $\mu$g LAT-B (FIGS. 19A–D) or 25% DMSO (FIGS. 19E–H) on corneal thickness as measured by ultrasonic pachymetry. In these graphs, "BL" indicates the baseline. The dashed lines represent no change from time 0 BL. Data are presented as mean±s.e.m. for 8 (FIGS. 19A–D) or 6 (FIGS. 19E–H) monkeys, each contributing one LAT-B-treated eye and one 25% DMSO vehicle-treated eye (FIGS. 19A–D), or one DMSO-treated and one Barany vehicle-treated eye (FIGS. 19E–H) to the data set. The differences between eyes were # 0.0 by the 2-tailed paired t-test: *p<0.1, £p<0.05, ¥p<0.025, †p<0.02, ‡p<0.01, §p<0.005.

Within 1 hr after LAT-B administration the central cornea began to swell, and the thickness increased to a maximum of 47±17 µm greater than contralateral control eyes by 3.5 hr (p<0.025, n=8), as indicated in Panels A through D of FIG. 19. The corneas then thinned over time, but were still thicker than controls at 6 hr (Δ=26±8 µm [6±2%], p<0.02). Mid-peripheral corneal thickness also increased 2–5 hr after LAT-B administration, with the greatest increase at 3 hr (Δ=32±8 µm [6±1%], p<0.005). In eyes treated with DMSO vehicle, corneal thickness increased from baseline during the first 30 min (Δ=28±9.6 µm [6±2%], p<0.025), then gradually decreased to baseline by 24 hr. By 24 hr., the central and peripheral corneal thickness in both eyes had returned to baseline. In the DMSO vs Bárány's protocol, there was a variable statistically insignificant tendency for 25% DMSO to thicken the central cornea initially (Δ=14±8.4 µm [4±3%], p<0.2), followed by slight but variably significant thinning of both the central and peripheral cornea (Δ≈5–12 µm [≠1 to 3%]) beyond 2 hr, compared to the contralateral control eyes receiving Bárány's solution, as indicated in Panels E through H of FIG. 19.

Corneal Specular Microscopy

The corneal endothelium of both eyes was photographed using a specular microscope (obtained from Dr. Charles J. Koester, Columbia University) before and 1 hr, 3 hr, 3 days, 7 days, and 14 days after topical administration of 21 or 42 µg LAT-A to one eye and vehicle to the opposite eye. Corneal endothelial cell densities were estimated by counting cells in a reference grid placed over the photograph. Cells in four separate squares were counted and averaged in each photo. All cells completely inside the square and any cells touching two of the lines making up the square were counted. The number of cells was multiplied by 100, to compensate for the magnification of the camera and to determine cell density in cells/mm$^2$. Endothelial cell morphology was evaluated subjectively by a trained corneal specialist.

Baseline specular microphotographs showed normal corneal endothelium with cell densities between 2300–2950 cells/mm$^2$, as indicated in Table 13. A few vehicle-treated eyes exhibited pseudoguttata and bright spots, especially at the higher dose of DMSO. Cells in eyes receiving either dose of LAT-A could not be counted at 1 or 3 hr (Table 13) because the cell borders were not visible and a few pseudoguttata and bright spots were present. By day 3, cell borders in all eyes recovered and cells became countable. The cell densities in eyes that had received 21 µg LAT-A were essentially the same as at baseline, while the eyes that had received 42 µg LAT-A had slightly (but not significantly) lower cell densities than baseline or contralateral eyes (See, Table 13). By day 7 after either dose, cell density and morphology had returned to baseline.

Table 13 provides data showing the effect of 21 or 42 µg LAT-A (2×5 µl or 4×5 µl of 5 mM solution applied topically) on corneal endothelial cell counts. The data are shown as the mean±s.e.m. cell per square millimeter for four cynomolgus monkeys, each contributing one LAT-A-treated and one vehicle-treated eye to the data set. In this Table, "BL" indicates baseline cell counts, and "Exp" indicates the cell counts after LAT-A or vehicle administration. The P values are indicated for ratios that were different from 1.0, as determined using the two-tailed paired t-test.

TABLE 13

Effect of Topical LAT-A on Corneal Endothelial Cell Counts

| Sample/Time | 21 µg LAT-A | | | | 42 µg LAT-A | | | |
|---|---|---|---|---|---|---|---|---|
| | LAT-A | Vehicle | LAT-A/Vehicle | LAT-A−Vehicle | LAT-B | Vehicle | LAT-B/Vehicle | LAT-B−Vehicle |
| BL | 2538 ± 75 | 2638 ± 139 | 0.97 ± 0.03 | −100 ± 86 | 2644 ± 128 | 2444 ± 63 | 1.08 ± 0.03* | 200 ± 87 |
| Exp | | | | | | | | |
| 1 hour | | 2463 ± 74 | | | | 2175 ± 363 | | |
| 3 hours | | 2344 ± 112 | | | | 2619 ± 66 | | |
| 3 days | 2488 ± 63 | 2344 ± 98 | 1.02 ± 0.03 | 44 ± 62 | 2188 ± 430 | 2469 ± 193 | 0.86 ± 0.11 | −281 ± 248 |
| 7 days | 2488 ± 97 | 2556 ± 106 | 0.98 ± 0.06 | −69 ± 140 | 2494 ± 166 | 2400 ± 105 | 1.04 ± 0.03 | 94 ± 68 |
| 14 days | 2694 ± 28 | 2694 ± 130 | 1.01 ± 0.06 | 0 ± 147 | 2581 ± 143 | 2506 ± 103 | 1.03 ± 0.05 | 75 ± 108 |

TABLE 13-continued

Effect of Topical LAT-A on Corneal Endothelial Cell Counts

| | 21 µg LAT-A | | | | 42 µg LAT-A | | | |
|---|---|---|---|---|---|---|---|---|
| Sample/Time | LAT-A | Vehicle | LAT-A/Vehicle | LAT-A-Vehicle | LAT-B | Vehicle | LAT-B/Vehicle | LAT-B-Vehicle |
| Exp/BL | | | | | | | | |
| 1 hour | | 0.94 ± 0.03 | | | | 0.89 ± 0.14 | | |
| 3 hours | | 0.89 ± 0.05 | | | | 1.07 ± 0.03* | | |
| 3 days | 0.98 ± 0.01 | 0.93 ± 0.03* | 1.06 ± 0.02† | 0.05 ± 0.10 | 0.83 ± 0.14 | 1.01 ± 0.06 | 0.80 ± 0.11 | −0.18 ± 0.10 |
| 7 days | 0.98 ± 0.03 | 0.98 ± 0.05 | 1.02 ± 0.08 | 0.01 ± 0.07 | 0.94 ± 0.04 | 0.98 ± 0.02 | 0.96 ± 0.02 | −0.04 ± 0.02 |
| 14 days | 1.06 ± 0.03 | 1.02 ± 0.01 | 1.04 ± 0.03 | 0.04 ± 0.03 | 0.98 ± 0.02 | 1.03 ± 0.02 | 0.95 ± 0.03 | −0.05 ± 0.03 |

*$P < 0.1$ and †$P < 0.05$, for ratios different from 1.0 by the 2-tailed paired t-test.

EXAMPLE 11

Effect of Swinholide-A on Outflow Facility

In this Example, experiments to determine the effects of swinholide-A on outflow facility in monkeys are described.

As indicated above, normal cynomolgus monkeys (*Macaca fascicularis*), weighing 2 to 5 kg, were included in these experiments. All investigations were in accordance with University of Wisconsin and NIH guidelines, and with the ARVO Statement on the Use of Animals in Ophthalmic and Vision Research. Anesthesia was induced by intramuscular (i.m.) ketamine (10 mg/kg), followed by i.v. (15 mg/kg) or i.m. (35 mg/kg) pentobarbital-Na.

Swinholide-A (Swin-A) was obtained from Dr. Benjamin Geiger (Rehovot, Israel), or Alexa, and stored as a 100 µM stock solution in DMSO at −20° C. Swin-A solutions (10 µM to 500 nM), and vehicle (0.01–0.25% DMSO), and corresponding control Lat-B only solution (60 or 200 nM) for intracameral exchange perfusion, were freshly prepared in Bárány's solution.

Total outflow facility was determined by 2-level constant pressure perfusion of the anterior chamber (AC) as described above. The AC of both eyes of the monkey was cannulated with a branched needle with one branch connected to a reservoir and the other to a pressure transducer, and an unbranched needle with tubing clamped off. Following 35 min of bilateral baseline facility measurement, the clamped tubing from the unbranched needle was then connected to a syringe containing drug(s), or corresponding vehicle (or drug) for the control eye. The syringe was placed in a variable speed infusion pump and the tubing previously leading to the reservoir was disconnected from the reservoir and opened to air as a temporary outflow line. This allowed infusion of 2 ml of solution through the AC to exchange the contents of the AC over 10–15 min. IOP was maintained at 15 mm Hg by adjusting the height (e.g., 15–16 cm higher than the eye) of the end of the "temporary outflow" tubing. The reservoir was emptied and re-filled with the same solution being perfused through the eye. The "temporary outflow" tubing was reconnected to the reservoir and the syringe tubing was clamped again, allowing infusion from the reservoir into the eye. Post-exchange outflow facility was then measured for 80–90 min.

Following baseline facility measurements, experiments were conducted to determine the effects of different doses of Swin-A on outflow facility. Thus, the ACs of opposite eyes were exchanged with 10, 100 or 500 nM Swin-A, or corresponding vehicles, with the reservoirs filled with corresponding drug/vehicle solutions. Post-drug facility was measured for 80 or 90 min beginning 60 min after drug administration. The results are shown in Table 14, below. In this Table, the post-treatment facility is indicated for three intervals for each protocol. For Protocol B, one animal only had 60 minutes of perfusion at the 100 nM dose for the overall 90 minute period. Accordingly, n=7 for the 3rd 30 minute data points for this protocol. Post-treatment facility measurements were begun 60 minutes after drug administration. Facility data are presented as mean±s.e.m. (µl/min/mmHg) for "n" animals, each contributing one eye receiving swinholide and one eye receiving vehicle. As with previous Tables, "BL" refers to baseline, and the ratios are unitless.

TABLE 14

Effect of Swinholide-A on Outflow Facility

| | Swin-A | | | Vehicle | | | Swin-A/Vehicle | | |
|---|---|---|---|---|---|---|---|---|---|
| Protocols | BL | Rx | Rx/BL | BL | Rx | Rx/BL | BL | Rx | Rx/BL |
| A. (n = 8) 10 nM | | | | | | | | | |
| 80 min. | 0.38 ± 0.06 | 0.46 ± 0.09 | 1.18 ± 0.12 | 0.33 ± 0.05 | 0.44 ± 0.07 | 1.35 ± 0.13† | 1.16 ± 0.12 | 1.00 ± 0.10 | 0.91 ± 0.11 |
| 1st 30 min. | | 0.34 ± 0.07 | 0.90 ± 0.10 | | 0.36 ± 0.05 | 1.10 ± 0.09 | | 0.92 ± 0.07 | 0.83 ± 0.09 |
| 2nd 30 min. | | 0.44 ± 0.09 | 1.13 ± 0.11 | | 0.44 ± 0.07 | 1.32 ± 0.10‡ | | 0.99 ± 0.12 | 0.89 ± 0.10 |
| Last 20 min. | | 0.56 ± 0.12 | 1.44 ± 0.18† | | 0.57 ± 0.11 | 1.74 ± 0.25‡ | | 0.99 ± 0.13 | 0.95 ± 0.20 |

TABLE 14-continued

Effect of Swinholide-A on Outflow Facility

| | Swin-A | | | Vehicle | | | Swin-A/Vehicle | | |
|---|---|---|---|---|---|---|---|---|---|
| Protocols | BL | Rx | Rx/BL | BL | Rx | Rx/BL | BL | Rx | Rx/BL |
| B. (n = 8) 100 nM | | | | | | | | | |
| 90 min. | 0.33 ± 0.03 | 0.62 ± 0.12 | 1.86 ± 0.21§ | 0.39 ± 0.06 | 0.60 ± 0.11 | 1.59 ± 0.22† | 1.07 ± 0.31 | 1.20 ± 0.25 | 1.25 ± 0.16 |
| 1st 30 min. | | 0.41 ± 0.05 | 1.26 ± 0.11† | | 0.39 ± 0.07 | 1.05 ± 0.11 | | 1.21 ± 0.26 | 1.26 ± 0.15 |
| 2nd 30 min. | | 0.60 ± 0.11 | 1.79 ± 0.19§ | | 0.58 ± 0.10 | 1.55 ± 0.18‡ | | 1.14 ± 0.21 | 1.21 ± 0.14 |
| 3rd 30 min. | | 0.85 ± 0.19 | 2.41 ± 0.40‡ | | 0.81 ± 0.18 | 2.09 ± 0.38† | | 1.31 ± 0.35 | 1.27 ± 0.22 |
| C. (n = 8) 500 nM | | | | | | | | | |
| 90 min. | 0.23 ± 0.04 | 0.45 ± 0.10 | 2.00 ± 0.34‡ | 0.27 ± 0.03 | 0.28 ± 0.03 | 1.07 ± 0.09 | 0.88 ± 0.11 | 1.51 ± 0.24 | 1.80 ± 0.21§ |
| 1st 30 min. | | 0.28 ± 0.05 | 1.32 ± 0.19 | | 0.21 ± 0.02 | 0.83 ± 0.08* | | 1.27 ± 0.14 | 1.65 ± 0.29 |
| 2nd 30 min. | | 0.43 ± 0.09 | 1.87 ± 0.30‡ | | 0.28 ± 0.03 | 1.07 ± 0.09 | | 1.44 ± 0.23 | 1.70 ± 0.19§ |
| 3rd 30 min. | | 0.59 ± 0.14 | 2.57 ± 0.52‡ | | 0.33 ± 0.04 | 1.23 ± 0.11* | | 1.68 ± 0.31 | 1.98 ± 0.27§ |

*$P < 0.1$; †$P < 0.05$; ‡$P < 0.025$; and §$P < 0.01$, for ratios different from 1.0 by the 2-tailed paired t-test.

In the present study, 500 nM Swin-A time-dependently increased outflow facility in the monkey eye similar to the latrunculins, as discussed above. Although Lat-A elevates the level of G-actin while Swin-A elevates the level of dimeric actin in cultured cells, both of these compounds have been shown to reduce the level of F-actin, accompanied by similar changes in cell morphology (See, Lyubimova et al., J. Cell. Biochem., 65:469–478[1997]). Therefore, it is contemplated that the depolymerization of F-actin in the TM/SC is a common mechanism for the outflow facility action of these compounds. In cultured cells, the increase of G-actin after Lat-A inhibits actin synthesis, whereas the formation of dimeric actin after Swin-A reduces G-actin and in turn enhances actin synthesis (See, Lyubimova et al., supra). In addition, the effect of Swin-A on actin synthesis is similar to that of phalloidin although their mechanisms are different. Phalloidin stabilizes F-actin and reduces the level of G-actin and enhances actin synthesis (Serpinskaya et al., FEBS Lett., 277:11–14 [1990]; Bershadsky et al, J. Cell. Sci., 108:1183–1193[1995]; Reuner et al., FEBS Lett., 286:100–104[1991]; and Reuner et al., Eur. J. Clin. Chem. Clin. Biochem., 33:569–574[1995]). Theoretically, the enhancement of actin synthesis may prompt the conversion from G-actin to F-actin, although the degree of polymerization in vivo is tightly controlled and excess G-actin can be immediately "buffered" by sequestering proteins (e.g., theymosine). However, Swin-A severs F-actin, reduces G-actin and stabilizes the actin into a dimeric form (See, Lyubimova et al., supra). Therefore, Swin-A-induced increase of actin synthesis would not alter its effect on F-actin. Unlike Swin-A, phalloidin has no effect on outflow facility itself and partially inhibits the effect of cytochalasin B on outflow facility (Robinson et al., Arch. Ophthalmol., 112:1610–1613[1994]). The different effects of Swin-A and phalloidin on the actin cytoskeleton in cultured cells and on outflow facility in living monkeys further suggest that reduction and/or disorganization of F-actin, rather than alterations of G-actin, dimeric actin or actin synthesis, is involved in the facility-increasing mechanism of these cytoskeletal drugs. However, an understanding of the mechanism(s) is not necessary in order to utilize the present invention. Indeed, it is not intended that the present invention be limited to any particular mechanism(s).

Figure 20:
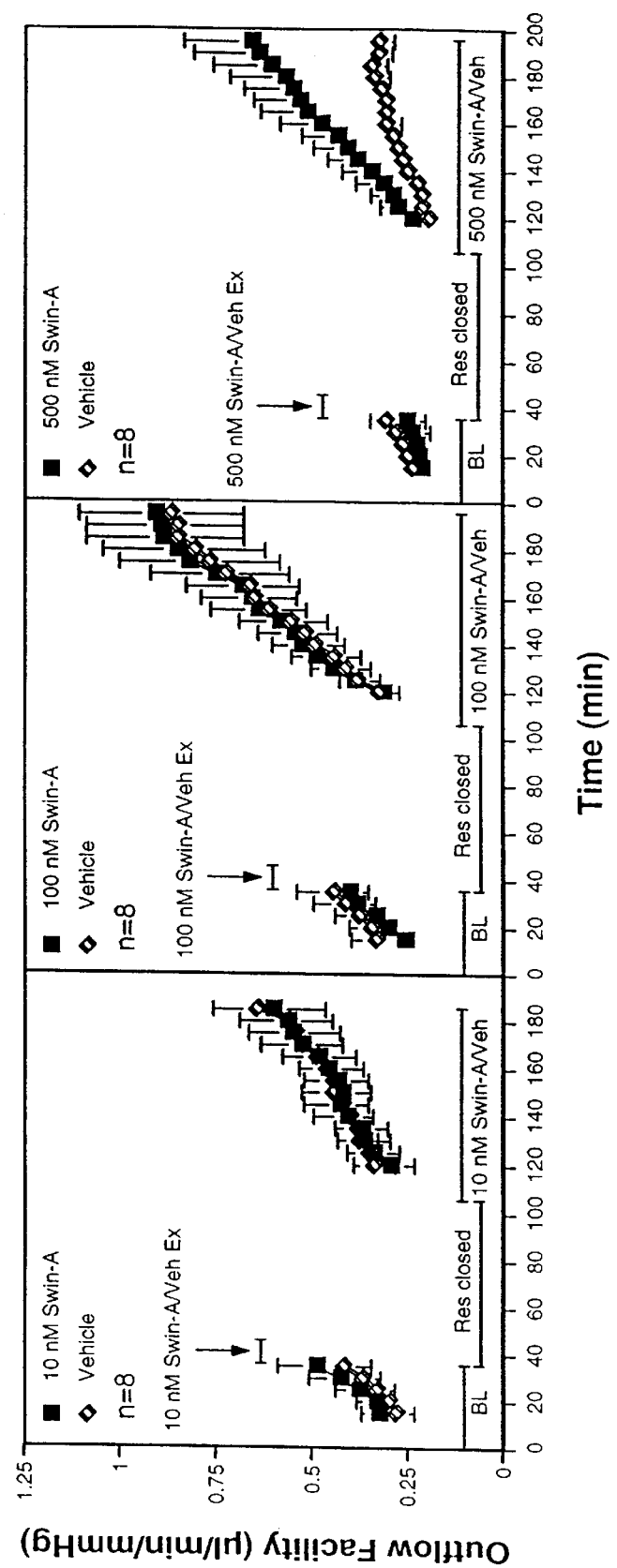
FIG. 20 shows the effect of anterior chamber (AC) exchange (Ex) plus continuous intracameral infusion with 10, 100 or 500 nM swinholide A (Swin) on outflow facility. As above, "BL" indicates the baseline. "Res closed" indicates the time that the fluid reservoir was closed. "Veh" indicates vehicle. Data are presented as mean±s.e.m. $\mu$l/min/mnmHg, for "n" monkeys, each contributing one swinholide A-treated and one vehicle-treated eye. BL was measured for 35 minutes; post-drug facility was measured for 80–90 minutes, beginning 60 minutes after drug administration.

As indicated in Table 14, in 80 or 90-min post-drug perfusions, 10 or 100 nM Swin-A had no significant effect on outflow facility, with ([post-drug facility /baseline]$_{Treated}$/[post-drug facility/baseline]$_{Control}$)=0.91±0.11 (n=8, P>0.4) or 1.25+0.16 (n=8, P>0.1). However, 500 nM Swin-A significantly increased outflow facility by 80±21% (double ratio=1.80±0.21, n=8, P<0.01), adjusted for baseline and resistance washout in contralateral control eyes (See, FIG. 20 and Table 14). These results indicate that Swin-A increases outflow facility in a manner that is similar to latrunculins in living monkeys. However, an understanding of the mechanism(s) is not necessary in order to utilize the present invention. Indeed, it is not intended that the present invention be limited to any particular mechanism(s).

EXAMPLE 12

Effect of Jasplakinolide (Jas) on Outflow Facility

In this Example, experiments to determine the effects of Jas on outflow facility are described. In addition, combinations of Jas with latrunculin B (lat-B) were also tested. Jas was obtained from Molecular Probes and stored as a 0.1 or 1 mM stock solution in DMSO (Sigma), at −20° C. Lat-B was obtained from Calbiochem-Novabiochem, and stored as a 0.2 or 2 mM stock solution in DMSO at −20° C. Jas solution (20 μM to 2.5 μM) and corresponding vehicle (0.01 to 0.25% DMSO) or Jas plus Lat-B solution (60 or 200 nM Lat-B plus 500 nM Jas) and corresponding control Lat-B only solution (60 or 200 nM) for intracameral exchange perfusion, were freshly prepared in Bárány's solution (Bárány, supra). In these experiments, total outflow facility was measured as described in Example 1 1, above.

As indicated above, normal cynomolgus monkeys (*Macaca fascicularis*), weighing 2 to 5 kg, were included in these experiments. All investigations were in accordance with University of Wisconsin and NIH guidelines, and with the ARVO Statement on the Use of Animals in Ophthalmic and Vision Research. Anesthesia was induced by intramuscular (i.m.) ketamine (10 mg/kg), followed by i.v. (15 mg/kg) or i.m. (35 mg/kg) pentobarbital-Na.

Total outflow facility was determined by 2-level constant pressure perfusion of the anterior chamber (AC) as described above. The AC of both eyes of the monkey was cannulated with a branched needle with one branch connected to a reservoir and the other to a pressure transducer, and an unbranched needle with tubing clamped off. Following 35 min of bilateral baseline facility measurement, the clamped tubing from the unbranched needle was then connected to a syringe containing drug(s), or corresponding vehicle (or drug) for the control eye. The syringe was placed in a variable speed infusion pump and the tubing previously leading to the reservoir was disconnected from the reservoir and opened to air as a temporary outflow line. This allowed infusion of 2 ml of solution through the AC to exchange the contents of the AC over 10–15 min. IOP was maintained at ~15 mm Hg by adjusting the height (e.g., 15–16 cm higher than the eye) of the end of the "temporary outflow" tubing. The reservoir was emptied and re-filled with the same solution being perfused through the eye. The "temporary outflow" tubing was reconnected to the reservoir and the syringe tubing was clamped again, allowing infusion from the reservoir into the eye. Post-exchange outflow facility was then measured for 80–90 min.

Following baseline facility measurements, experiments were conducted to determine the effects of different doses of Jas on outflow facility. Thus, the ACs of opposite eyes were exchanged with 20, 100, 500 $\mu$M or 2.5 $\mu$M Jas or corresponding vehicles, with the reservoirs filled with corresponding drug/vehicle solutions. Post-drug facility was measured for 90 min beginning 30 min after drug administration. The results are shown in Table 15, below. In Table 15, facility data are presented as mean±s.e.m. ($\mu$l/min/mmHg) for "n" animals, each contributing one eye receiving Jas and one eye receiving vehicle. As with previous Tables, the ratios are unitless. In Table 15, "BL" refers to 35 minutes baseline; "Rx" refers to post-drug facility at the indicated interval (one animal only had 65 minutes of perfusion and two animals had 130 minutes of perfusion at the 2.5 $\mu$M (microM) dose for the overall 90 minute interval. Accordingly, n=8 in the 3rd 30 minute data period for this protocol).

Figure 21:
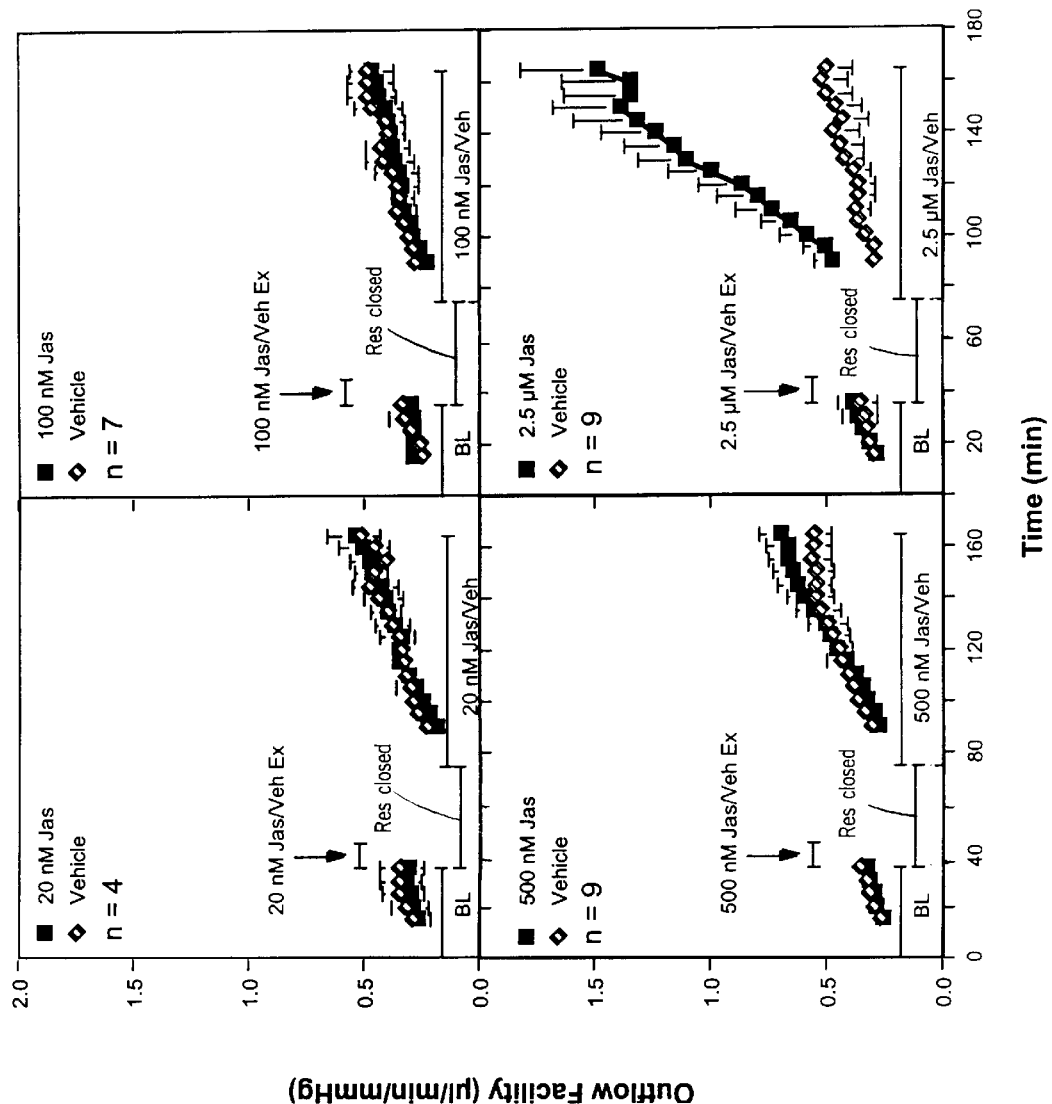
FIG. 21 shows the effect of anterior chamber (AC) exchange (Ex) plus continuous intracameral infusion with 20, 100 or 500 nM or 2.5 $\mu$M jasplakinolide (Jas) on outflow facility. As above, "BL" indicates the baseline. "Res closed" indicates the time that the fluid reservoir was closed. "Veh" indicates vehicle. Data are presented as mean±s.e.m. $\mu$l/min/mmHg, for "n" monkeys, each contributing one jasplakinolide-treated and one vehicle-treated eye. BL was measured for 35 minutes; post-drug facility was measured for 90 minutes, beginning 30 minutes after drug administration.

As indicated in Table 15 and FIG. 21, in 90 minute post-drug perfusions, 20, 100 and 500 nM Jas had no significant effect on outflow facility, with ([post-drug facility/baseline]$_{treated}$/[post-drug facility/baseline]$_{control}$)= 1.10±0.05 (n=4, P>0.2), 0.91±0.10 (n=7, P>0.3), or 1.22±0.26 (n=5, P>0.4), respectively. However, 2.5 $\mu$M Jas significantly increased outflow facility by 157±57% (double ratio=2.57±0.57, n=9, P<0.025), adjusted for baseline and resistance washout in contralateral eyes.

TABLE 15

Effect of Jasplakinolide on Outflow Facility

| Protocols | Jas | | | Vehicle | | | Jas/Veh | | |
|---|---|---|---|---|---|---|---|---|---|
| | BL | Rx | Rx/BL | BL | Rx | Rx/BL | BL | Rx | Rx/BL |
| A. 20 nM (n = 4) | | | | | | | | | |
| 90 min. | 0.30 ± 0.07 | 0.37 ± 0.06 | 1.28 ± 0.07† | 0.33 ± 0.07 | 0.37 ± 0.06 | 1.18 ± 0.08 | 0.98 ± 0.21 | 1.05 ± 0.18 | 1.10 ± 0.05 |
| 1st 30 min. | | 0.24 ± 0.04 | 1.82 ± 0.06* | | 0.27 ± 0.05 | 0.83 ± 0.07* | | 0.98 ± 0.21 | 0.99 ± 0.02 |
| 2nd 30 min. | | 0.36 ± 0.06 | 1.25 ± 0.10* | | 0.36 ± 0.06 | 1.11 ± 0.09 | | 1.13 ± 0.28 | 1.13 ± 0.04† |
| 3rd 30 min. | | 0.49 ± 0.09 | 1.67 ± 0.11‡ | | 0.47 ± 0.07 | 1.50 ± 0.15† | | 1.05 ± 0.11 | 1.15 ± 0.14 |
| B. 100 nM (n = 7) | | | | | | | | | |
| 90 min. | 0.29 ± 0.05 | 0.36 ± 0.07 | 1.21 ± 0.09† | 0.30 ± 0.05 | 0.39 ± 0.06 | 1.40 ± 0.14† | 1.15 ± 0.22 | 0.96 ± 0.14 | 0.91 ± 0.10 |
| 1st 30 min. | | 0.27 ± 0.04 | 0.94 ± 0.06 | | 0.31 ± 0.05 | 1.07 ± 0.09* | | 0.98 ± 0.15 | 0.92 ± 0.08 |
| 2nd 30 min. | | 0.35 ± 0.07 | 1.16 ± 0.09 | | 0.38 ± 0.06 | 1.38 ± 0.15† | | 0.94 ± 0.14 | 0.89 ± 0.10 |
| 3rd 30 min. | | 0.43 ± 0.08 | 1.47 ± 1.13‡ | | 0.47 ± 0.07 | 1.68 ± 0.19‡ | | 0.97 ± 0.14 | 0.91 ± 0.10 |
| C. 500 nM (n = 9) | | | | | | | | | |
| 90 min. | 0.30 ± 0.04 | 0.05 ± 0.06 | 1.78 ± 0.24‡ | 0.31 ± 0.04 | 0.47 ± 0.07 | 1.50 ± 0.12¶ | 1.10 ± 0.22 | 1.20 ± 0.22 | 1.21 ± 0.16 |
| 1st 30 min. | | 0.32 ± 0.03 | 1.12 ± 0.11 | | 0.35 ± 0.05 | 1.13 ± 0.05† | | 0.98 ± 0.14 | 1.00 ± 0.10 |
| 2nd 30 min. | | 0.47 ± 0.05 | 1.67 ± 0.23‡ | | 0.47 ± 0.07 | 1.47 ± 0.14§ | | 1.20 ± 0.27 | 1.17 ± 0.15 |
| 3rd 30 min | | 0.66 ± 0.08 | 2.38 ± 0.67§ | | 0.56 ± 0.08 | 1.79 ± 0.17¶ | | 1.33 ± 0.24 | 1.38 ± 0.22 |
| D. 2.5 nM (n = 9) | | | | | | | | | |
| 90 min. | 0.34 ± 0.05 | 1.01 ± 0.18 | 3.29 ± 0.82‡ | 0.33 ± 0.06 | 0.42 ± 0.08 | 1.27 ± 0.06¶ | 1.20 ± 0.24 | 2.90 ± 0.64 | 2.57 ± 0.57‡ |
| 1st 30 min. | | 0.56 ± 0.09 | 1.86 ± 0.45* | | 0.33 ± 0.05 | 1.03 ± 0.04 | | 1.91 ± 0.40 | 1.80 ± 0.40* |
| 2nd 30 min. | | 0.95 ± 0.18 | 3.11 ± 0.83† | | 0.40 ± 0.08 | 1.18 ± 0.07† | | 3.11 ± 0.84 | 2.83 ± 0.82† |
| 3rd 30 min | | 1.38 ± 0.29 | 4.48 ± 1.28* | | 0.49 ± 0.12 | 1.62 ± 0.14¶ | | 3.17 ± 0.69 | 2.60 ± 0.56‡ |

*P < 0.1; †P < 0.05; ‡P < 0.025; §P < 0.01; and ¶P < 0.005, for ratios different from 1.0 by the 2-tailed paired t-test.

Figure 22:
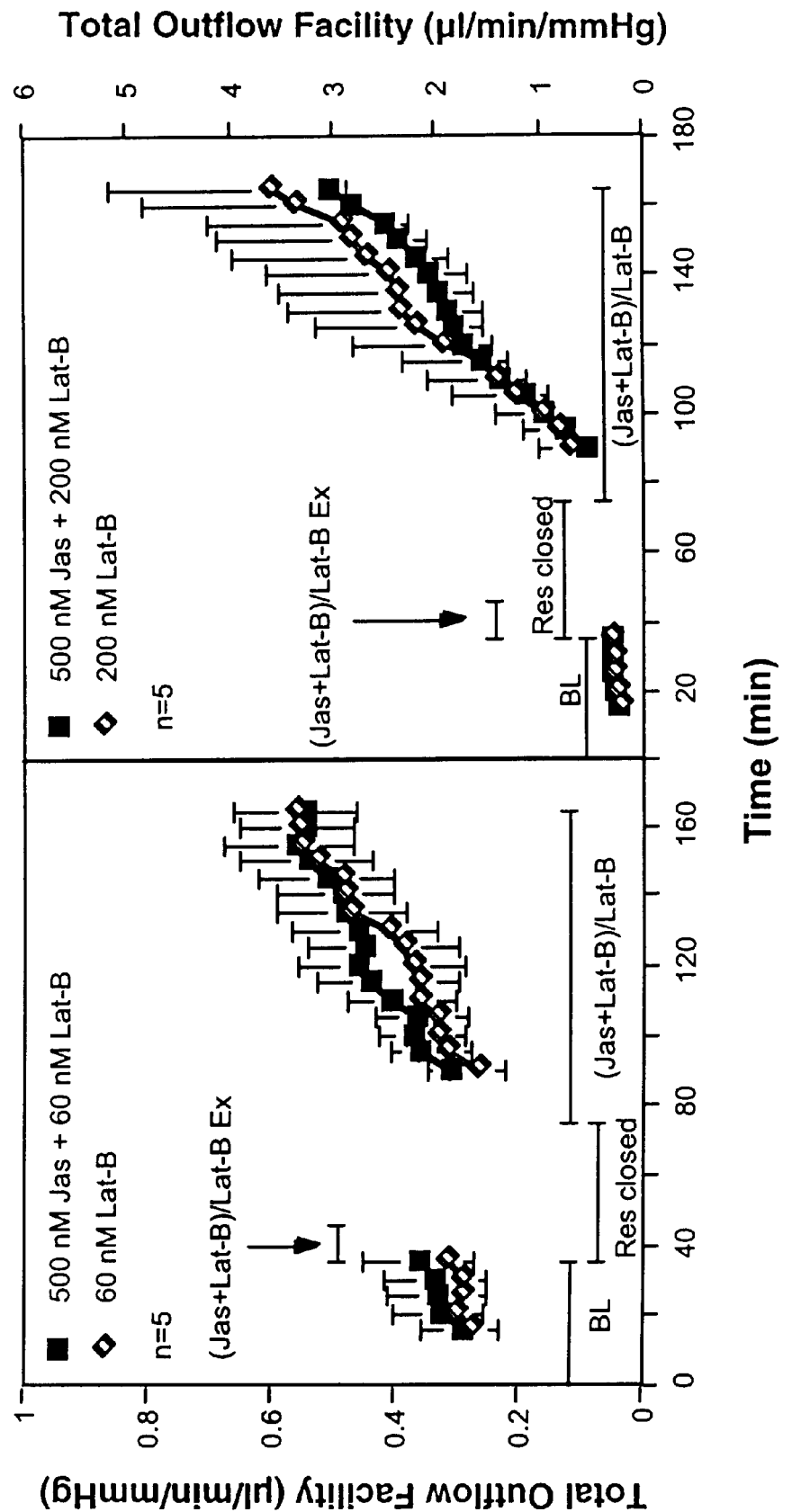
FIG. 22 shows the combined effect of anterior chamber (AC) exchange (Ex) plus continuous intracameral infusion with 500 nM jasplakinolide (Jas) plus 60 or 200 nM latrunculin-B on outflow facility for 5 animals (i.e., n=5). As above, "BL" indicates the baseline. "Res closed" indicates the time that the fluid reservoir was closed. "Veh" indicates vehicle. Data are presented as mean±s.e.m. $\mu$l/min/nmnHg, for "n" monkeys, each contributing one jasplakinolide and latrunculin B-treated and one latrunculin B-treated (i.e., control) eye. BL was measured for 35 minutes; post-drug facility was measured for 90 minutes, beginning 30 minutes after drug administration.

To determine whether Jas could inhibit the effect of the actin depolymerizer Lat-B on outflow facility, Jas and Lat-B were concurrently administered. Following baseline facility measurements, experiments were conducted to determine the effects of different doses of Jas in combination with Lat-B on outflow facility. Thus, the ACs of opposite eyes were exchanged with 500 nM Jas plus 60 nM/200 nM Lat-B solution, and the anterior chamber of the opposite eye was exchanged with only 60 nM or 200 nM Lat-B solution. The reservoirs filled with corresponding drug/vehicle solutions. Post-drug facility was measured for 80 or 90 min beginning 30 min after drug administration. The results are shown in Table 16 and FIG. 22.

The 500 nM Jas dose did not affect the 200 nM Lat B-induced facility increase, with an increase from baseline of 593±113% (n=5, P<0.01) in the Jas plus Lat B-treated eyes, and 618±215% (n=5, P<0.05) in the Lat B only-treated eyes in the overall 90 minute perfusion. The 500 nM Jas dose also did not affect the 60 nM Lat B-induced facility increase, with a 45±9% increase (n=5, P<0.01) in the Jas plus Lat B-treated eye, and a 44±8% increase (n=5, P<0.05) in the Lat B only-treated eye in the overall 90 minute perfusion.

TABLE 16

Effect of Jasplakinolide on Outflow Facility With and Without Lat-B

| Time & Dosage | Jas + Lat B | | | Lat-B | | | Jas + Lat-B/Lat B | | |
|---|---|---|---|---|---|---|---|---|---|
| | BL | Rx | Rx/BL | BL | Rx | Rx/BL | BL | Rx | Rx/BL |
| 500 uM Jas + 60 nM Lat B | | | | | | | | | |
| 90 min. | 0.33 ± 0.08 | 0.46 ± 0.09 | 1.45 ± 0.09‡ | 0.29 ± 0.04 | 0.42 ± 0.07 | 1.44 ± 0.08‡ | 1.18 ± 0.27 | 1.14 ± 0.22 | 1.02 ± 0.08 |
| 1st 30 min. | | 0.35 ± 0.05 | 1.18 ± 0.12 | | 0.31 ± 0.05 | 1.16 ± 0.02† | | 1.25 ± 0.29 | 1.11 ± 0.11 |
| 2nd 30 min. | | 0.45 ± 0.09 | 1.42 ± 0.09‡ | | 0.39 ± 0.08 | 1.30 ± 0.09† | | 1.24 ± 0.26 | 1.11 ± 0.10 |
| 3rd 30 min. | | 0.54 ± 0.12 | 1.69 ± 0.09§ | | 0.54 ± 0.09 | 1.86 ± 0.18‡ | | 1.06 ± 0.21 | 0.95 ± 0.10 |
| 500 nM Jas + 200 nM Lat B | | | | | | | | | |
| 90 min. | 0.28 ± 0.05 | 1.80 ± 0.22 | 6.93 ± 1.13‡ | 0.26 ± 0.04 | 2.08 ± 0.94 | 7.18 ± 2.15† | 1.11 ± 0.16 | 1.89 ± 0.78 | 1.61 ± 0.63 |
| 1st 30 min. | | 0.85 ± 0.15 | 3.26 ± 0.69† | | 0.92 ± 0.42 | 3.06 ± 0.81* | | 1.35 ± 0.36 | 1.23 ± 0.33 |
| 2nd 30 min. | | 1.73 ± 0.30 | 6.52 ± 1.16‡ | | 1.97 ± 0.90 | 6.81 ± 2.15* | | 2.09 ± 0.96 | 1.75 ± 0.74 |
| 3rd 30 min. | | 2.58 ± 0.19 | 10.19 ± 1.65‡ | | 3.07 ± 1.38 | 10.68 ± 3.27† | | 2.00 ± 0.83 | 1.71 ± 0.68 |

*$P < 0.1$; †$P < 0.05$; ‡$P < 0.01$; and §$P < 0.005$, for ratios different from 1.0 by the 2-tailed paired t-test.

In contrast to the latrunculins and swinholide-A, Jas appears to stabilize actin filaments by binding F-actin, as does phalloidin. Twenty, 100 and 500 nM Jas had no effect on outflow facility in living monkeys. However, 2.5 μM dramatically increased outflow facility in the live monkey eye. This result indicates that higher doses of Jas may actually disrupt the actin cytoskeleton, consistent with previous in vitro observations. For example, Senerowicz et al. reported that Jas induces morphological changes in human prostate carcinoma cells that are similar to those changes induced by cytochalasin E, probably by disrupting the actin cytoskeleton (Senerowicz et al., J. Natl. Cancer Inst., 87:46–51[1995]). Duncan et al., noted that both Jas and cytochalasin E inhibit bombesin-stimulated phosphorylation of focal adhesion kinase in cultured PC-3 cells (Duncan et al., J. Surg. Res., 63:359–363[1996]). Posey et al. reported that Jas causes both cell shape change and a redistribution of the actin cytoskeleton in the IL-2 dependent murine cell line CTLL-20 (Posey et al., J. Biol. Chem., 274:4259–4265 [1999]). Spector et al. confirmed that higher concentrations of Jas have two distinct and apparently opposite effects—destabilization of F-actin bundles in the cytoplasm, and increases in the F-actin mass in the perinuclear region (Spector et al., Microsc. Res. Techn., 47:18–37[1999]).

All of these findings indicate that Jas can induce disorganization of the actin cytoskeleton in a manner as do the cytochalasins, latrunculins, or swinholide-A. However, it is not clear why this potent actin filament stabilizer produces disorganization of actin structures of higher order (e.g., networks, stress fibers, etc.). In general, proper organization of these structures strongly depends upon actin dynamics, as inhibition of depolymerization is as damaging as inhibition of polymerization. Since focal adhesion kinase (FAK) is an intracellular protein localized to focal adhesion plaques (Komberg et al., J. Biol. Chem., 267:23439[1992]), structures composed of the terminal ends of actin filaments and the actin associated proteins, Jas-induced actin disruption may be related to its inhibitory effect on FAK phosphorylation. In addition, it is contemplated that Jas acts directly on F-actin, causing abnormal aggregation, including induction of polymerization of G-actin into amorphous masses or disordered F-actin (Bubb et al, J. Biol. Chem., 275:5163–5170 [2000]), which may also eventually lead to deterioration of F-actin. The inhibitory effects of higher doses of Jas on stress fibers can also be explained by its ability to deplete G-actin, leading to a cellular environment in which there is insufficient polymerization-competent G-actin to maintain stress fibers (Bubb et al., J. Biol. Chem., 275:5163–5170[2000]). Unknown mechanisms beyond actin polymerization may also be involved. Nonetheless, an understanding of the mechanism(s) involved is not necessary in order to use the present invention. Indeed, it is not intended that the present invention be limited to any particular mechanism(s) as it is contemplated that various mechanisms may be found to play a role in the action of Jas.

As 500 nM Jas appears to be a near-threshold dose for outflow facility in living monkeys, this dose of Jas was chosen as an inducer of actin polymerization, in order to investigate whether Jas could inhibit Lat-B's action on the trabecular meshwork and Schlemm's canal. Although Jas is a more potent actin stabilizer and has better cell membrane penetration than phalloidin (Bubb et al., J. Biol. Chem., 269:14869–14871 [1994]; and Senderowicz et al., J. Natl. Cancer Inst., 87:46–51[1995]), the 500 μM Jas dose did not inhibit the facility-increasing effect of 60 or 200 nM Lat-B (i.e., effective increasing dosages). The reasons for the lack of inhibition are unclear. The 500 nM dose may potentially disrupt F-action, as 2.5 μM Jas dramatically increased outflow facility. However, if this is the case, it would be expected that 500 μM Jas would potentiate Lat-B's facility action, as a subthreshold dose of one actin-disrupting agent can potentiate the effect of a subthreshold or submaximally effective dose of another actin-disrupting agent on outflow facility (Tian et al., Exp. Eye Res., 68:649–655 [1999]). Thus, the data appear to indicate that the 500 nM Jas dose probably has no actin-disrupting effect, unless the higher dose of Jas increased outflow facility by a totally different mechanism. Possible explanations for the failure of 500 nM Jas to inhibit the effect of Lat-B on outflow facility include: actin depolymerization may not be the sole target mediating Lat-B's facility-increasing effect; the 500 DM concentration of Jas may not be adequate to inhibit actin depolymerization induced by Lat-B (higher doses of Lat-B were not tried, as they may increase outflow facility themselves); and similar to Lat-A, Lat-B may bind to purified G-actin to form a non-polymerizable 1:1 molar complex (Coue et al., FEBS Lett., 213:316–318[1987]). Jas, which promotes polymerization of purified G-actin, may not promote polymerization of the Lat-B/G-actin complex, whereas Lat-B may still sequester G-actin from polymerization, even though the F-actin is bound by Jas. Nonetheless, as indicated above, an understanding of the mechanism(s) involved is not necessary in order to use the present invention. Indeed, it is not intended that the present invention be limited to any particular mechanism(s) as it is contemplated that various mechanisms may be found to play a role in the action of Jas.

From the above, it is evident that the present invention provides for new agents for the potential treatment of glaucoma. These agents, which act via pharmacological interference with cellular relaxation, cell adhesions and the contractility of actin filaments in the ocular fluid drainage pathways, present a clearly needed alternative to the pharmacological modalities currently employed.

All publications and patents mentioned in the above specification are herein incorporated by reference. Various modifications and variations of the described methods of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the field are intended to be within the scope of the following claims.

We claim:

1. A method of enhancing aqueous humor outflow in the eye of a subject, comprising:
    a) providing a subject and an effective amount of at least one non-corneotoxic ophthalmic preparation that affects actin filament integrity in the eye of said subject; and
    b) administering to said subject, said preparation, whereby the aqueous humor outflow of said subject is enhanced.

2. The method of claim 1, wherein said non-comeotoxic ophthalmic preparation comprises at least one macrolide or a pharmaceutically acceptable salt thereof.

3. The method of claim 2, wherein said macrolide is selected from the group consisting of latrunculin-A, latrunculin-B, swinholide-A, and jasplakinolide.

4. The method of claim 1, wherein said subject has glaucoma.

5. The method of claim 1, wherein said administration is topical.

6. The method of claim 1, wherein said administration is intracameral.

7. The method of claim 1, wherein said administration is intracanalicular.

8. A method of enhancing aqueous humor outflow in the eye, comprising:
    a) providing a subject having glaucoma, and an ophthalmic preparation comprising an effective amount of at least one macrolide or a pharmaceutically acceptable salt thereof; and
    b) administering said ophthalmic preparation to said subject thereby enhancing aqueous humor outflow in the eye of said subject.

9. The method of claim 8, wherein said ophthalmic preparation affects actin filament integrity in the eye of said subject.

10. The method of claim 8, wherein said macrolide is selected from the group consisting of latrunculin-A, latrunculin-B, swinholide-A, and jasplakinolide.

11. The method of claim 8, wherein said administration is topical.

12. The method of claim 8, wherein said administration is intracameral.

13. The method of claim 8, wherein said administration is intracanalicular.

14. A method of preventing the progression of glaucoma, comprising the steps of:
    a) providing a subject having glaucoma and a non-comeotoxic ophthalmic preparation that affects actin filament integrity in the eye; and
    b) administering said non-comeotoxic ophthalmic preparation to said subject under conditions such that the progression of said glaucoma is prevented.

15. The method of claim 14, wherein said non-corneotoxic ophthalmic preparation comprises at least one macrolide.

16. The method of claim 15, wherein said macrolide is selected from the group consisting of latrunculin-A, latrunculin-B, swinholide-A, and jasplakinolide.

17. The method of claim 14, wherein said administration is topical.

18. The method of claim 14, wherein said administration is intracameral.

19. The method of claim 14, wherein said administration is intracanalicular.

* * * * *